US011655448B2

(12) United States Patent
Francis et al.

(10) Patent No.: US 11,655,448 B2
(45) Date of Patent: May 23, 2023

(54) PLACENTA-DERIVED MATRIX AND METHODS OF PREPARING AND USE THEREOF

(71) Applicant: LIFENET HEALTH, Virginia Beach, VA (US)

(72) Inventors: Michael Francis, Virginia Beach, VA (US); Silvia Chen, Virginia Beach, VA (US); Erick Breathwaite, Virginia Beach, VA (US); Rudy Rodriguez, Virginia Beach, VA (US); Alan Smith, Virginia Beach, VA (US); Alexander Huber, Virginia Beach, VA (US); Jung Bok Lee, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 883 days.

(21) Appl. No.: 15/576,954

(22) PCT Filed: May 27, 2016

(86) PCT No.: PCT/US2016/034712
§ 371 (c)(1),
(2) Date: Nov. 27, 2017

(87) PCT Pub. No.: WO2016/196313
PCT Pub. Date: Dec. 8, 2016

(65) Prior Publication Data
US 2018/0155678 A1 Jun. 7, 2018

Related U.S. Application Data

(60) Provisional application No. 62/168,397, filed on May 29, 2015.

(51) Int. Cl.
*C12N 5/00* (2006.01)
*C12N 5/073* (2010.01)

(52) U.S. Cl.
CPC ......... *C12N 5/0068* (2013.01); *C12N 5/0605* (2013.01); *C12N 2501/11* (2013.01); *C12N 2501/113* (2013.01); *C12N 2501/115* (2013.01); *C12N 2501/119* (2013.01); *C12N 2501/305* (2013.01); *C12N 2501/31* (2013.01); *C12N 2509/00* (2013.01); *C12N 2533/52* (2013.01); *C12N 2533/54* (2013.01); *C12N 2533/90* (2013.01)

(58) Field of Classification Search
CPC ................ C12N 5/0068; C12N 5/0605; C12N 2509/00; C12N 2533/09
See application file for complete search history.

(56) References Cited

U.S. PATENT DOCUMENTS

| | | | |
|---|---|---|---|
| 5,116,615 A * | 5/1992 | Gokcen .............. | A61K 38/4886 424/94.63 |
| 6,319,868 B1 | 11/2001 | Gani et al. | |
| 6,734,018 B2 | 5/2004 | Wolfinbarger, Jr. et al. | |
| 6,743,574 B1 | 6/2004 | Wolfinbarger, Jr. et al. | |
| 7,338,757 B2 | 3/2008 | Wolfinbarger, Jr. et al. | |
| 7,727,550 B2 | 6/2010 | Siegal et al. | |
| 8,361,503 B2 | 1/2013 | Badylak et al. | |
| 8,563,232 B2 | 10/2013 | Wolfinbarger, Jr. et al. | |
| 8,574,826 B2 | 11/2013 | Wolfinbarger, Jr. et al. | |
| 9,034,386 B2 | 5/2015 | Flynn | |
| 9,522,218 B2 | 12/2016 | Le Visage et al. | |
| 9,890,411 B2 | 2/2018 | Ahn et al. | |
| 2007/0154552 A1* | 7/2007 | Siegal .................. | C12N 5/0619 424/484 |
| 2009/0274627 A1 | 11/2009 | Yamada et al. | |
| 2010/0120115 A1* | 5/2010 | Ogle .................... | D01D 5/0038 435/177 |
| 2014/0065238 A1 | 3/2014 | Wolfinbarger, Jr. et al. | |
| 2014/0154663 A1 | 6/2014 | Wolfinbarger, Jr. et al. | |
| 2015/0010607 A1* | 1/2015 | Francis ................ | C12N 5/0654 435/402 |
| 2015/0017140 A1 | 1/2015 | Bhatia et al. | |
| 2015/0037434 A1* | 2/2015 | Freytes ................. | A61K 35/22 424/572 |
| 2017/0049932 A1* | 2/2017 | Badylak .............. | A61K 9/0014 |

FOREIGN PATENT DOCUMENTS

| | | |
|---|---|---|
| CN | 101848738 A | 9/2010 |
| CN | 102933705 A | 2/2013 |
| JP | 09503989 A | 4/1997 |
| JP | 2002226384 A | 8/2002 |
| JP | 2014506796 A | 3/2014 |
| WO | 2007129453 A1 | 11/2007 |
| WO | 2011132089 A2 | 10/2011 |
| WO | WO 2014/160002 A1 | 10/2014 |

OTHER PUBLICATIONS

Hagg et al The Journal of Cell Biology, vol. 142, 285-294 (Year: 1998).*
Butt et al. Journal of Proteome Research 5, 437-448 (Year: 2006).*
Piper et al Gut, 506-508 and (Year: 1965).*
Slivka et al Biomaterial Science, 1-3, 1-12 (Year: 2013).*
Wolf et al Biomaterials, 33, 29, 7028-7038 (Year: 2012).*
Miyamoto et al Journal of Cryogenic Biotechnology, 47-50, abstrac (Year: 2010).*
Sugiyama et al. Journal of Crystallograohic Society of Japan, 303-303, abstract (Year: 2012).*

(Continued)

*Primary Examiner* — Anoop K Singh
(74) *Attorney, Agent, or Firm* — RatnerPrestia

(57) ABSTRACT

The invention relates to placenta-derived matrix, methods of preparing, and methods of use thereof. The invention also relates to methods of culturing cells, delivering cells, promoting differentiation of stem cells or tissue-specific progenitor cells, and repairing, replacing, regenerating, filling, reducing or inhibiting scarring of defects using the same. The invention further relates to methods of coating placenta-derived matrix on a surface or injecting the placenta-derived matrix into a site of interest.

11 Claims, 5 Drawing Sheets

(56) References Cited

OTHER PUBLICATIONS

Kantsevoy et al. Gastrointestinal Endoscopy vol. 68, No. 1 : 1-18 (Year: 2008).*
Gilbert et al. Journal of Surgical Research, 152, 135-139 (Year: 2009).*
Piper et al. Gut, 6, 506-508 (Year: 1965).*
Fisher et al. J Biomed Mater Res. Nov. 1;71(2):268-74 (Year: 2004).*
Communication Pursuant to Article 94(3) for European Application No. 16 804 134.1, dated Apr. 1, 2020, 5 pages.
DeQuach et al., PLos One, 5(9):e13039, 12 pages.
European Search Report for European Application No. 16804134.1, dated Oct. 30, 2018 14 pages.
Francis et al., Acta Biomaterialia, 52:92-104 (2017).
Saldin et al., Acta Biomaterialia, 49:1-15 (2017).
Singelyn et al., Biomaterials 30(29):5409-16 (2009).
Wolf et al., Biomaterials 33(29):7028-38 (2012).
Notice of Reasons for Rejection for Japanese Application No. 2017-560956, dated May 12, 2020, with translation, 7 pages.
Notice of Reasons for Rejection for Japanese Application No. P2017-560956, dated Dec. 22, 2020, with translation, 10 pages.
Mutter, D., et al., "Biomaterial supports for colonic wall defect healing," 1996, vol. 17(14), pp. 1411-1415, Biomateriais.
Miyamoto, Y., et al., "Direct cryopreservation of primary hepatocytes and ES cells using a collagen vitrigel membrane," 2010, vol. 56(1), pp. 47-50, Journal of Cryogenic Biotechnology (Abstract only).
Sugiyama, S., et al., "Growth of protein crystals in hydrogels with high strength," 2012, vol. 54(5), pp. 300-303, Journal of the Crystallographic Society of Japan (Abstract only).
European Communication Pursuant to Article 94(3) for European Application No. 16804134.1, dated Dec. 8, 2020, 4 pages.
Chinese Office Action for Chinese Application No. 201880043795.1, dated Nov. 3, 2020, with translation, 12 pages.
Anson, J Gen Physiol, 22(1):79-89 (1938).
Ayres et al., J. Biomater. Sci. Polymer Edn., 19(5):603-21 (2008).
Corning® Matrigel® Matrix, 8 pages, 2013.
Flynn and Semple, Journal of Biomedical Materials Research Part A, 79(2):359-69 (2006).
Gilbert et al., J Surg Res., 152(1):135-39 (2009).
International Preliminary Report for International Application No. PCT/US2016/034712 dated Dec. 14, 2017.
Laughner et al., Am J Physiol Heart Circ Physiol., 303(7):H753-65 (2012).
PCT/US2016/034712 International Search Report issued by Lee W. Young (dated Aug. 22, 2016).
Notice of Reasons for Rejection for Japanese Application No. 2017-560956, dated Sep. 28, 2021, with translation, 14 pages.
European Communication pursuant to Article 94(3) for European Application No. 16 804 134.1, dated Nov. 30, 2021, 3 pages.

* cited by examiner

FIGURE 1

Proteins Identified in HuMATRIX by Hybrid Quadrapole Orbitrap Mass Spectrometry
*(multiple isoforms & types of)*

Extracellular Matrix-Related:
- Collagens
- Fibronectin
- Fibrinogen
- Elastin
- Laminin
- Nidogen
- Vitronectin
- Osteopontin
- Chondroitin Sulfate Proteoglycan
- Agrin
- HSPG
- GAGs
- Ficolin-2
- Serglycin
- Aggrecan

Growth Factors:
- VEGF-A & B
- PDGFs
- IGF-II
- HGF
- EGF, EGFL-7
- TGFs
- bFGF
- iFGF-12, -13

| ECM Protein | HuECM/Matrigel Ratio | Collagen Types in HuECM | Chains Identified |
|---|---|---|---|
| Collagen alpha-1(III) | 3.333 E9 | I | alpha-1(I) |
|  |  |  | alpha-2(I) |
| Fibronectin | 1.193 E8 | III | alpha-1(III) |
| Collagen alpha-1(XIV) | 1.687 E7 | IV | alpha-6(IV) |
|  |  | V | alpha-2(V) |
| Laminin alpha-2 | 8.907 E6 |  | alpha-3(V) |
| Collagen type I alpha-1 | 43.46 | VI | alpha-1(VI) |
|  |  |  | alpha-5(VI) |
| Laminin beta-2 | 0.2919 |  | alpha-6(VI) |
| Laminin gamma-1 | 0.0009 | XII | alpha-1(XII) |
|  |  | XVIII | alpha-1(XVIII) |
| Laminin alpha-5 | 3.094 E-8 | XIV | alpha-1(XIV) |
|  |  | XIX | alpha-1(XIX) |
| Nidogen-2 | 7.326 E-9 | XX | alpha-1(XX) |
| Fibrinogen-beta | 2.999 E-9 | XXVIII | alpha-1(XXVIII) |

PLACENTA-DERIVED MATRIX AND METHODS OF PREPARING AND USE THEREOF

CROSS-REFERENCE TO RELATED APPLICATION

This application is a U.S. national phase application of International Application No. PCT/US2016/034712, filed May 27, 2016, claiming the benefit of U.S. Provisional Application No. 62/168,397, filed May 29, 2015, the contents of each of which are incorporated herein by reference in their entireties for all purposes.

FIELD OF THE INVENTION

The invention relates generally to a matrix derived from placenta and methods of preparing and use thereof.

BACKGROUND OF THE INVENTION

Extracellular matrices (ECM) are essential for growing many cell types in culture and show therapeutic potential injected in animal disease models (e.g. cardiac ischemia). ECM may be prepared by various methods from animal tissues. Xenogeneic ECM may however elicit immune response or transmit xenozoonoses, limiting clinical utility. There remains a need of suitable ECM for clinical applications, for example, for therapeutic purposes, and biological studies.

SUMMARY OF THE INVENTION

The present invention relates to a placenta derived matrix and the methods for preparing or using the placenta derived matrix.

According to a first aspect of the present invention, a method of preparing a placenta-derived matrix is provided. The method comprises (a) decellularizing or devitalizing at least a piece of placenta tissue to produce a decellularized or devitalized placenta tissue, and (b) digesting the decellularized or devitalized placenta tissue in a digestion solution to produce a placenta-derived matrix.

The placenta-derived matrix may have a basic pH, for example, about 8.0 or above. The preparation method may further comprise adjusting the pH of the placenta-derived matrix to be 8.0 or more. The placenta-derived matrix may be substantially free (e.g., less than about 10, 0.1, 0.01 or 0.001 wt %) of collagenase. The placenta-derived matrix may consist essentially of the decellularized or devitalized placenta tissue and the digestion solution. The placenta tissue may be derived from a mammal, for example, human, bovine, porcine, murine, ovine, equine, canine and feline, preferably a human.

The decellularizing or devitalizing step may comprise treating the placenta tissue with a non-denaturing detergent. The non-denaturing detergent may be selected from the group consisting of N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester.

The preparation method may further comprise homogenizing the decellularized or devitalized placenta tissue concurrently with, before or after the digesting. The digesting may comprise homogenizing the decellularized or devitalized placenta tissue in the digestion solution. The decellularized or devitalized placenta tissue may be homogenized for 10 seconds to 72 hours. The decellularized or devitalized placenta tissue may be homogenized at 4° C. The preparation method may further comprise cutting the placenta tissue prior to the homogenizing, and only a part of the placenta tissue is homogenized.

In the preparation method, the placenta-derived matrix may be hydrogel, for example, thermoreversible hydrogel. The placenta-derived matrix may be thermoreversable hydrogel; and the solution-to-gel and/or gel-to-solution transition temperature of the thermoreversible hydrogel may be at a temperature from 4° C. to 40° C. The placenta-derived matrix may be thermoreversable hydrogel; and the thermoreversible hydrogel may gel at a temperature around 37° C.

In one embodiment, the preparation method does not include adding an additional crosslinking in addition to natural crosslinking from the placenta tissue. In another embodiment, the preparation method does not include adding an additional carrier in addition to natural carrier from the placenta tissue. In yet another embodiment, the preparation method does not include adding a photoactive agent. In a further embodiment, the preparation method does not include crosslinking the decellularized or devitalized placenta tissue and/or the placenta-derived matrix by non-naturally occurring bonds.

The preparation method may further comprise freezing or freeze-drying said placenta-derived matrix to produce a frozen or freeze-dried placenta-derived matrix.

The preparation method may further comprise placing the placenta-derived matrix in a mold having a predetermined shape, wherein the placenta-derived matrix is frozen or freeze-dried in the mold.

The preparation method may further comprise freezing or freeze-drying said placenta-derived matrix to produce a sponge structure, and optionally treating the sponge structure with a water replacing agent, wherein the frozen or freeze-dried placenta-derived matrix is stored in a wet state. The water replacing agent may comprise one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. The sponge structure may comprise pores having an average diameter from 1 µm to 4000 µm. An average void volume of the sponge structure may be from 10% to 95%.

The preparation method may further comprise freezing or freeze-drying said placenta-derived matrix to produce a sponge structure; dissolving the sponge structure in a solvent to produce a placenta-derived solution; and electrospinning the placenta-derived solution to produce nanofibers.

The preparation method may further comprise processing the sponge structure of the placenta-derived matrix under negative hydrostatic pressure to increase porosity.

The preparation method may further comprise electrospinning the placenta-derived matrix to produce nanofibers.

In the preparation method, the decellularized or devitalized placenta tissue may be digested at 37° C. The digestion solution may comprise pepsin, an acid or a combination thereof. The acid may be a strong acid such as hydrochloride (HCl). In one embodiment, the digestion solution comprises pepsin and HCl; the concentration of pepsin in the digestion solution is from 400 to 700 units/ml; and the concentration of HCl in the digestion solution is from 0.01 M to 1.0 M. The concentration of the decellularized or devitalized placenta tissue in the digestion solution may be from 0.1 to 40 mg/mL. The pepsin activity in the placenta-derived matrix may be less than about 10, 5, 1 or 0.1% of that in the digestion solution, when tested under an acidic pH (e.g., about 1.5-2.0), preferably at pH 2.0.

In the preparation method, the weight percentage of the placenta tissue in the decellularized or devitalized placenta tissue may be from 50% to 100% in the dry state. The weight percentage of the placenta tissue in the placenta-derived matrix may be from 50% to 100% in the dry state.

In the preparation method, the DNA quantity in the decellularized or devitalized placenta tissue may be reduced at least by 90% compared to the DNA quantity in the placenta tissue prior to the decellularizing or devitalizing step. The placenta-derived matrix may comprise no more than 10 μg, 1 μg, 500 ng, 200 ng or 100 ng DNA per mg of dry weight of the placenta-derived matrix.

The preparation method may further comprise storing the placenta-derived matrix prior to implanting. The placenta-derived matrix may be stored in a dry state. The placenta-derived matrix may be stored by cryopreservation.

The preparation method may further comprise treating said placenta-derived matrix with one or more treatment solutions. The treatment solution may comprise an ionic, enzymatic, or chemical crosslinking agent, a photoactive agent, or a polymer.

The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent may comprise one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid.

The preparation method may further comprise adding one or more bioactive supplement(s) to the decellularized or devitalized placenta tissue or the placenta-derived matrix. The one or more bioactive supplement(s) may be selected from a group consisting of a growth or differentiation factor of the FGF family, TGF-family, IGF-1, PDGF, EGF, VEGF, HGF, PTHrP, Ihh, dexamethasone, insulin, transferrin, selenium, ITS, and ascorbate.

The preparation method may further comprise adding one or more agent(s) that have bioactive supplement binding site(s) to the decellularized or devitalized placenta tissue and/or the placenta-derived matrix. The bioactive supplement binding site(s) may increase the affinity of growth factors, differentiation factors, cytokines, anti-microbial agents or anti-inflammatory agents to said placenta-derived matrix.

The preparation method may further comprise cleaning and disinfecting the placenta tissue.

The preparation method may further comprise sterilizing the placenta tissue and/or the decellularized or devitalized placenta tissue.

The preparation method may further comprise decellularizing the at least a piece of placenta tissue to produce a decellularized placenta tissue.

The preparation method may further comprise adding one or more bone fragment material(s) to the placenta-derived matrix. The bone fragments material(s) may comprise one or more selected from the group consisting of non-demineralized bone, partially demineralized bone, demineralized bone, ceramics, hydroxyapatite, calcium phosphate, calcium sulfate, and calcium carbonate.

For each preparation method of the present invention, a placenta-derived matrix prepared by the method is provided.

A method of cell culture is provided. The method comprises culturing cells on or in the placenta-derived matrix prepared by the preparation method of the present invention. The cells may be selected from the group consisting of stem cells, adipose derived stem cells, dorsal root ganglion cells, pancreatic islet cells, cardiomyocytes, hepatocytes, iPSCs, cancer cells, and umbilical vein endothelial cells. The method may further comprise storing the cells on or in the placenta-derived matrix. The cells on or in the placenta-derived matrix may be stored by cryopreservation.

A method of inhibiting and/or reducing loss of biological activity of a protein due to freezing or lyophilization is provided. The method comprises exposing the protein to the placenta-derived matrix prepared by the method of the present invention in an effective amount sufficient to inhibit or reduce loss of biological activity of a protein due to freezing or lyophilization.

A method of cell delivery is provided. The method comprises mixing cells in the placenta-derived matrix prepared by the method of the present invention to produce a mixture of the cells and the placenta-derived matrix, and injecting the mixture into a site of interest.

A method of cell delivery is provided. The method comprises culturing cells on or in the placenta-derived matrix prepared by the method of the present invention to produce a culture of the cells and the placenta-derived matrix, and injecting the culture into a site of interest. The site of interest may be in a subject in need of cell delivery.

A method of promoting differentiation of pluripotent stem cells or tissue-specific progenitor cells is provided. The method comprises culturing the pluripotent stem cells or tissue-specific progenitor cells on or in the placenta-derived matrix prepared by the method of the present invention. The pluripotent stem cells may be cultured on or in the placenta-derived matrix without adding a growth factor or another secondary factor to induce the differentiation of the pluripotent stem cells, and the differentiation of the pluripotent stem cells is increased. The pluripotent stem cells or tissue-specific progenitor cells may be cultured with an addition of one or more growth factors or other secondary factors to induce the maintenance or differentiation of the cells. The pluripotent stem cells or tissue-specific progenitor cells may be differentiated into osteoblasts, chondrocytes, cardiomyocyte, pancreatic cells, neuronal cells, ligament or tendon. The pluripotent stem cells may be adult stem cells. The pluripotent stem cells or tissue-specific progenitor cells may be derived from embryos, placenta, bone marrow, adipose tissue, blood vessel, amniotic fluid, synovial fluid, synovial membrane, pericardium, periosteum, dura, peripheral blood, umbilical blood, placental membrane, menstrual blood, teeth, nucleus pulposus, brain, neonatal foreskin, skin, hair follicle, intestinal crypt, neural tissue, liver, pancreas, or muscle. The pluripotent stem cells may be pluripotent stem cells or iPSCs. The pluripotent stem cells may be selected from the group consisting of adipose derived stem cells and dental pulp stem cells.

A method of promoting vascular, myogenic, or neurogenic differentiation of pluripotent stem cells or tissue-specific progenitor cells is provided. The method comprises culturing the pluripotent stem cells or tissue-specific progenitor cells on or in the placenta-derived matrix prepared by the method of the present invention. The pluripotent stem cells may be adult stem cells. The pluripotent stem cells or tissue-specific progenitor cells may be derived from embryos, placenta, bone marrow, adipose tissue, blood vessel, amniotic fluid, synovial fluid, synovial membrane, pericardium, periosteum, dura, peripheral blood, umbilical blood, placental membrane, menstrual blood, teeth, nucleus pulposus, brain, neonatal foreskin, skin, hair follicle, intestinal crypt, neural tissue, or muscle. The pluripotent stem cells or tissue-specific progenitor cells may be pluripotent stem cells or iPSCs.

A method of increasing maintenance of self-renewing ability of the tissue-specific progenitor cells is provided. The method comprises culturing the tissue-specific progenitor cells on or in the placenta-derived matrix prepared by the method of the present invention. In one embodiment, a growth factor or another secondary factor to induce the maintenance of the tissue-specific progenitor cells is not added.

A method of reducing or repairing a defect in a tissue is provided. The method comprises implanting the placenta-derived matrix prepared by the method of the present invention at the site of defect. The implanting may be performed by painting, airbrushing, dripping, or injecting the placenta-derived matrix to the site of defect. The tissue may be heart, liver, pancreas, bone, cartilage, or soft tissue. The method may further comprise seeding vital cells on or in said placenta-derived matrix to render said placenta-derived matrix vital. The method may further comprise seeding vital cells on or in said placenta-derived matrix to render said placenta-derived matrix vital; and culturing said cell-seeded placenta-derived matrix before implantation. The method may exclude hydration of the placenta-derived matrix prior to implanting to allow said placenta-derived matrix to absorb blood, fluid, and/or autologous cells in situ. The method may further comprise hydrating the placenta-derived matrix with a hydrating solution; optionally seeding vital cells on or in said placenta-derived matrix to render said placenta-derived matrix vital; and optionally culturing said cell-seeded placenta-derived matrix before implantation. The hydrating solution may comprise one or more selected from the group consisting of blood or bone marrow aspirate, platelet rich plasma, synovial fluid, enzymes, bioactive supplements, natural polymers, synthetic polymers, photoactive agents, antioxidants, crosslinking agents, antimicrobial agents, vital cells, and one or more agents that have bioactive supplement binding site(s). The vital cells may comprise one or more selected from the group consisting of cells from autologous or allograft bone marrow aspirate; stromal cells from bone marrow; stromal cells from fat, synovium, periostieum, perichondrium, muscle, dermis, umbilical cord blood, and Warton's jelly; and pericytes.

A method of marking a tissue part of interest is provided. The method comprises implanting the placenta-derived matrix prepared by the method of the present invention underneath a tissue part of interest.

A method of resecting a tissue is provided. The method comprises implanting the placenta-derived matrix prepared by the method of the present invention underneath a tissue part of interest, and resecting the tissue part above the placenta-derived matrix. The implanting may be performed by painting, airbrushing, dripping, or injecting the placenta-derived matrix to the site of defect. The tissue may be sessile or flat neoplasms of a GI tract. The method may further comprises cutting the mucosa after implanting the placenta-derived matrix, dissecting the tissue, and lifting the tissue away from the remaining GI tract.

According to a second aspect of the present invention, a placenta-derived matrix comprising decellularized or devitalized placenta tissue, and the placenta-derived matrix has a basic pH of, for example, 8.0 or more. The placenta-derived matrix may be substantially free (e.g., less than about 10, 0.1, 0.01 or 0.001 wt %) of collagenase. The placenta-derived matrix may consist essentially of the decellularized or devitalized placenta tissue.

The placenta-derived matrix may be hydrogel, for example, thermoreversible hydrogel. In one embodiment, the placenta-derived matrix is thermoreversable hydrogel; and the solution-to-gel transition temperature of the thermoreversible hydrogel is at a temperature from 4° C. to 40° C. In another embodiment, the placenta-derived matrix is thermoreversable hydrogel; and the thermoreversible hydrogel gels at a temperature around 37° C.

The placenta-derived matrix may comprise a sponge structure. The placenta-derived matrix may comprise nanofibers. The weight percentage of the placenta tissue in the placenta-derived matrix may be from 50% to 100% in the dry state. The decellularized or devitalized placenta tissue may be derived from a mammal, for example, human, bovine, porcine, murine, ovine, equine, canine and feline, preferably a human. The placenta-derived matrix may comprise no more than 10 µg, 1 µg, 500 ng, 200 ng or 100 ng DNA per mg of dry weigh of the placenta-derived matrix. The placenta-derived matrix may comprise type I collagen, type IV collagen, laminin gamma-1, fibronectin, chroionic sommatomammotropin, FGF-12, FGF-13, IGF-2, EGFL-7, and bFGF, wherein the concentration of the type I collagen in the placenta-derived matrix is more than 35%.

A method of cell culture is provided. The method comprises culturing cells on or in the placenta-derived matrix of the present invention.

A method of inhibiting and/or reducing loss of biological activity of a protein due to freezing or lyophilization is provided. The method comprises exposing the protein to the placenta-derived matrix of the present invention in an effective amount sufficient to inhibit or reduce loss of biological activity of a protein due to freezing or lyophilization.

A method of cell delivery is provided. The method comprises mixing cells in the placenta-derived matrix of the present invention to produce a mixture of the cells and the placenta-derived matrix, and injecting the mixture into a site of interest.

A method of cell delivery is provided. The method comprises culturing cells on or in the placenta-derived matrix of the present invention to produce a culture of the cells and the placenta-derived matrix, and injecting the culture into a site of interest.

A method of promoting differentiation of pluripotent stem cells or tissue-specific progenitor cells is provided. The method comprises culturing the pluripotent stem cells or tissue-specific progenitor cells on or in the placenta-derived matrix of the present invention.

A method of promoting vascular, myogenic, or neurogenic differentiation of pluripotent stem cells or tissue-specific progenitor cells is provided. The method comprises culturing the pluripotent stem cells or tissue-specific progenitor cells on or in the placenta-derived matrix of the present invention.

A method of increasing maintenance of self-renewing ability of the tissue-specific progenitor cells is provided. The method comprises culturing the tissue-specific progenitor cells on or in the placenta-derived matrix of the present invention.

A method of reducing or repairing a defect in a tissue is provided. The method comprises implanting the placenta-derived matrix of the present invention at the site of defect.

A method of marking a tissue part of interest is provided. The method comprises implanting the placenta-derived matrix of the present invention underneath a tissue part of interest.

A method of resecting a tissue is provided. The method comprises implanting the placenta-derived matrix of the present invention underneath a tissue part of interest, and resecting the tissue part above the placenta-derived matrix.

According to a third aspect of the present invention, a method of coating placenta-derived matrix on a surface of a substrate is provided. The method comprises: (a) decellularizing or devitalizing at least a piece of placenta tissue to produce a decellularized or devitalized placenta tissue, (b) digesting the decellularized or devitalized placenta tissue in a digestion solution to produce a placenta-derived matrix, and (d) coating at least a part of a surface of a substrate with the placenta-derived matrix. The placenta-derived matrix may have a basic pH before coating. The coating method may further comprise adjusting the pH of the placenta-derived matrix to be basic, for example, a pH of 8.0 or more, before coating. The placenta-derived matrix may be substantially free (e.g., less than about 10, 0.1, 0.01 or 0.001 wt %) of collagenase. The placenta-derived matrix may consist essentially of the decellularized or devitalized placenta tissue and the digestion solution. The placenta tissue may be from a mammal, for example, human, bovine, porcine, murine, ovine, equine, canine and feline, preferably a human.

The coating method may further comprise electrospinning the placenta-derived matrix on the surface.

The coating method may further comprise homogenizing the placenta tissue concurrently or prior to the digesting. The digesting may comprise homogenizing the decellularized or devitalized placenta tissue in the digestion solution. The homogenizing may be performed for 10 seconds to 72 hours. The homogenizing may be performed at 4° C.

The coating method may further comprise cutting the placenta tissue prior to the homogenizing, and only a part of the placenta tissue is homogenized.

Where the placenta-derived matrix is hydrogel, the coating method may further comprise gelling the placenta-derived matrix on the surface. In one embodiment, the placenta-derived matrix is thermoreversable hydrogel; and the solution-to-gel transition temperature of the thermoreversible hydrogel is at a temperature from 4° C. to 40° C. In another embodiment, the placenta-derived matrix is thermoreversable hydrogel; and the thermoreversible hydrogel gels at a temperature around 37° C.

In one embodiment, the coating method does not include adding an additional crosslinker in addition to natural crosslinker from the placenta tissue. In another embodiment, the coating method does not include adding an additional carrier in addition to the natural carrier from the placenta tissue. In yet another embodiment, the coating method does not include adding a photoactive agent. In a further embodiment, the coating method does not include crosslinking the placenta tissue or the decellularized or devitalized placenta tissue by non-naturally occurring bonds.

In the coating method, the digestion solution may comprise pepsin, HCl or a combination thereof. In one embodiment, the digestion solution comprises pepsin and HCl; the concentration of pepsin is from 400 to 700 units/ml; and the concentration of HCl is from 0.01 M to 1.0 M.

In the coating method, the concentration of the decellularized or devitalized placenta tissue in the digestion solution may be from 5 to 50 mg/mL. The weight percentage of the placenta tissue in the decellularized or devitalized placenta tissue may be from 50% to 100% in the dry state. The weight percentage of the placenta tissue in the placenta-derived matrix may be from 50% to 100% in the dry state.

In the coating method, the DNA quantity in the decellularized or devitalized placenta tissue may be reduced at least by 90% compared to the DNA quantity in the placenta tissue prior to the decellularizing step. The placenta-derived matrix may comprise no more than 10 μg, 1 μg, 500 ng, 200 ng or 100 ng DNA per mg of the placenta-derived matrix.

The coating method may further comprise storing the substrate prior to implanting. The substrate may be stored in a dry state. The substrate may be stored by cryopreservation.

The coating method may further comprise treating said placenta-derived matrix with one or more treatment solutions before or after the coating. At least one of said one or more treatment solutions may comprise an ionic, enzymatic, or chemical crosslinking agent, a photoactive agent, or a polymer. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent may comprise one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid.

The coating method may further comprise adding one or more bioactive supplement(s) to the decellularized or devitalized placenta tissue and/or the placenta-derived matrix before or after the coating. The one or more bioactive supplement(s) may be selected from a group consisting of a growth or differentiation factor of the FGF family, TGF-family, IGF-1, PDGF, EGF, VEGF, HGF, PTHrP, Ihh, dexamethasone, insulin, transferrin, selenium, ITS, or ascorbate.

The coating method may further comprise adding one or more agent(s) that have bioactive supplement binding site(s) to the decellularized or devitalized placenta tissue and/or the placenta-derived matrix. The bioactive supplement binding site(s) may increase the affinity of growth factors, differentiation factors, cytokines, anti-microbial agents or anti-inflammatory agents to said placenta-derived matrix.

The coating method may further comprise cleaning and disinfecting the placenta tissue. The coating method may further comprise sterilizing the placenta tissue and/or the decellularized or devitalized placenta tissue. The coating method may further comprise decellularizing the placenta tissue. The coating method may further comprise processing the placenta-derived matrix under negative hydrostatic pressure to increase porosity.

For each coating method of the present invention, a scaffold produced by the method is provided.

For each coating method of the present invention, a surface coated with the placenta-derived matrix produced by the method is provided.

For each coating method of the present invention, a method of cell culture is provided. The method of cell culture comprises culturing cells on a cell culture surface coated with the placenta-derived matrix produced by the coating method.

BRIEF DESCRIPTION OF THE DRAWINGS

FIG. 1 depicts Mass Spectrometry Relative Abundance Data. The amount of the major ECM proteins found in placenta derived matrix samples relative to MATRIGEL® are shown by relative abundance as determined by orbitrap mass spectrometry, along with a list of all collagen isoforms (chains) thus far identified in placenta derived matrix samples.

DETAILED DESCRIPTION OF THE INVENTION

Figure 2:
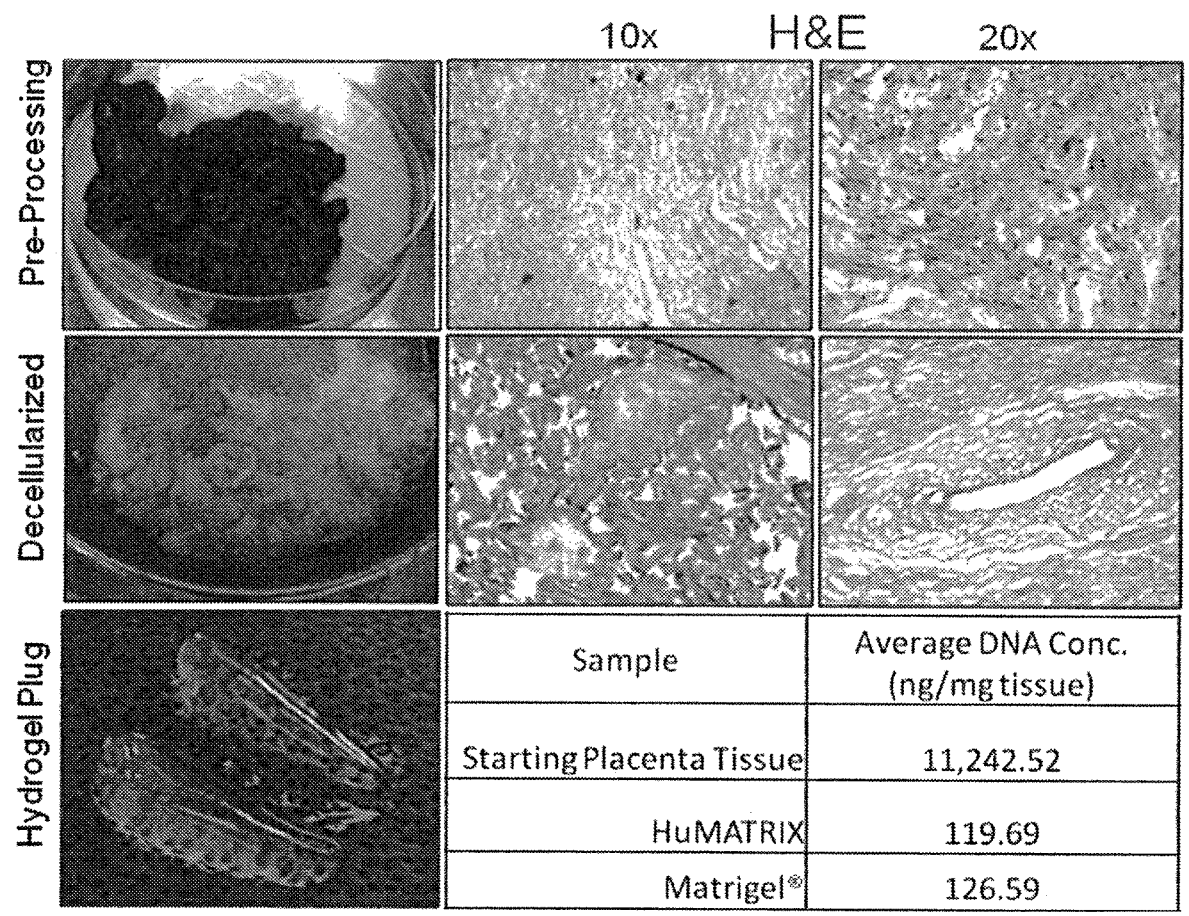
FIG. 2 depicts residual DNA present in placenta-derived matrix samples HuMATRIX and MATRIGEL®. To quantitative the amount of residual DNA present in placenta derived matrix samples, a pico green assay was conducted. The starting placenta tissue, HuMATRIX and MATRIGEL® had an average DNA concentration of 11,242.52, 119.69 and 126.59 ng per mg tissue or matrix (ng/mg tissue), respectively, and showed approximate 95% reduction in DNA relative to starting tissue. This was confirmed by histology sections of the placenta-derived matrix tissue as stained by H&E.

Towards advancing clinical applications of extracellular matrices (ECM) for therapeutic purpose, placenta-derived matrices have been prepared and their ECM have been proteomically evaluated, for example, for novel in vivo delivery and for supporting xeno-free, serum-free somatic and stem cell cultures. It has been discovered that placenta-derived matrices having a basic pH provides improvement over those having a neutral pH. For example, a basic pH inactivates digestive enzymes such as pepsin irreversibly and provides precise control of digestion of tissues to make ECM. In addition, a basic pH provides the ECM better gelling properties, for example, more homogenous ECM. Further, ECM having a basic pH exhibit better cellular functions, for example, better cell attachments. It has also been discovered that a placenta-derived matrix in the form of an extracted solution, a hydrogel or other reconstituted scaffolds that is prepared by a decellularizing or devitalizing process involving treating a placenta tissue with one or more non-denaturing detergents may maintain substantially the biological functions of the placenta tissue.

The present invention provides placenta-derived matrices, methods of preparing, and methods of use thereof. The invention also provides methods of culturing cells, delivering cells, promoting differentiation of stem cells or tissue-specific progenitor cells, and repairing, replacing, regenerating, filling, reducing or inhibiting scarring of defects using the placenta-derived matrices. The invention further provides methods of coating a placenta-derived matrix on a surface or injecting the placenta-derived matrix into a site of interest.

In one aspect, the invention relates to methods of preparing a placenta-derived matrix. The methods comprise decellularizing or devitalizing a placenta tissue to produce a decellularized or devitalized placenta tissue, and digesting the decellularized or devitalized placenta tissue in a digestion solution to produce a placenta-derived matrix.

The term "placenta-derived matrix" as used herein refers to an extracellular matrix prepared from a placenta tissue. The placenta-derived matrix may retain a substantial amount (e.g., at least about 70, 80, 90, 95, 99%, 99.9% or 99.999%) of the extracellular molecules (e.g., proteins, polysaccharides and proteoglycans) in the placenta tissue. Preferably, the placenta-derived matrix comprises no viable cell. The placenta-derived matrix may be substantially free (e.g., less than about 10, 0.1, 0.01 or 0.001 wt %) of one or more molecules (e.g., collagenase and endotoxin) in the placenta tissue.

The placenta-derived matrix may have a basic pH. The preparation method may further comprise adjusting the pH of the placenta-derived matrix produced by the digestion of the decellularized or devitalized placenta tissue to be basic, for example, about 8.0 or more, preferably about 8.2.

The term "basic pH" as used herein refers to a pH above about 7.8. A basic pH may be in the range of about 8.0-11.0, preferably about 8.0-9.0, more preferably about 8.0-8.2. For example, a basic pH may be about 7.9, 8.0, 8.1, 8.2, 8.3, 8.4, 8.5, 8.6, 8.7, 8.8, 8.9 or 9.0. Preferably, the basic pH is about 8.2.

The term "neutral pH" as used herein refers to a pH of about 6.0-7.8, preferably about 6.5-7.5, more preferably about 6.8-7.2. For example, a neutral pH may be about 6.5, 6.6, 6.7, 6.8, 6.9, 7.0, 7.1, 7.2, 7.3, 7.4, 7.5, 7.6, 7.7 or 7.8. Preferably, a neutral pH is about 7.4.

The term "acidic pH" as used herein refers to a pH below about 5.0. An acidic pH may be in the range of about 1.0-5.0, preferably about 1.0-4.0, more preferably about 1.5-2.0. For example, an acidic pH may be about 1.0, 1.5, 2.0, 2.5, 3.0, 3.5 or 4.0. Preferably, the acidic pH is about 2.0.

The term "decellularizing" as used herein refers to a process for reducing a substantial amount by, for example, at least about 70, 80, 90, 95, 99, 99.9 or 99.999% of the intact cells in a tissue, for example, a placenta tissue.

The term "devitalizing" as used herein refers to a process for reducing a substantially amount by, for example, at least about 70, 80, 90, 95, 99, 99.9 or 99.999% of the viable cells in a tissue, for example, a placenta tissue. Preferably, the placenta-derived matrix comprises no viable cell.

The placenta tissue may be from a mammal. The mammal may be a human, bovine, porcine, murine, ovine, equine, canine or feline. Preferably, the placenta tissue is a human placenta tissue. In one embodiment, the placenta-derived matrix does not to induce an immune response in a subject when the placenta-derived matrix is introduced to a human by, for example, implantation.

The decellularizing or devitalizing process described herein remove cellular components from the piece of placenta tissue. The decellularizing or devitalizing process described herein may be performed in accordance with the methods described in U.S. Pat. Nos. 6,734,018, 7,338,757, 8,574,826, 6,743,574, and 8,563,232, and U.S. Patent Application Publication No. 2014/0065238A1 and 2014/0154663A1, each of which is incorporated by reference herein in its entirety. The decellularizing devitalizing process may not include using detergent, endonuclease, or protease. The decellularizing or devitalizing process may be performed without damage to matrix and/or tissue structure of the placenta tissue and may employ detergents, sarcosinates, endonuclease, and decontaminating agents. The detergent may be any detergent suitable for decellularizing or devitalizing a tissue, preferably a placenta tissue, more preferably a human placenta tissue. In some embodiments, a devitalized placenta tissue is produced by devitalizing a placenta tissue using a detergent, preferably a non-denaturing detergent. The non-denaturing detergent may be selected from the group consisting of N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester. The detergent is preferably not anionic detergents or denaturing detergents, for example, SDS.

The matrix structure may include collagens, hyaluronins, elastins, mucopolysaccharides and proteoglycans, among other components. In some embodiments, the placenta-derived matrix may comprise more than one type of collagen and/or more than one proteins, other than collagen, collagen type I, and/or collagen type IV. At least about 50, 60, 70, 80, 90, 95 or 99 wt % of EMC proteins (e.g., collagen I, collagen IV, fibronectin, laminins, and placental lactogen) in the placenta tissue prior to decellularizing or devitalizing process may remain in the resulting placenta-derived matrix.

In some embodiments, the DNA quantity in the decellularized or devitalized placenta tissue is reduced by 60, 70, 80, 85, 90, 95, 99% or more; 60, 70, 80, 85, 90, 95, 99, 100% or less; and/or between 50 and 100%, between 70 and 100%, between 90 and 100%, between 90 and 95% compared to the DNA quantity in the placenta tissue prior to the decellularizing or devitalizing process. In other embodiments, the placenta-derived matrix comprises no more than 10 µg, 1 µg, 500 ng, 200 ng or 100 ng DNA per mg of dry weight of the placenta-derived matrix.

In additional embodiments, the placenta tissue described herein is an autograft, an allograft, or a xenograft. In additional embodiments, the placenta tissue herein may have human, non-human animal, bovine, equine, porcine, ovine, caprine, or piscine origins, among others. In further embodiments, the placenta tissue described herein may be (i) a whole, complete placenta having plate, amnion and chorion, or (ii) a part of the placenta tissue excluding aminion and/or chorion. Placenta tissue may also be the product of biotechnological methods, for example, tissue engineered placenta tissue produced using cell culture methods, and such a product of biotechnological methods may be included as the placenta tissue described herein.

The methods of preparing a placenta-derived matrix according to some embodiments of the present invention comprise digesting the decellularized or devitalized placenta tissue in a digestion solution to produce a placenta-derived matrix. The digestion solution described herein may include an enzyme to digest at least a part of proteins in the placenta tissue. For example, the digestion solution may comprise an acid, a strong or weak acid, and a protease including, but not limited to, papain, pepsin, pepsinogen, trypsin, collagenases, and/or dispase. The acid may be selected from the group consisting of hydrochloride (HCl), nitric acid (HNO3), acetic acid ($HC_2H_3O_2$), citric acid ($H_3C_6H_5O_7$, sulfuric acid ($H_2SO_4$) and trifluoroacetic acid ($CF_3CO_2H$). Preferably, the acid is HCl. As used herein, the term "and/or" includes any and all combinations of one or more of the associated listed items.

In some embodiments, the concentration of the pepsin in the digestion solution may be about 300, 400, 500, 600, 700, 800, 1000, 5000 or 8000 units/ml or less; about 100, 200, 300, 400, 500, 600, 700, 800, 1000, 5000 or 6000 units/ml or more; and/or about from 100 to 8000, from 200 to 1000, from 400 to 700, from 100 to 600, from 400 to 1000, from 300 to 600, or from 500 to 600 units/ml. The pepsin activity in the placenta-derived matrix may be less than about 10, 5, 1 or 0.1% of that in the digestion solution, when tested at a suitable acidic pH, for example, about 2.0.

In additional embodiments, the concentration of the acid (e.g. HCl) in the digestion solution may be about 0.005, 0.002, 0.005, 0.02, 0.2, 0.3, 0.4, 0.6, 0.8, 1.0 M or less; about 0.0001, 0.0005, 0.001, 0.005, 0.01, 0.15, 0.2, 0.3, 0.5, 0.7 M or more; and/or about from 0.0005 to 1.0 M, 0.01 to 0.2 M, from 0.001 to 0.5 M, from 0.02 to 0.2, from 0.02 to 0.1, from 0.01 to 0.1, or from 0.0001 to 0.5 M. In further embodiments, the concentration of the decellularized or devitalized placenta tissue in the digestion solution may be about 0.01, 0.1, 0.5, 1, 5, 10, 20, 30, 40, 50 mg/mL or less; about 0.01, 0.1, 0.5, 1, 5, 10, 20, 30, 40, 50 mg/mL or more; and/or about from 0.1 to 40, from 1 to 50, from 10 to 40, from 0.01 to 100, or from 10 to 100 mg/mL. In additional embodiments, the placenta tissue and/or decellularized or devitalized placenta tissue is digested for about 5 seconds, 10 seconds, 15 seconds, 20 seconds, 25 seconds, 30 seconds, 40 seconds, 50 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or more. In additional embodiments, placenta tissue and/or decellularized or devitalized placenta tissue is digested for about 20 seconds, 30 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or less. In further embodiments, placenta tissue and/or decellularized or devitalized placenta tissue is digested for between about 20 seconds and 72 hours, about 1 minute and 20 minutes, about 1 minute to 10 minutes, or about 1 minute to 6 minutes.

The methods of preparing a placenta-derived matrix according to some embodiments of the present invention further comprise homogenizing the decellularized or devitalized placenta tissue concurrently with, before or after the digesting to produce a placenta-derived matrix comprising homogenized placenta tissue or placenta tissue homogenate. In some embodiments, the digesting comprises homogenizing the decellularized or devitalized placenta tissue in the digestion solution. Homogenized placenta tissue or placenta tissue homogenate contain at least a piece of decellularized or devitalized placenta tissue that has been reduced to particles that are smaller and/or evenly distributed compared to the tissue or tissue pieces prior to the homogenizing. Homogenized placenta tissue may optionally include at least one of water, aqueous solutions, or water miscible polar organic solvents, in addition to the particles. The homogenized placenta tissues used in methods of the present invention include particles having an average diameter of less than about 100 microns. In some embodiments, the homogenized placenta tissue may be prepared by shear-induced shredding of a composition comprising placenta tissue, and optionally, at least one of water, an aqueous solution and a water miscible polar organic solvent. A conventional blender may be used in preparing the homogenized placenta tissue, in certain embodiments. In some embodiments, the placenta tissue may be homogenized mechanically by chopping, skiving, milling (including cryo-milling), grinding, slicing and/or beating the soft tissue (e.g. by a blender, a beater, and a mixer). For example, the placenta tissue described herein may be mechanically modified at about 1,000, 5,000, 10,000, or 15,000 rpm and a maximum shear speed of a commercially available blender by blender for about 1, 3, or 5 minutes. In additional embodiments, the placenta tissue and/or decellularized or devitalized placenta tissue is homogenized for about 5 seconds, 10 seconds, 15 seconds, 20 seconds, 25 seconds, 30 seconds, 40 seconds, 50 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or more. In additional embodiments, placenta tissue and/or decellularized or devitalized placenta tissue is homogenized for about 20 seconds, 30 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or less. In further embodiments, placenta tissue and/or decellularized or devitalized placenta tissue is homogenized for between about 20 seconds and 72 hours, about 1 minute and 20 minutes, about 1 minute to 10 minutes, or about 1 minutes to 6 minutes.

In some embodiments, the digesting and/or homogenizing may be performed at about −200, −100, −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36 or 37° C.; below about −70, −60, −50, −40, −30, −20, −10, −5, 0, 5, 10, 15, 16, 17, 18, 19, 20, 21, 22, 23, 24, 25, 26, 27, 28, 29, 30, 31, 32, 34, 35, 36, 37, 38 or 39° C.; above about −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36, or 37° C.; and/or between about −80 and about 37° C., −80 and about 25° C., −80 and about 38° C., −70 and about 38° C., about −50 and about 38° C., about −30 and about 38° C., about −10 and about 38° C., about 0 and about 38° C., about 5 and about 38° C., about 10 and about 38° C., about 15 and about 38° C., about −5 and about 10° C., about −5 and about 5° C., or about 0 and about 10° C. In additional embodiments, the methods described herein may exclude treating the placenta tissue or decellularized and/or devitalized placenta tissue with heat above about 24, 25, 26, 27, 28, 29, 30, 31, 32, 33, 35, 36, 37, 38, 40, 45, 50, 60, 70, 80, 90, 100, 150, or 200° C. prior to, during and/or after the digesting and/or homogenizing. In some embodiments, the method excludes treating the placenta tissue or decellularized and/or devitalized placenta tissue with heat below about 50, 70, 90, 110, 200, or 300° C. prior to, during, and/or after the digesting and/or homogenizing. In other embodiments, the method excludes treating the placenta tissue or decellularized and/or devitalized placenta tissue with heat between about 26 and about 200° C., about 30 and about 150° C., about 39 and about 300° C., about 40 and about 120° C., about 50 and about 110° C., and about 50 and about 100° C., about 50 and about 300° C. prior to, during, and/or after the digesting and/or homogenizing. In another aspect, the method may exclude sonication, microwave irradiation, or conventional heat transfer from a heating component, among other methods known in the art.

In another aspect, the placenta-derived matrix described herein may be in a form of hydrogel. As used herein, the term hydrogel has its art understood meaning and refers to a water-swellable polymeric matrix that can absorb water to form gels of varying elasticity. The term "matrix" refers to a three-dimensional network of macromolecules held together by covalent and/or non-covalent crosslinks. On placement in an aqueous environment, dry hydrogels may swell to the extent allowed by the degree of cross-linking. The amount of water absorbed can be controlled by the macromolecule component used. In some embodiments, the placenta-derived matrix described herein is in a form of thermoreversible hydrogel. The thermoreversible hydrogel described herein means a temperature-sensitive gel which changes its order depending on the temperature. In additional embodiments, the solution-to-gel transition temperature of the thermoreversible hydrogel is at a temperature from about 4° C. to about 40° C., from about 10° C. to about 40° C., from about 20° C. to about 40° C., from about 30° C. to about 40° C., from about 35° C. to about 40° C., from about 36° C. to about 38° C., or from about 20° C. to about 38° C. The solution-to-gel transition temperature of the thermoreversible hydrogel may be at a temperature at about 5, 10, 20, 25, 30, 31, 32, 33, 34, 35, 36, 37, 38, 39, 40, 41, 42, 43, 44, 45, 50, 60° C. or less. The solution-to-gel transition temperature of the thermoreversible hydrogel may be at a temperature at about 3, 5, 10, 20, 25, 30, 31, 32, 33, 34, 35, 36, 37, 38, 39, 40, 41, 42, 43, 44, 45, 50, 60° C. or more. In further embodiments, the gel-to-solution transition temperature of the thermoreversible hydrogel is at a temperature from about −1° C. to about 4° C., from about 0° C. to about 10° C., from about 5° C. to about 15° C., from about 4° C. to about 40° C., from about 10° C. to about 40° C., from about 20° C. to about 40° C., from about 30° C. to about 40° C., or from about 35° C. to about 40° C. The gel-to-solution transition temperature of the thermoreversible hydrogel may be at a temperature at about 4, 5, 6, 7, 8, 9, 10, 11, 12, 13, 14, 15, 20, 25, 30, 31, 32, 33, 34, 35, 36, 37, 38, 39, 40, 41, 42, 43, 44, 45° C. or less. The gel-to-solution transition temperature of the thermoreversible hydrogel may be at a temperature at about −1, 0, 1, 2, 3, 4, 5, 6, 7, 8, 9, 10, 11, 12, 20, 25, 30, 31, 32, 33, 34, 35, 36, 37, 38, 39, 40° C. or more.

In another aspect, the methods described herein do not include adding (i) an additional crosslinking in addition to natural crosslinking from the placenta tissue, (ii) an additional carrier in addition to natural carrier from the placenta tissue, and/or (iii) a photoactive agent to the decellularized or devitalized placenta tissue and/or placenta-derived matrix. In another aspect, the decellularized or devitalized placenta tissue and/or placenta-derived matrix may or may not comprise an additional crosslinker or carrier in addition to a natural crosslinker(s) and a natural carrier(s) from the one or more placenta tissue(s). The methods, however, may add the additional crosslinker or carrier in addition to a natural crosslinker(s) and a natural carrier(s) from the one or more placenta tissue(s) after digesting and/or homogenizing the placenta tissue, and the placenta-derived matrix may comprise the additional crosslinker or carrier described below, in addition to a natural crosslinker(s) and a natural carrier(s) from the placenta tissue(s).

The placenta tissue described herein may comprise a naturally occurring crosslinker that is configured to create a physical and/or chemical bond at least between two parts of the placenta tissue before or after digesting, homogenizing, harvesting, dispersing, freezing, and/or freeze-drying the placenta tissue. The chemical bonds may include ionic, covalent, and/or metallic bonds. For example, natural crosslinkers of the placenta tissue may be crosslinked to form a physical and/or chemical bond by a chemical, physical, and/or temperature treatment after digesting and/or homogenizing the placenta tissue. In some embodiments, the methods described herein do not include crosslinking the decellularized or devitalized placenta tissue and/or placenta-derived matrix by non-naturally occurring bonds using non-naturally occurring crosslinkers.

In some embodiments, the decellularized or devitalized placenta tissue and/or placenta-derived matrix described herein may exclude a non-naturally occurring crosslinker, also called as crosslinking agent herein. In additional embodiments, the digested placenta tissue described herein does not comprise a non-naturally occurring crosslinker. For example, the decellularized or devitalized placenta tissue and/or placenta-derived matrix described herein may exclude a non-naturally occurring crosslinker selected from the group consisting of propylene glycol alginate, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC), dimethyl suberimidate (DMS), dimethyl-3-3'-dithiobispropionimidate (DTBP), acryl azide, and a combination thereof. In additional embodiments, the placenta-derived matrix described herein may exclude a photoactive agent selected from the group consisting of a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis (3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dye, ethyl eosin, eosin Y, and a combination thereof.

In another aspect, the placenta tissue described herein may also comprise a natural carrier. The carriers described herein are configured to form a three-dimensional framework to be injected or implanted into wound, defect, and/or surgical sites. In some embodiments, the wound may be an open wound or tunnel wound. The natural carriers are carriers that naturally occur in a placenta tissue, and, for example, include extracellular matrices, such as collagen and hyuronic acid or elastin. In some embodiments, the homogenized and/or digested placenta tissue and/or biologically functional scaffold described herein may exclude a non-naturally occurring carrier selected from the group consisting of gelatin, agarose, modified hyaluronic acid, propylene glycol alginate, polyethylene glycol, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, polylactic acid, or a combination comprising at least one of the foregoing polymers. In additional embodiments, the digested placenta tissue and/or placenta-derived matrix described herein may exclude salts of calcium, barium, aluminum, strontium, copper, zinc, magnesium, manganese, cobalt, or iron, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), acryl azide, and a combination thereof.

In some embodiments, the decellularized or devitalized placenta tissue and/or placenta-derived matrix described herein does not comprise an additional crosslinker in addition to a natural carrier(s) from the placenta tissue. In additional embodiments, the decellularized or devitalized placenta tissue and/or placenta-derived matrix described herein does not comprise an additional carrier in addition to a natural carrier(s) from the placenta tissue. For example, the decellularized or devitalized placenta tissue and/or placenta-derived matrix described herein may not comprise alginate, propylene glycol alginate, native or crosslinked chitosan, starch, polyethylene glycol, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxylpectin, or carrageenan.

The decellularized or devitalized placenta tissue and/or placenta-derived matrix may or may not include a carrier solution. The carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The carrier solution may also comprise natural and or synthetic polymers selected from the group comprising native or modified collagen, gelatin, agarose, modified hyaluronic acid, fibrin, chitin, biotin, avidin, MATRIGEL®, proteoglycans, laminin, fibronectin, elastin, heparin, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers in addition to a natural carrier(s) from the placenta tissue. In additional embodiments, for example, the decellularized or devitalized placenta tissue and/or placenta-derived matrix described herein may or may not include a carrier in addition to a natural carrier(s) from the placenta tissue, wherein the carrier is selected from the group consisting of native collagen, hyaluronic acid, fibrin, chitin, biotin, avidin, MATRIGEL®, proteoglycans, laminin, fibronectin, elastin, heparin, alginate, genipin, chitosan, starch, glucose or ribose, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxyl pectin, carrageenan, and a combination thereof. Moreover, in further embodiments, the decellularized or devitalized placenta tissue and/or placenta-derived matrix described herein may or may not include a crosslinker in addition to a natural crosslinker(s) from the placenta tissue, wherein the crosslinker is selected from the group consisting of alginate, starch, cellulose and its derivatives (such as cellulose acetate, carboxymethyl cellulose, and methyl cellulose), xanthan gum, dextran, carrageenan, genipin, hyaluronic acid, condroitin sulfate, locust bean gum, gum tragacanth, gum arabic, curdlan, pullulan, scleroglucan, and lower methoxylpectin. glucose or ribose, native collagen, hyaluronic acid, fibrin, chitin, biotin, avidin, MATRIGEL®, proteoglycans, laminin, fibronectin, elastin, heparin, chitosan, and a combination thereof.

In another aspect, the placenta-derived matrix described herein consists essentially of and/or consists of the decellularized or devitalized placenta tissue and the digestion solution. The term "essentially consisting of" defines the scope of the matrix to include additional elements that do not materially affect the protein composition and/or gelation of the matrix consisting of initial elements. For example, the placenta-derived matrix consisting essentially of decellularized or devitalized placenta tissue and the digestion solution may include elements in addition to the decellularized or devitalized placenta tissue and the digestion solution that do not materially affect the protein composition and/or gelation of the placenta-derived matrix consisting of the decellularized or devitalized placenta tissue and the digestion solution. Materially affecting the protein composition herein means changing the protein composition at least by about 0.5, 1, 2, 3, 4, 5, 7, 9, 10, 12, 15, 20, 25, 30, or 40%. Materially affecting the gelation of the matrix herein means changing the viscosity of the matrix at least by about 0.5, 1, 2, 3, 4, 5, 7, 9, 10, 12, 15, 20, 25, 30, or 40%.

In another aspect, the methods described herein may further comprise freezing or freeze-drying said placenta-derived matrix to produce a frozen or freeze-dried placenta-derived matrix. In some embodiments, the placenta-derived matrix may be freeze-dried to a point such that the freeze-dried fragments have an average residual moisture of less than about 10, 5, 4, 3, 2, 1, 0.5, or 0.1 wt %.

In another aspect, the method described herein may further comprise placing the placenta-derived matrix in a mold having a predetermined shape, wherein the placenta-derived matrix is frozen or freeze-dried in the mold. In another aspect, the method described herein may further comprise storing the placenta-derived matrix prior to implanting. In some embodiments, the placenta-derived matrix is stored in a dry state, in a frozen state, in cryo-preservation, or in a wet state. In additional embodiments, the methods described herein may further comprise treating the placenta-derived matrix, which includes, for example, sponge structures and nano-to-micro fibers of the placenta-derived matrix, with a water-replacing agent. In further embodiments, the placenta-derived matrix may be stored in a wet state.

In another aspect, the method comprising freezing or freeze-drying said placenta-derived matrix as describes herein produce a sponge structure. In some embodiments, the frozen and/or freeze-dried placenta-derived matrix comprises pores having an average diameter of about 1, 5, 10, 100, 200, 300, 400, 500, 700, 1000, 1500, 2000, 3000, or 4000 µm or more on an average. In additional embodiments, the frozen and/or freeze-dried placenta-derived matrix comprises pores having an average diameter of about 2, 6, 20, 100, 200, 300, 400, 500, 700, 900, 1000, 1300, 1500, 2000, 3000, or 4000 µm or less on an average. In further embodiments, the frozen and/or freeze-dried placenta-derived matrix comprises pores having an average diameter from about 1 µm to 4000 µm, from 100 µm to 1000 µm, from about 50 µm to 2000 µm, from 100 µm to 500 µm on an average.

In another aspect, the method described herein may further comprise plasticizing the placenta-derived matrix including, for example, sponge structures and nano-to-micro fibers of the placenta-derived matrix, as described in U.S. Pat. Nos. 6,293,970, 6,569,200, 6,544,289, 7,063,726, or U.S. Patent Application Publication No. 2010/0030340, 2014/0180437, 2011/0015757, and 2013/0218294, each of which is incorporated by reference herein by its entirety. In additional embodiments, the method may comprise treating frozen or freeze-dried placenta-derived matrix with a water-displacing agent. The frozen or freeze-dried placenta-derived placenta derived matrix treated with the water-displacing agent may be stored in wet state. In yet further embodiments, the water replacing agent comprises one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids.

In some embodiments, an average void volume of the frozen and/or freeze-dried placenta-derived matrix is about 10, 20, 30, 40, 50, 60, 70, 80, 90, 95, 96, 97, 98, 99% or more. In additional embodiments, an average void volume of the frozen and/or freeze-dried placenta-derived matrix is about 10, 20, 30, 40, 50, 60, 70, 80, 90, 95, 96, 97, 98, 99% or less. In further embodiments, an average void volume of the frozen and/or freeze-dried placenta-derived matrix is from about 10% to about 95%, from about 30% to 95%, from about 40% to about 90%, from about 50% to 90%, from about 60% to about 90%, or from about 20% to 60%.

In another aspect, the method described herein may comprise optionally freezing or freeze-drying said placenta-derived matrix to produce a sponge structure; dissolving the placenta-derived matrix described herein or the sponge structure in a solvent to produce a placenta-derived solution; and electrospinning the placenta-derived solution to produce nano-to-micro fibers. For example, the placenta-derived solution may be electrospun to produce nanofibers as described in U.S. Patent Application Publications 2010/0120115 and 2015/0010607, and WO/2014/160002, each of which is herein incorporated by reference in its entirety.

In some embodiments, the nano-to-micro fibers from the placenta-derived matrix described herein may be prepared, for example, not only by electrospinning, but also by melt-blowing, bicomponent spinning, forcespinning, flash-spinning, extrusion, core-sheath electrospinning with or without copolymer, or self-assembly.

Alignment of the nano-to-micro fibers in the placenta-derived matrix scaffold may be measured by a fast Fourier transform (FFT) analysis. For example, the FFT analysis may be performed by the methods described in *Measuring fiber alignment in electrospun scaffolds: a user's guide to the 2D fast Fourier transform approach*, Ayres C E, Jha B S, Meredith H, Bowman J R, Bowlin G L, Henderson S C, Simpson D G. J Biomater Sci Polym Ed. 2008; 19(5):603-21, which is incorporated by reference in its entirety. In some embodiments, FFT result of the nano-to-micro fibers from the placenta-derived matrix described herein may have adjacent major peaks with about 180° apart from each other.

In some embodiments, the nanofiber described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less. In additional embodiments, the total nanofibers in the placenta-derived matrix scaffolds described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less. In some embodiments, the microfiber described herein may have an average diameter of about 100 micron or less, 90 micron or less, 80 micron or less, 70 micron or less, 60 micron or less, 50 micron or less, 40 micron or less, 30 micron or less, 20 micron or less, 10 micron or less, 5 micron or less, 2 micron or less, or 1 micron or less. In additional embodiments, the total microfibers in the placenta-derived matrix scaffolds described herein may have an average diameter of about 100 micron or less, 90 micron or less, 80 micron or less, 70 micron or less, 60 micron or less, 50 micron or less, 40 micron or less, 30 micron or less, 20 micron or less, 10 micron or less, 5 micron or less, 2 micron or less, or 1 micron or less. In further embodiments, the nano-to-micro fibers described herein may have an average diameter of about 5 nm, 10 nm, 25 nm, 50 nm, 100 nm, 250 nm, 500 nm, 1 micron, 5 micron, 20 micron, 50 micron, 75 micron or more.

In one aspect, the placenta-derived matrix nanofibers described herein may have a length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm. In another aspect the total nanofibers in the placenta-derived matrix scaffolds described herein may have an average length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm.

In some embodiments, the weight percentage of said placenta tissue in said decellularized or devitalized placenta tissue is about 2, 5, 10, 15, 20, 30, 40, 50, 60, 70, 80, 90, 92, 94, 96, 98, 100% or more in a dry state. In additional embodiments, the weight percentage of said placenta tissue in said decellularized or devitalized placenta tissue is about 3, 5, 10, 15, 20, 30, 40, 50, 60, 70, 80, 90, 91, 93, 95, 97, 99, 100% or less in a dry state. In further embodiments, the weight percentage of said placenta tissue in said decellularized or devitalized placenta tissue is from about 2% to about 100%, from about 50% to about 90%, from about 50% to about 80%, from 60% to 100%, from 80% to about 100%, or from about 90% to about 100% in a dry state.

In some embodiments, the weight percentage of said decellularized or devitalized placenta tissue in the placenta-derived matrix is about 50, 60, 70, 80, 90, 5, 98, 99% or more in a dry state. In additional embodiments, the weight percentage of said decellularized or devitalized placenta tissue in the placenta-derived matrix is about 50, 60, 70, 80, 90, 100% or less in a dry state. In further embodiments, the weight percentage of said decellularized or devitalized placenta tissue in the placenta-derived matrix is from about 50% to about 100%, from about 70% to about 100%, from about 80% to about 100%, or from about 90% to about 100% in a dry state. The amount of said decellularized or devitalized placenta tissue in the placenta-derived matrix may be varied to adjust the density, concentration, porosity, and/or viscosity characteristics of the placenta-derived matrix as well as the re-hydration characteristics of the porous structure.

In another aspect, the methods described herein comprise treating the placenta tissue, decellularized and/or devitalized placenta tissue, and/or placenta-derived matrix with one or more treatment solutions. In some embodiments, the method described herein may comprise treating the decellularized and/or devitalized placenta tissue, and/or placenta-derived matrix with one or more treatment solutions after freezing and/or freeze drying before implantation. In some embodiments, the treatment solution comprises an ionic, enzymatic, or chemical crosslinking agent, a photoactive agent, or a polymer. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent comprises one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid.

In another aspect, the method described herein may also comprise adding one or more bioactive supplement(s) to the placenta tissue, decellularized and/or devitalized placenta tissue, and/or placenta-derived matrix. In some embodiments, the one or more bioactive supplement(s) is selected from a group consisting of a growth or differentiation factor of the FGF family, TGF-family, IGF-1, PDGF, EGF, VEGF, HGF, PTHrP, Ihh, dexamethasone, insulin, transferrin, selenium, ITS, or ascorbate. The bioactive supplements may be growth factors, differentiation factors, cytokines, anti-microbial agents, or anti-inflammatory agents. The growth or differentiation factors may be for example, a growth factor of the FGF-family or TGF-family, IGF-1, PDGF, EGF, VEGF, HGF, PTHrP, Ihh (Indian Hedgehog Homolog), dexamethasone, insulin, transferrin, selenium, ITS supplement, ascorbate, or a combination thereof. The cytokines may include GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. Examples of anti-inflammatory agents may include an IL-1βR antibody, TNF-α receptor antagonist, cyclooxygenase-2 specific inhibitors, MAP kinase inhibitors, NO synthase inhibitors, NF-κB inhibitors, or inhibitors of MMP. There are various fibroblast growth factors. As an example, the human FGF-family includes 22 members, FGF-1 through FGF-23. (There is no human FGF-15 because FGF-15 is the mouse ortholog of human FGF-19.) Examples of members of the TGF-family may include TGF-α and TGF-β superfamily. The TGF-β superfamily includes TGF-βs (such as TGF-β1, TGF-β2, TGF-(33), activins, inhibins, bone morphogenic factors (BMPs), modified BMPs, anti-mullerian hormone (AMH), myostatins, and others. There are 20 isotypes of BMPs. They may be separated into four subfamilies, for example, (1) BMP2 and BMP4; (2) BMP3 and BMP3B (also known as growth/differentiation factor 10 (GDF10)); (3) BMPs 5, 6, 7 and 8; and (4) GDFs 5, 6, and 7. In additional embodiments, the method described herein may also comprise adding one or more bioactive supplement(s) extracted from tissue comprising demineralized bone matrix, basement membrane, or submucosa matrix. In further embodiments, the method described herein may also comprise adding one or more antioxidants including, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

In another aspect, the method described herein may also comprise adding one or more agent(s) that have bioactive supplement binding site(s) to the placenta tissue, decellularized and/or devitalized placenta tissue, and/or placenta-derived matrix. In some embodiments, the agents having bioactive supplement binding site(s) may comprise hyaluronan, heparin, heparin sulfate, keratin sulfate, dermatan sulfate, chondroitin sulfate, betaglycan, heparan sulfate proteoglycan, syndecan, biglycan, or decorin. In additional embodiments, the agent(s) that have bioactive supplement binding site(s) increases the affinity of growth factors, differentiation factors, cytokines, anti-microbial agents, or anti-inflammatory agents to the placenta tissue, decellularized and/or devitalized placenta tissue, and/or placenta-derived matrix.

In another aspect, the method described herein may also comprise cutting the placenta tissue, and/or decellularized and/or devitalized placenta tissue prior to digesting and/or homogenizing, to have a dimension of about 0.5, 1, 5, 10, 20, 50, 100, 200, 500 mm or more on average. In additional embodiments, the method described herein may also comprise cutting the placenta tissue, and/or decellularized and/or devitalized placenta tissue to have a dimension of about 1, 5, 10, 20, 50, 100, 200, 550 mm or less on average. In further embodiments, the method described herein may also comprise cutting the placenta tissue, and/or decellularized and/or devitalized placenta tissue to have a dimension from about 1 mm to about 60 cm, from about 1 mm to about 50 cm, from about 1 cm to about 60 cm, from about 1 cm to about 50 cm, or from about 1 cm to about 10 cm on average.

In another aspect, the method described herein may comprise cleaning and disinfecting the placenta tissue, decellularized and/or devitalized placenta tissue. In another aspect, the method described herein may also comprise cleaning and disinfecting the placenta tissue, decellularized and/or devitalized placenta tissue, and removing extraneous tissues associated with the placenta tissue. Placenta tissue, for example, may be cut into small pieces to produce crudely fragmented placenta tissue, and optionally triturated and washed with distilled/deionized endotoxin-free water and/or an aqueous solution, such as isotonic saline, among others. In processing, multiple "washes" or "cleaning" may be affected using volumes of aqueous solution that are 2, 5, or 10 times the approximated volume of the tissue being processed, in some embodiments. The use of three such processing steps may affect an approximate 1:100, 1:500 or 1:1000 dilution of associated solubilizable elements rendering the tissue substantially free (e.g., less than about 10, 0.1, 0.01 or 0.001 wt %) from such solubilizable elements. The placenta tissue pieces that are decellularized or devitalized may have a thickness of about 30, 20, 15, 10, 8, 5, 3, 2, 1, 0.5, 0.1, 0.05 mm or less, in certain embodiments. The placenta tissue pieces that are decellularized or devitalized may also have a thickness of about 30, 20, 10, 8, 5, 3, 2, 1, 0.5, 0.1, 0.05 mm or more. In another aspect, the method described herein may also comprise sterilizing the placenta tissue, decellularized and/or devitalized placenta tissue, and/or placenta derived matrix. Sterilization may involve the use of ionizing radiation, in some embodiments. In other embodiments, the absorbed dose of ionizing radiation may be between about 1.0 KGy and about 50 KGy, between about 8.0 KGy and about 50 KGy, between about 8.0 KGy and about 25 KGy, or between about 8.0 KGy and about 18 KGy. In some embodiments, the sterilizing step may include placing the packaged tissue repair implants comprising the placenta derived matrix on dry ice and irradiating the packaged composition. In certain embodiments, sterilization may be performed at a temperature of between about −20° C. and −50° C. The implants of the present invention may be sterilized using gamma irradiation, supercritical carbon dioxide, ethylene oxide, or electronic-beam.

In another aspect, the method described herein may comprise adding one or more bone fragment material(s) to the placenta-derived matrix. In some embodiments, bone fragments material(s) comprise one or more selected from the group consisting of bone, cortical bone, cancellous bone, cortical cancellous bone, ceramics, hydroxyapatite, calcium phosphate, calcium sulfate, and calcium carbonate. The bone may be demineralized bone or non-demineralized bone. "Demineralized bone matrix (DBM)" as used herein refers to bone having less than about 8 wt % residual calcium. Demineralization involves treating a bone tissue to remove its inorganic mineral hydroxyapatite material. The level of demineralization of a bone tissue is defined by the amount (wt %) of residual calcium found in the demineralized bone. In some embodiments, the demineralized bone may still contain physiologically active levels of growth and differentiation factors (e.g., osteogenic growth factors, such as bone morphogenetic proteins (BMPs)) remaining from the initial bone even after the demineralization treatment. In further embodiments, the demineralized bone may contain collagen, glycosaminoglycans, osteocalcin, osteonectin, bone sialo protein, osteopontin, and mixtures thereof. "Non-demineralized bone" as used in the present application refers to bone that has not been treated to remove minerals present such as, for example, hydroxyapatite. Certain biologically functional scaffold and/or implant of the present invention may include demineralized bone particles or fibers. Demineralized bone matrix may be prepared from cleaned and disinfected bone that have been freeze-dried or not freeze-dried and ground/fractured/milled into bone particles or fibers. Bone particles may be selected by, for example, using sieving devices (i.e., mesh sieves) commercially available for obtaining particles within a desired size range. Such demineralized bone particles may have an average diameter of between about 125 microns and about 4 mm; between about 710 microns and about 2 mm; between about 125 microns and about 500 microns; between about 125 microns and about 850 microns; between about 125 microns and about 710 microns; between about 250 and 1000 microns; or between about 250 microns and about 710 microns. Certain embodiments of the present invention may include demineralized bone particle that is commercially available. For example, a suitable demineralized bone particle that is widely and reliably available is produced by LifeNet Health, Virginia Beach, Va. Some biologically functional scaffold and/or implant of the present invention may include demineralized bone fibers. In certain embodiments, the demineralized bone fibers may have an average thickness of between about 0.1 mm and about 0.3 mm and an average width of between about 0.3 mm and about 1.0 mm. The length of the fibers may vary. In some embodiments, the demineralization process begins by producing bone particles having an average diameter size range of between about 1 mm and about 2 mm or bone fibers having an average dimension of 0.1 mm to 0.3 mm thickness and an average width of about 0.3 mm to about 1 mm. The fragments may be treated with cleaning solutions. If the bone to be processed into fragments has not been previously cleaned and/or disinfected, they may be cleaned and/or disinfected by the use of detergents, hydrogen peroxides, antibiotics, and/or alcohols to affect a removal of associated tissues such as bone marrow and cellular elements. Following cleaning and disinfection, these fragments (i.e., particles and fibers) may be demineralized by exposure to dilute hydrochloric acid to affect a removal/reduction of the mineral component of the bone fragments (i.e., particles and fibers). Such additional processing may, in some instances, inactivate potential viral contamination (i.e., HIV and hepatitis viruses, among others).

In another aspect, the method described herein may or may not comprise processing the placenta-derived matrix and/or scaffolds comprising the placenta-derived matrix under negative hydrostatic pressure before being frozen or freeze-dried to increase porosity. Three-dimensional (3-D) macro-porous structure in the present invention is designed to provide support for the cells until they are organized into a functioning tissue. After implantation, the architecture of the macro-porous structure can control the extent of vascularization and tissue ingrowth. The pore size and volume can be adjusted by adding porogens, application of inert gas, or application of a negative hydrostatic pressure before or after freeze-drying the placenta-derived matrix.

In another aspect, the invention relates to placenta-derived matrix comprising decellularized or devitalized placenta tissue. The pH of the placenta-derived matrix may be about 8.0 or more, for example, in the range of 8.0-9.0, preferably 8.0-8.5, more preferably 8.0-8.2. For example, the pH of the matrix is at least about 8.0, 8.1, 8.2, 8.3, 8.4, 8.5, 8.6, 8.7, 8.8, 8.9 or 9.0, preferably at least about 8.0.

In another aspect, the invention also relates to placenta-derived matrices prepared by the methods described herein. In another aspect, the invention relates to scaffolds comprising the placenta-derived matrix described herein. The scaffold may include an implant, which is a scaffold configured to be implanted in vivo. The scaffold described herein may have a porous structure, including porous sponge-like structure. The term "porous sponge-like structure" refers to a three-dimensional structure that is porous, coherent, elastic, flexible, fibrous and resilient. In a dry state, the porous sponge-like scaffold of the present invention may quickly absorb fluid. In the wet state, the porous sponge-like scaffold of the present invention may maintain the porosity, cohesiveness, and/or integrity. The wet porous sponge-like structure may resist certain tensile stress, and bounce back and reabsorb fluid after being released from compression. The porous sponge-like scaffold and/or the biologically functional scaffold may be twisted, folded, rolled, molded, placed and/or inserted into or on the defect, skin lesion, topical wound, ulcer, breast after lump- or mass-ectomy, tunneling wound (e.g. fistula), or wrapped around the defect of bone, cartilage or soft tissue.

In another aspect, the placenta-derived matrix described herein may comprise type I collagen, type IV collagen, laminin gamma-1, fibronectin, chroionic sommatomammotropin, FGF-12, FGF-13, IGF-2, EGFL-7, and bFGF. In some embodiments, the concentration of the type I collagen in the placenta-derived matrix is about 20, 25, 30, 31, 32, 33, 34, 35, 36, 37, 38, 39, 40, 45% or more; about 20, 25, 30, 31, 32, 33, 34, 35, 36, 37, 38, 39, 40, 45% or less; and/or about between 20 and 50%, between 25 and 45%, between 30 and 40%, or between 33 and 38%.

The placenta-derived matrix described herein may be rich in ECM proteins and glycoproteins found throughout the body, which play a vital role in driving key cellular events such as cell migration, adhesion, differentiation, proliferation, and survival. Proteins present in the placenta-derived matrix, such as collagen IV, the most common type of collagen found in the human basement membrane, laminins, fibronectin, and proteoglycans (e.g. heparan sulfate), may provide the basement membrane with a tensile strength capable of supporting cells, binding cells to the underlying collagenous matrix and separating epithelia from mesenchyme/underlying connective tissue.

In another aspect, the homogenized placenta tissue described herein may or may not include "crudely fragmented placenta tissue," referring to connective tissue that has been sliced, ground, carved, chipped, chopped, minced, cut, dissected, rent, ripped, sectioned, snipped, diced, shaved, comminuted, or trimmed into fragments. Such fragmented placenta tissue may have an average diameter greater than about 50 microns and less than about 0.5 cm, for example, having cut dimensions of approximately 0.5×0.5 cm, and a thickness appropriate to the tissue being crudely fragmented. In some embodiments, the crude fragments may not be of uniform size.

In another aspect, the invention relates to methods of cell culture comprising culturing cells on or in the placenta-derived matrix prepared by the methods described herein as a two-dimensional or three-dimensional scaffolds. As used herein, cell culture refers to the maintenance of cells in an artificial environment, commonly referred to as an in vitro environment. The term cell culture is a generic term and may be used to encompass the cultivation not only of individual cells, but also of tissues, organs, organ systems or whole organisms. The cells used in the culture methods disclosed herein can be any prokaryotic or eukaryotic cell. The cell type used in the culture methods disclosed herein need not be from the same species from which the cell support compositions derive. In addition, the cells may be from an established cell line, or they may be primary cells or genetically engineered cells. For example, the cells may be selected from the group consisting of stem cells, adipose derived stem cells, dorsal root ganglion cells, pancreatic beta islet cells, cardiomyocytes, hepatocytes, iPSCs, cancer cells, and umbilical vein endothelial cells.

For example, the invention provides for growing and/or culturing cells on or in the placenta-derived matrix described herein. "Growing and/or culturing cells on or in the placenta-derived matrix described herein" includes traditional cell culture methods as well as placing on a surface of the placenta-derived matrix described herein in any setting, such as in natural or synthetic biocompatible matrices or tissues. The cells may be mammalian, such as but not limited to human, bovine, porcine, murine, ovine, equine, canine, feline and others. In some embodiments, the cells that are cultured on or in the placenta-derived matrix described herein are stem cells. As used herein, a stem cell is used as it is in the art and means a cell that has the ability to divide and give rise to one daughter cell that may be at least partially differentiated and to another daughter cell that retains the developmental potential of the mother cell. As used herein, stem cells can be adipose derived stem cells, dental pulp stem cells, adult stem cells (ASCs), embryonic stem cells (ESCs), tissue-specific progenitor cells, and/or induced pluripotent stem cells (iPSCs). The ASCs may include, but is not limited to, hematopoietic stem cells, mammary stem cells, intestinal stem cells, mesenchymal stem cells, endothelial stem cells, neural stem cells, olfactory adult stem cells, neural crest stem cells, and testicular cells. In further embodiments, the placenta-derived matrix described herein may be used in in vitro methods for supporting cell growth and proliferation as well as for increasing maintenance or facilitating differentiation, such as osteogenesis, chondrogenesis, or ligament/tendon genesis, in the stem cells cultured on or in the placenta-derived matrix described herein.

In some embodiments, the cells that are cultured on or in the placenta-derived matrix described herein may be cardiomyocytes, human umbilical vein endothelial cells (HUVEC), induced pluripotent stem cell (iPSC), hepatocytes, osteoblasts, chondrocytes, dorsal root ganglia (DRG) cells, mesenchymal stem cells, adipose-derived stem cells, embryonic stem cells, progenitor cells, differentiated cells, undifferentiated cells, and/or -pluripotent stem cells. Appropriate cells may also include, but are not limited to cells of the ectodermal lineage, cells of the mesodermal lineage, and cells of the endodermal lineage. Examples of cells of the ectodermal lineage include but are not limited to keratinocytes, neurons. Examples of cells of the mesodermal lineage include but are not limited to myoblasts, adipocytes, fibroblasts, endothelial cells, osteoblasts, chondrocytes, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines.

In some embodiments, the cells may be derived from autologous or allogeneic sources. The cells may be differentiated cells including chondrocytes, osteoblasts, osteoclasts, endothelial cells, epithelial cells, fibroblasts, and periosteal cells. Additionally, the cells may be totipotent, pluripotent, multipotent, progenitor cells, tissue-specific progenitor cells, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, placental membrane, menstrual blood, teeth, nucleus pulposus, brain, neonatal foreskin, skin, hair follicle, intestinal crypt, neural tissue, liver, pancreas, or muscle. The cells may be derived from skeletal muscle, smooth muscle, and cardiac muscle. The stem cells may be derived from genetic reprogramming of mature cells, such as induced pluripotent stem cells (iPSCs). All cells may further be derived from living or recently deceased donors.

Any cell described herewith may be cultured on or in the placenta-derived matrix described herein for between about 15 minutes and about one year, about 15 minutes and about 6 months, about 15 minutes and about 3 months, about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the absence or presence of one or more growth factors described herein and (1) a tissue or an organ, (2) a matrix, or (3) a combination thereof. Cells that have been cultured in the absence or presence of one or more growth factors described herein in a cell culture medium may subsequently be applied to a matrix, a tissue, an organ or a combination thereof, in certain embodiments.

The method of cell culture may further comprise storing the cells on or in the placenta-derived matrix. In some embodiments, the cells on or in the placenta-derived matrix are stored at room temperature (i.e. about 24° C.), at about 4° C., at about −20° C. or in cryopreservation. In other embodiments, the cells on or in the placenta-derived matrix are stored at a temperature from about −200, −180, −100, −50, −45, −40, −35, −30, −25, −20, −10, −5, 0, 1, 2, 3, 4, 5, 10, 20, 21, 22, 23, 24, 25, 26, 27, 28, 29, 30, 35, 36, 37, 38, or 39° C. to about −150, −140, −130, −90, −40, −35, −30, −25, −20, −15, −10, 0, 1, 2, 3, 4, 5, 6, 7, 8, 9, 10, 15, 25, 30, 35, 36, 37, 38, or 40° C. In other embodiments, the cells on or in the placenta-derived matrix are stored at a temperature from about −200 to 50° C., from about −160 to 36° C., from about −160 to 25° C., from about −160 to 5° C., from about −5 to 23° C., from about 0 to 30° C., or from about 15 to 40° C.

In another aspect, the placenta-derived matrix described herein may be used as a cryoprotectant. Cryopreservation described herein refers to preservation at a temperature below −150° C. (i.e. 123K). A cryoprotectant described herein, however, refers to a protectant that preserves biological activity of a protein not just after the cyropreservation but also after freezing or lyophilization. In some embodiments, the invention relates to methods of inhibiting and/or reducing loss of biological activity of a protein due to freezing or lyophilization, the method comprising exposing the protein to the placenta-derived matrix in an effective amount sufficient to inhibit or reduce loss of biological activity of a protein due to freezing or lyophilization. In further embodiments, the protein may be any protein in any of the cells, such as those described herein.

In another aspect, the invention relates to methods of cell delivery comprising mixing cells in the placenta-derived matrix described herein to produce a mixture of the cells and the placenta-derived matrix, and painting, airbrushing, dripping or injecting the mixture on or into a site of interest. In another aspect, invention also relates to methods of cell delivery comprising culturing cells in the placenta-derived matrix described herein to produce a culture of the cells and the placenta-derived matrix, and painting, airbrushing, dripping or injecting the culture on or into a site of interest. In some embodiments, the site of interest is in a subject including, but not limited to, human, non-human animal, cow, and pig.

In another aspect, the invention relates to methods of promoting differentiation of the stem cells or tissue-specific progenitor cells described herein, the method comprising culturing the stem cells or tissue-specific progenitor cells on or in the placenta-derived matrix prepared by the method described herein. For example, the stem cells or tissue-specific progenitor cells are differentiated into osteoblasts, chondrocytes, cardiomyocyte, pancreatic cells, neuronal cells, ligament or tendon. In some embodiments, the tissue-specific progenitor cells are differentiated into a tissue of interest without adding a growth factor. In another aspect, the invention also relates to methods of promoting vascular, myogenic, or neurogenic differentiation of the stem cells or tissue-specific progenitor cells, the method comprising culturing the stem cells or tissue-specific progenitor cells on or in the placenta-derived matrix described herein.

In some embodiments, the placenta-derived matrix described herein may be used in in vitro methods for extending the maintenance of stemness in tissue-specific progenitor cells (i.e. ability to proliferate and/or differentiate into a specific tissue through extended culture) and/or self-renewing ability of the tissue-specific progenitor cells, the method comprising culturing the tissue-specific progenitor cells on or in the placenta-derived matrix, optionally without adding a growth factor or another secondary factor to induce the maintenance of the cells. In further embodiments, the placenta-derived matrix described herein may also be used in in vitro or in vivo methods for promoting differentiation of pluripotent stem cells without adding additional growth factors or another secondary factor to induce the differentiation of the cells. In other embodiments, the placenta-derived matrix described herein may also be used in in vitro or in vivo methods for promoting differentiation of pluripotent stem cells and/or tissue-specific progenitor cells with an addition of one or more growth factors or other secondary factors to induce the maintenance or differentiation of the cells. In additional embodiments, the placenta-derived matrix described herein may also be used in in vitro or in vivo methods for enhancing the effect of one or more growth factors or other secondary factors to induce the maintenance or differentiation of the cells in promoting differentiation of pluripotent stem cells and/or tissue-specific progenitor cells.

In another aspect, the invention also relates to methods of repairing, replacing, filling, regenerating a defect(s), or reducing or inhibiting scarring of a defect(s) in a tissue comprising implanting the placenta-derived matrix described herein at the site of scarring or defect. In some embodiments, the implanting is performed by painting, airbrushing, dripping, or injecting the placenta-derived matrix to the site of defect, inserting the placenta-derived matrix between tissues or organs, for example, in the interstitial space around cells or cell structures, such as muscle or nerve bundles, or placing the placenta-derived matrix on top of the defect. The tissues with the defect may be heart, liver, pancrease, bone tissues, cartilage, or soft tissues. Examples of soft tissues with the defect may include tendon, ligament, dermis, skin, vocal cord, nerve, bladder, vagina, urethral, heart, subcutaneous tissue, fascia, breast, muscle, placental membrane, placenta, and rotator cuff. In another aspect, the tissues with the defect may be in the musculoskeletal system, digestion system, cardiovascular system, respiratory system, urinary system, reproductive system, nervous system, and/or immune system. In some embodiments, the method excludes rehydration of the placenta-derived matrix prior to implanting to allow said placenta-derived matrix to absorb blood, fluid, and/or autologous cells in situ. Alternatively, implantation of a tissue repair implant comprising the placenta-derived matrix into a human or animal can be conducted by re-hydrating the tissue repair implant with a rehydrating solution; optionally seeding vital cells on or in the placenta-derived matrix and/or tissue repair implant to render the tissue repair implant vital; optionally culturing the cell-seeded tissue repair implant before implantation; and implanting the tissue repair implant into the defect. In another aspect, the method may further comprise rehydrating a tissue repair implant comprising the placenta-derived matrix with a rehydrating solution; optionally seeding vital cells on or in said placenta-derived matrix and/or tissue repair implant to render said tissue repair implant vital; and optionally culture said cell-seeded tissue repair implant before implantation. In some embodiments, the rehydrating solution comprises one or more selected from the group consisting of blood or bone marrow aspirate, platelet rich plasma, cerebrospinal fluid, synovial fluid, enzymes, bioactive supplements, natural polymers, synthetic polymers, photoactive agents, antioxidants, crosslinking agents, antimicrobial agents, vital cells, and one or more agents that have bioactive supplement binding site(s). In additional embodiments, the vital cells comprise one or more selected from the group consisting of cells from autologous or allograft bone marrow aspirate; stromal cells from bone marrow; stromal cells from fat, synovium, periostieum, perichondrium, muscle, dermis, umbilical cord blood, placenta, placental membrane, and Warton's jelly; and pericytes.

In another aspect, the invention relates to methods of using the placenta-derived matrix described herein as a tissue bulking agent, or a wound treatment matrix for open wound or a tunnel wound. In another aspect, the invention also relates to methods of marking a tissue part of interest comprising implanting the placenta-derived matrix described herein adjacent to the tissue part of interest. In another aspect, the invention also relates to methods of resecting a tissue comprising implanting the placenta-derived matrix described herein underneath a tissue part of interest, and resecting the tissue part above the placenta-derived matrix. In these embodiments, the implanting of the placenta-derived matrix may mark a tissue part of the interest to be resected without any further marking. In some embodiments, the methods of resecting a tissue further comprises additionally marking the tissue part of interest prior to implanting the placenta-derived matrix, for example by cutting or scratching the edge(s) of the tissue part of interest without dissecting the tissue part of interest away from the remaining part of the tissue or organ. In further embodiments, the implanting may comprise injecting the placenta-derived matrix adjacent to the tissue part. In additional embodiments, the tissue may be sessile or flat neoplasms confined to the superficial layers (mucosa and submucosa) of a GI tract, and the methods of resecting the tissue may be used for endoscopic mucosal resection and endoscopic submucosal dissection. For example, the placenta-derived matrix may replace or complement with the solutions for submucosal injection, such as glycerol and hyaluronic acid, described in Kantesevoy et al., vol. 68, No. 1, Gastrointestinal Endoscopy (2008), which is incorporated herein by reference in its entirety. The methods of resecting a tissue may also comprise cutting the mucosa after implanting the placenta-derived matrix, dissecting the tissue, and lifting the tissue away from the remaining GI tract. Exemplary scheme is illustrated at wjgnet.com/1948-5190/full/v4/i10/WJGE-4-438-g001.jpg.

For example, the invention also relates to methods of promoting osteoinductivity, with the methods comprising culturing cells on or in the placenta-derived matrix described herein. As used herein, "osteoinductivity" can refer to causing cells to differentiate into cells that are more osteoblast-like in phenotype, or the term can refer to increasing the proliferation of osteoblasts, or both. The cells, prior to culture on or in the placenta-derived matrix, may be undifferentiated or partially differentiated cells. The cells may be present in culture or in a tissue, organ or portion thereof or in an organism. The osteoinductive activity of the placenta-derived matrix may or may not be altered, including but not limited to, enhanced activity, relative to a control surface.

The invention also relates to methods of promoting chondroinductivity, with the methods comprising culturing cells on or in the placenta-derived matrix described herein. As used herein, "chondroinductivity" can refer to causing cells to differentiate into cells that are more chondrocyte-like in phenotype, or the term can refer to increasing the proliferation of chondrocytes, or both. The cells, prior to culture on or in the placenta-derived matrix, may be undifferentiated or partially differentiated cells. The cells may be present in culture or in a tissue, organ or portion thereof or in an organism. The chondroinductive activity of the placenta-derived matrix may or may not be altered, including but not limited to, enhanced activity, relative to a control surface.

The invention also relates to methods of promoting ligament/tendon differentiation, with the methods comprising culturing cells on or in the placenta-derived matrix described herein. As used herein, "ligament/tendon differentiation" can refer to causing cells to differentiate into cells that are more ligament and/or tendon-like in phenotype, or the term can refer to increasing the proliferation of ligament and/or tendon, or both. The cells, prior to culture on or in the placenta-derived matrix, may be undifferentiated or partially differentiated cells. The cells may be present in culture or in a tissue, organ or portion thereof or in an organism. The ligament/tendon differentiation activity of the placenta-derived matrix may or may not be altered, including but not limited to, enhanced activity, relative to a control surface.

There are varieties of osteoblast, chondrocyte, ligament/tendon differentiation markers that can be measured to assess osteoinductivity, chondroinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells cultured on or in the placenta-derived matrix described herein. The ability of the placenta-derived matrix to stimulate or induce the alkaline phosphatase expression in an otherwise non-bone forming cells, such as myoblast (C2C12 cells), would indicate that the placenta-derived matrix has osteoinductive activity. In these assays, cells cultured on or in the placenta-derived matrix and on a control surface are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" surface of the placenta-derived matrix would simply cause an increase in the osteoblastic markers in experimental cells. Similarly, chondrocyte markers, including but not limited to type X collagen, type II collagen, Sox 9, Aggrecan. Matrilin-1 and CEP-68, to name a few, can be used to assess chondroinductive potential. Moreover, ligament/tendon markers, including but not limited to scleraxis, can be used to assess ligament/tendon differentiation potential.

Moreover, osteoinductivity, chondroinductivity, and ligament/tendon differentiation may be determined in tissue culture by investigating the ability of the placenta-derived matrix to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts, such as alkaline phosphatase, etc. For example, the osteoinductive, chondroinductive, ligament/tendon differentiation potentials of the placenta-derived matrix may be more than 0.2, 0.4, 0.6, 0.8, 1, 2, 3, 4, 5, 6, 7, 8, 9 or 10 times greater than a control. In another example, the osteoinductive, chondroinductive, ligament/tendon differentiation potentials of the placenta-derived matrix described herein may be more than 10, 20, 30, 40, 50, 60, 70, 80, 90, 100, 500 or even 1000 times greater than those of a control scaffold.

Osteoinductivity, chondroinductivity, ligament/tendon differentiation, for assessing the bone, cartilage, ligament or tendon forming potential induced by the placenta-derived matrix in a location such as muscle, may also be evaluated using a suitable animal model. For example, intramuscular implantation into a rodent has been used as a model to assess osteoinductive activity of the placenta-derived matrix.

The invention also relates to methods of promoting cell angiogenesis, hemostatic, biocompativlity, infection resistance, attachment, proliferation or maintaining the differentiated state or preventing de-differentiation of osteoblasts, chondrocytes, ligament cells, tendon cells, fibroblasts, adipocytes, and/or any cell type disclosed herein with the methods comprising culturing the cells on or in the placenta-derived matrix described herein. The proliferative activity of the placenta-derived matrix may or may not be altered, including but not limited to, enhanced activity, relative to a control surface. The invention further relates to methods of promoting adipose tissue formation of adipocytes, fibroblasts, epithelial cells, and/or vascular endothelial cells. The invention also relates to methods of increasing or promoting angiogenesis, hemostatic function, biocompatibility, anti-scarring, anti-inflammatory, and/or infection resistance, Mitogenicity may be assessed by investigating cell proliferation induced by the placenta-derived matrix using various in vitro assays that measure metabolic activity, such as MTT [3-(4,5-dimethylthiazol-2-yl)-2,5-diphenyltetrazolium bromide assay, alamarBlue® assay, and others. The alamarBlue® assay uses a non-cytotoxic reduction-oxidation indicator to measure cell metabolic activity, making it a nondestructive assay for assessing the mitogenic activity of the placenta-derived matrix described herein. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as staining cells with trypan blue and counting with a hemacytometer.

The invention also relates to methods of increasing or promoting osteogenesis, chondrogenesis, or ligament/tendon genesis in cells. The methods may comprise culturing the cells on or in the placenta-derived matrix described herein. As used herein, "osteogenesis" is the deposition of new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. The osteogenic, chondrogenic, ligament, or tendon inducing activity of the placenta-derived matrix may or may not be altered, including but not limited to, enhanced activity, relative to a control surface. The cells may include cells in any tissue in which bone, cartilage, ligament, or tendon formation is desired, such as, but not limited to, bone, cartilage, ligament, muscle, tendon, etc.

In another aspect, the invention relates to methods of coating placenta-derived matrix on a surface of a substrate. The placenta-derived matrix may have a basic pH of, for example, about 8.0 or more. The basic pH may be in the range of 8.0-9.0, preferably 8.0-8.5, more preferably 8.0-8.2. For example, the basic pH of the matrix is at least about 8.0, 8.1, 8.2, 8.3, 8.4, 8.5, 8.6, 8.7, 8.8, 8.9 or 9.0, preferably at least about 8.0.

In some embodiments, the methods comprises decellularizing or devitalizing at least a piece of placenta tissue to produce a decellularized or devitalized placenta tissue; digesting the decellularized or devitalized placenta tissue to produce a placenta-derived matrix; and coating at least a part of a surface of a substrate with the placenta-derived matrix. In some embodiments, the method may further comprise further comprising homogenizing the placenta tissue concurrently or prior to the digesting. In additional embodiments, the placenta-derived matrix may be coated to the surface by electrospinning the placenta-derived matrix, for example in a form of nanofibers, on the surface. The invention further relates to a scaffold coated with the placenta-derived matrix in accordance with the methods described herein. The invention also relates to a synthetic surface coated with the placenta-derived matrix produced by the methods described herein. The invention additionally relates to methods of cell culture comprising culturing cells on a cell culture surface coated with the placenta-derived matrix produced by the methods described herein.

In further embodiments, the present invention may also relate to drug deliver using the placenta-derived matrix as a carrier. For example, the placenta-derived matrix may encapsulate the bioactive supplements described herein and deliver such bioactive supplements to a site of interest.

Any of the methods of the present invention can be performed in virtually any setting, such as an in vivo, ex vivo, in situ or in vitro setting. For example, methods of promoting osteogenesis, chondrogenesis, or tendon/ligament inducing activities in cells may be performed in cell culture, may be performed in seeded cells on the placenta-derived matrix, or may be performed in an intact organism. Moreover, any combination of any two or more of any of the embodiments described herein are contemplated.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

The following examples are illustrative and are not intended to limit the scope of the invention described herein.

EXAMPLES

Example 1: Preparing Placenta-Derived Matrix (HuMATRIX)

Whole frozen human placenta (or heart or liver) stored at −80° C. was allowed either immediately processed or allowed to thaw overnight at 4° C. Using a disinfected deli slicer (Chefs Choice International Professional Electric Food Slicer Vari Tilt M645) or meat grinder or band saw, the placenta tissue was cut into smaller pieces (~half a cm in width and diameter) to 50 g of tissue (wet weight). To wash and remove excess blood, the placental tissue was washed with one liter of 4° C. cold water MilliQ water and then washed vigorously, in a container with one liter of 4° C. cold water MilliQ water supplemented with 1% ABAM for 30 mins at 1200 RPM on an orbital shaker. This process was repeated until excess blood was significantly reduced. To decellularize the placenta, the washed tissue was shaken at 200 RPM in one liter of devitalization buffer supplemented with 2.5 g NEM, a protease inhibitor, 20 g NLS, and 1% ABAM overnight at room temperature.

Next, 10.2 g of wet tissue (=~2 g lyophilized tissue) was added to 1 mg/ml pepsin/0.1 M HCl solution. Three concentrations of the placenta-derived matrix (10 mg/ml, 20 mg/ml, and 40 mg/ml) have been generated. At around 40 mg/ml, the product had high viscosity that was non-flowable. The tissue was blended in five 10-second pulses with a polytron homogenizer until the slurry appeared homogenous. The resulting solution was stirred for about 24-60 hours at room temperature. Following the about 60 hours, the pepsin HCl was brought to pH 8.0 briefly then to pH 7.0-7.2 using sodium hydroxide and hydrochloric acid. The HuMATRIX final product appeared viscous and near translucent in appearance. To test for gelling properties, a sample of HuMATRIX was heated at 37° C. for 15 minutes. The HuMATRIX samples were stored at −80° C. for long-term storage, or at 4° C. for use within 2 weeks. The final products of HuMATRIX were converted to a hydrogel at around 37° C., or lyophilized to form a sponge. Following lyophilization, the HuMATRIX sponge were dissolved in organic solvents (such as hexafluoroisopropanol) and electrospun into nanofiber sheets. Furthermore, the lyophilized sponge of HuMATRIX was able to surprisingly be re-dissolved in 0.5M acetic acid, neutralized, and again able to be cast as a hydrogel at 37° C.

In another exemplary method, the placenta tissue was washed with saline solution instead of water. In other exemplary methods, in additional to the saline wash, a detergent was used or a shorter duration was employed in decellularizing the placenta tissue. The total protein yields along with the amounts of impurities in the matrix following the process were determined. The proteomic results showed that the water wash resulted in less cellular residual debris compared to the saline wash, but the saline wash resulted in higher concentration and more diversity of growth factors in the final matrix.

Example 2: Protein Profile of Placenta-Derived Matrix

To determine the protein profile of HuMATRIX, a SDS-PAGE assay was performed. 10 µl Dithiothreitol (DTT) was added to each sample and heated at 100° C. for 5 minutes to break any existing disulfide bonds. After heating the sample for 5 minutes, 40 µl of extract was loaded onto a 1.5 mm 4-12% Tris-Glycine gel along with a 10 µl of Novex sharp marker. The gel was ran for 1 hr (200 Vconstant, 125 mA start, 80 mAmps end), washed with MilliQ water stained with commassie blue overnight, and then visualized. Numerous bands were present. Four placenta-derived matrix samples derived from four different donors showed batch-to-batch consistency on SDS PAGE gel. The major protein bands from MATRIGEL® were used as a control. A distinctly different band pattern and major protein composition were compared to placental extraction with urea or by decellularization followed by urea extraction. Heavy bands were observed at 160 kDa indicative of collagen chains. Protein composition appeared consistent between groups with the HuMATRIX chemistry relative to the traditional MATRIGEL/Urea extraction chemistry, and distinct from NLS decellularized and then urea extracted placenta matrix.

Example 3: Coating Surface with Placenta-Derived Matrix

To measure the coating or binding efficiency of the placenta-derived matrix to cell culture plastic, HuMATRIX at a various concentrations from 0.6-1.3 mg/cm$^2$ was applied to 24 well plates and stained with Coomassie blue to assess complete and total staining and thus ECM coverage on the well, with an even coating of extracellular matrix protein possible on charged tissue culture plastic in this concentration range.

Example 4: Identification and Quantification of Proteins, Growth Factors, and DNA Following the manufacturer instructions provided with the kits, ELISAs for quantifying the amounts of total protein, collagen type I, collagen type IV, fibronectin, laminins, and human placental lactogen were performed on HuMATRIX, HuMATRIX with slight chemistry variations, and control matrices to compare and contrast differences in the matrices.

Collagen I, IV, fibronectin, laminins, and placental lactogen content in human placenta hydrogels were determined from each 8 unique donors using quantitative sandwich enzyme-linked immunosorbent assay kits commercially available from R&D systems (Minneapolis, Minn.), Chondrex (Redmond, Wash.) and Genwaybio (San Diego, Calif.). All assays were performed on triplicate samples from each donor tissue, per manufacturer specifications.

ECM protein was normalized as weight percent by comparing the total protein content as determined by the Lowry method for total protein quantitation. In all, collagen type I was on average 41% of the composition, type IV collagen comprised around 3% of the total matrix, and laminin gamma 1 and fibronectin were <1% of the composition on average. Human chorionic sommatomammotropin (aka placental lactogen) was found at around 175 ng/mL on average in HuMATRIX. Placental lactogen has been reported in the literature to be highly bioactive, stimulating insulin production from pancreatic islet cells, causing a 4.4 fold increase in MCF7 tumor cell proliferation, inducing angiogenesis, stimulating fetal hepatocyte DNA synthesis, and other functions at levels at or below the average concentration present in HuMATRIX.

Human placenta hydrogel samples were weighed and placed in impact resistant tubes. The protein concentration of the supernatant was determined using a DTT compatible BCA assay (Thermo Fisher Scientific, San Jose, Calif.) and 100 µg of extracted protein sample was run on a NuPAGE reducing gel (4-12% Bis-Tris Gel) (Life Technologies, Carlsbad, Calif.) with NuPAGE MOPS SDS 1× buffer run at 200V for about 10 min. After the protein band had migrated 3-5 mm, the gel was stained with Page Blue (Bio-Rad, Hercules, Calif.) and the entire protein band cut out. The gel was de-stained and washed three times in 50 mM NH$_4$HCO$_3$; 50% acetonitrile and 80% acetonitrile. The gel-bound proteins were reduced with 1 ml of 40 mM DTT for 25 min. at 56° C. The gels were rinsed with 1 ml of 50 mM NH4HCO3 buffer and the reduced proteins alkylated with 1 ml of 50 mM Iodoacetamide for 30 min. at 25° C. in the dark with constant mixing. The Iodoacetamide was discarded and the gel bound proteins were digested with 0.5 ml of trypsin (20 ng/µl; Promega, Madison, Wis.) in 50 mM NH4HCO3 buffer at 37° C. with constant mixing for 12 h. After digestion, the tryptic fraction was collected by washing the gels with 50 mM NH$_4$HCO$_3$. The eluent containing the tryptic peptides was dried using a Speed-Vac apparatus (Thermo Fisher Scientific) and stored at 4° C. prior to mass spectrometric analysis.

The dried samples were dissolved with 20 µl of 0.1% formic acid/water, 2 µl of each sample was then analyzed by LC/ESI-MS/MS on a Q-Exactive (Thermo Fisher Scientific) mass spectrometer with an Easy NanoLC-1000 system, using data dependent acquisition with dynamic exclusion (DE=1) settings. The data dependent acquisition settings used were a top 12 higher energy collision induced dissociation for the Q-Exactive MS. Resolving power for Q-Exactive was set at 70,000 for the full MS scan, and 17,500 for the MS/MS scan at m/z 200. LC/ESI-MS/MS analyses were conducted using a C18 column (75 μm×150 mm). The mobile phases for the reverse phase chromatography were (A) 0.1% Formic Acid/water and (B) 0.1% Formic Acid in acetonitrile. A four-step, linear gradient was used for the LC separation (column pre-equilibration with 2% B for 10 min; 2% to 30% B in the first 47 min., followed by 80% B in the next 1 min. and holding at 80% B for 12 min.).

A label-free precursor ion detection method (Proteome Discoverer, version 1.3, Thermo Fisher Scientific) was used with specific retention times on precursors/fragments within 5 ppm mass accuracy. The Sequest algorithm was used to identify peptides from the resulting MS/MS spectra by searching against the combined Human protein database (a total of 28,000 sequences) extracted from Swissprot (version 57) using taxonomy "Human." Searching parameters for parent and fragment ion tolerances were set as 15 ppm and 60 mmu for the Q-Exactive MS. Other parameters used were a fixed modification of carbamidomethylation –Cys, variable modifications of Phosphorylation (S,T,Y) and oxidation (Met). Trypsin was set as the protease with a maximum of 2 missed cleavages. Only those proteins that had >2 peptides identified (or >50% of protein covered by a single peptide) were included in the comparative quantitative analysis steps, and resulted in a correct protein identification probability of $P<0.05$. Peptides that have yet to be definitively linked to a protein were excluded from further analysis.

Venn Diagrams generated from mass spectrometry data of the total proteins identified in HuMATRIX showed high homology between HuMATRIX preparations as compared to alternative placenta ECM extraction strategies (MATRIGEL® chemistry with urea extraction, labeled as T1 and D1, vs. P1 for the HuMATRIX group using a modified MatrACELL chemistry) and MATRIGEL®. Further, the functional protein groups in HuMATRIX were categorized based on cellular functions. In some examples, 674 proteins associated with molecular function of structural molecular activity were identified from the three extraction strategies, including laminins and fibronectin. In those examples, 90 glycan containing proteins identified from all three extraction strategies included proteoglycan, glycoproteins, biglycans, and phosphoglycerate kinases.

An exemplary placenta-derived matrix sample rinsed with water may comprise one or more proteins having GenBank accession numbers: A1YZL0, Q9UHS6, C9JKW4, Q6LEU9, E5RFD4, Q9UHT9, Q59F88, A0N4V7, Q6PB30, Q9BXY1, E9PSI6, C9JLE0, B4E2W7, D8MJ84, C9J430, Q01629, A6PVK6, B5M0Y2, Q96A10, O19525, Q969R7, B0UZ35, Q92494, Q5TBE3, Q6UWP5, Q9UF73, Q6LEN6, Q71RG2, E1Y3Y3, B3KS68, Q9H3C1, B3KSJ1, C9JB87, E7EU94, Q9P169, Q8WU39, Q6ZP25, A2RUQ5, B7Z515, Q8IZY5, P13645, D6RFZ9, Q71JB4, Q8N8E1, E9PAS6, C6GLW5, A2NZ55, Q8NBC3, E9PJF3, D6RBF7, Q4ZEJ2, Q5NV84, P01761, E9PS84, A1YZH4, Q5TBT3, B4DKX8, C9JF15, Q6YL41, D6RCN1, Q6ZNV4, B4DQC9, Q53GF3, C9J7P8, B7Z3P2, B8A4K4, B7Z5H5, Q5JYG5, Q9UL90, Q7L2U6, B7Z7E1, E5RII8, B4DEE8, B7Z8E6, E7EPH1, B1AMW7, E7ES61, Q8TDA6, Q5T7W9, Q99604, Q6ZP66, A8MQU8, P04264, B4DT64, E0CX09, E5RFW1, B4DZ50, B7Z2Y8, Q5T450, B4E0U2, E5RH38, Q6ZMC9, Q6XYB5, Q6ZNV2, B7WP14, P05413, E5RK96, E5RJS6, B7Z1F8, E9PEP2, Q8N1V5, D6RJG1, E9PRB0, D3DPE6, Q8IYA7, Q8N5M1, Q8NF12, Q96GA9, B4DGM4, B7Z1F7, B3KWM9, Q9H841, A0AVI4, B4E0C8, Q4W5L8, Q6PCB0, Q9H3W0, Q92567, Q5JU04, C3VNC3, E9PNQ0, B2BD34, Q93015, Q8NAT4, Q8IXR4, E7ENW1, B4DET2, B3KUU3, Q6IAN5, Q9BSD0, B8ZZY8, Q5JQQ4, Q8NAP1, Q9H6K5, A8MQ11, Q6ZNW4, O60721, Q6IRZ0, B4DI09, B4E0D3, E9PDA1, Q9UJC5, P30042, B7ZM74, Q96RY6, O15302, Q4VXJ3, B4DWN5, B3KST6, C9J586, Q9NPB6, Q9H6Q4, Q9UF83, B4E2Z1, D3DTX7, Q05CU2, Q8N589, D3YTD6, Q9Y3D8, Q8IZE8, E7ENV3, B7Z4R8, B2R888, Q5SQI7, C5H6K5, Q6ZV01, B3UYF0, Q06945, P08123, B4DLY8, Q9BPU6, B3KP95, Q6ZNC4, Q9H7V2, Q3B7T3, B4DV90, B4DUJ3, B3KSZ4, Q9BWN1, Q9BTQ8, Q9BYE7, Q86Y37, C9JZ88, B4DWU6, Q9Y5T4, Q68CJ6, P11766, Q5JPU0, Q10713, B3KSG5, Q8N254, B3KQS8, Q9NSI3, Q9BTU6, C9J6F7, A8MX39, B3KNL1, C9JF34, Q2UY09, B4DFR7, Q52LB7, Q86U33, A8MY71, Q6FHW5, Q8TBX0, B2RTS9, B4DVD7, B7ZMB3, B2R8U0, Q59H22, Q5SY01, B7Z8D8, B7ZLN9, B3KSU4, B3KWL2, B2RCK1, B4DVR4, Q5T0T5, Q68DS7, B1ATL7, Q59EZ0, B4DU33, P12724, Q8IYK8, B5A948, B2RAP6, A0PJX8, Q5TCZ1, B7Z8K4, Q53TX7, B4DHY8, Q53G16, Q92556, B4DMW0, B3KM38, Q6Y881, Q8NGI8, Q9H748, Q8WVL7, E5RHS6, Q6ZRS5, Q9NWR1, B7ZBI4, Q7L3S4, Q6ZMH4, B3KP66, B0V3L4, A6NNH2, Q9NZV8, E9PKC0, B4DZ79, P34982, B7Z609, A8K979, E9PEI6, Q08999, Q9BZ68, Q8N808, Q502V2, Q4ZHG4, Q9P206, B, 7ZKY6, Q5H9Q3, Q9NSM0, Q53G79, D6RCM8, Q8NGI4, E5RG31, Q96LT6, E7EPE7, A8K9P0, B4DR21, Q6ZS11, E9PCP1, Q6P5X8, P02452, Q9H7E9, P78517, B9ZVA0, C9JBF1, B4DUE5, Q9H7S4, Q99419, Q6ZUF6, B5MCV7, Q8IY16, B4DYB3, Q5TBN9, D9ZGG0, A6NJB7, A8KOM8, B3KSA0, Q6ZWL3, Q96Q06, E5RJA7, Q96ER9, A8K557, C9JGX5, Q9UJX1, B5MCB9, Q9H210, B4E338, Q6ZRP5, Q13596, Q59EW1, E9PBL0, A8MTL3, E7EU41, B3KXM9, Q9H6C4, B4DHA3, Q5FC05, O95484, B2R7K1, O15457, B4E186, Q5TCY1, Q0VAA2, A8MW61, E7EVQ7, E9LT28, Q9N2K0, E5RG82, Q6NTF9, Q4JNY3, E9PAV3, E9PCD7, B4DSN3, Q9UJT0, Q9Y661, Q8N506, B3KSP5, B7Z6J4, Q9NS40, C9JE72, P02461, B4DJN5, Q70Z44, A8MRT1, Q9UNY4, B4DSH1, E7EV41, Q9P2V4, P50553, A8K079, Q9HBH5, A6NCS9, C9JRP7, Q69YU3, Q9Y467, A6NEM2, Q86TV2, B1APR7, C9JT30, Q68E02, P01570, B2RDK3, Q9UHD2, B5A940, Q8I W90, B4DRF4, A8KA64, E9PDC8, Q8NFW5, Q8IYX3, B7ZLF0, Q6ZNE1, B4E076, Q6N089, Q6IPJ9, Q9H422, A8K9L7, B5ME58, A6NDL8, E9PLK8, Q6B016, Q92630, B7Z5J4, B4DYV1, Q4EYM8, A6NNA4, Q86TW2, Q8TF74, Q5LJB0, Q8IXZ2, Q7Z3R8, Q53V47, Q96JB5, Q68DE3, Q2KHM8, Q6ICH7, Q59GL7, B0QYY4, B3KS85, Q9BQF6, A6NCB9, Q9H1Y3, A8K434, Q96I00, B3KNF9, B2RNI9, Q8N2Q7, C9JMK7, B3KX42, Q9GZV1, A8K256, Q6ZP85, C9JYB8, Q14993, B7Z321, B4DQ54, Q7L8K4, P08908, B4DZ97, Q3LFD5, A8MY94, Q60I31, B7Z8X3, O43916, Q8WX69, B4DSQ7, Q8N7U0, B4DE59, Q5JWM1, P60509, B4DXW7, A8MW31, Q59FZ7, Q5H9F3, B4DS14, E3W980, P32971, Q96ML5, E7EUC6, B4EOF4, B4DJA0, E9PEH8, Q6P4R8, B7Z6I9, P30622, A4QPB0, B4DPI0, Q92917, B2R787, Q58F05, B9ZVP8, Q06418, Q14721, A2RRE8, P35527, Q68CX1, B4E3H4, B3KP32, Q8N0V4, B4DIM8, Q8TD49, B4DIX2, A8K8T9, A8K179, Q5JZY3, B4DG74, B7ZMJ7, B4DH30, Q9NRR2, Q9UF12, O94919, O43313, Q2HPN1, Q6P387, A0M8X1, Q6ZRR9, O60240, B4DZ16, A8K9U6, A7LFK7, Q9H7U1, Q8TBN0, Q6ZU65, B4DFK3, Q6NT55, Q8IVJ1, A0PJD3, B3KXW2, C9JVT2, Q9BSU1, B5MC00, Q96AC1, B7Z8M3, A9NIU4, O75131, B4DR01, D7PBN3, D3DXG4, B1ANH6, D3YTI9, B4E053, Q9NXL9, Q8NFU7, Q6ZU52, B4DF15, B1AKG2, Q59EW6, B4DDS3, B3KN02, P05997, P20807, B4DT66, Q59F77, Q92585, B3KX90, A8MUW4, B4E2K4, Q8NEN9, A6NCB3, Q92851, P37059, Q96RG4, C9JC37, A6NDY9, A7E234, D6W646, Q8NCN5, Q86WA9, E7EQF4, B0YIV3, Q6DT37, B4DHJ4, B3KVE5, Q86SE4, E2QRE6, B4E3N7, B4DS43, B4DME3, Q5T5C0, A6PVC2, O00375, Q0VDF9, C9J119, Q6V0I7, Q9P0G3, P30518, B7Z2V3, P25090, B4DU09, Q9H3S7, Q5NKU1, A8KAP0, B0V3L8, B4DRW6, P47989, Q8NCV1, Q13823, Q8NAT2, Q8N883, B4DIM2, Q9NS43, B2R6V9, O15398, Q5VTL7, Q96A33, A1X4P8, Q7Z5P9, Q16206, Q2TB12, Q8N7X0, C9JMG9, Q8N4C9, A6H8X9, Q4G115, B4DUG9, Q6ZT73, B0I1P6, Q15761, D3DTP5, B0I4X4, Q59GD4, A2A2Y4, B2RDY3, B5MCH9, P22736, Q09666, B1AJZ9, Q4VB88, Q14828, A8K8W7, Q96RK0, Q59F03, A8MTC3, B7Z544, B4DLR2, Q8NET4, A2A3C3, B4DTX1, B4DDQ0, Q9P219, Q5VST9, Q16187, A8MVM7, B3KXF6, B9TX55, Q49AJ0, Q8NCD3, Q96FV9, B7Z7L8, A6NCF6, Q9UMU8, Q5T197, B4E3J9, Q96EG1, B3KU60, Q9HCK4, Q15027, Q8N9N0, B2RCC7, Q96IF4, Q5VZL5, A2BF21, Q8IX27, Q12965, E7EPK5, B1AL46, E7EPZ1, Q5VU43, Q8NAT1, Q2UVF1, Q9UKN7, O75197, Q05D32, Q9C0D5, Q07157, B4DWE9, A6P4V4, Q8NGC5, A8K169, Q461N2, Q6ZSJ9, E9PP00, B7Z5S9, B0L3P6, Q03164, Q96AY4, Q8NEY1, Q2M2A3, Q16512, B4DLZ1, Q8IVL1, Q9UHR5, Q86XX4, C9JIP0, Q59G31, B4DM05, Q8NI27, Q2UVF0, Q504X9, E7EVK1, Q96PV4, Q59F90, B4DHQ7, A8K5W7, B7Z2U6, A8KAL5, Q96Q04, Q5VT52, A8K8X0, A8K602, Q8IVE3, P83111, Q7Z7G8, Q6RAQ8, A6NK03, P51843, Q5XG79, A8K5U8, B7Z217, B3KSR7, B4DLA5, B4DS80, Q08AD1, B2RTQ6, E7EMF0, E7EPZ7, B9EGR0, A3KN83, Q13395, Q8WXI7, P20929, Q8TF46, Q6PIA2, B4DHN9, O95396, Q12955, E7ESD2, Q7Z3C9, Q6ZVL6, Q8IZJ3, Q9HB00, B4E0H3, B4DRR2, Q6NV74, C9JXH6, E7EWN3, A6NJ88, B7Z4J0, Q09472, B3V8S3, Q7Z4F1, Q8ND99, B7Z8L0, B4DF48, A, 6NIB1, Q13315, Q14517, B4DHD6, B5MDQ0, B4DDR2, D2JYH6, Q9UEF7, O60237, A5D8Z7, B7Z646, Q9BZV3, Q06278, E9PGY5, A6NES4, Q4LE61, Q96M89, Q59EZ3, B3KV56, C9JAA8, Q5T848, B3KX29, B4DZA3, E9PBB0, A1KZ92, Q68BL7, Q8N1G0, P12821, E7ERE5, Q5JV73, Q68E10, P35240, Q6W4X9, B3KUY5, C9JLV4, B9ZVN9, E7EN67, Q8WZ42, B3KWU8, Q9P273, B4DZI8, B7Z4H4, P54253, C9JP98, Q8NF45, Q6ZND8, E9PEL0, Q99715, Q96QT4, B7Z879, A7E2D7, B4E043, Q8TEK3, O43157, B4E2Q7, E7EVF2, Q6UUV9, O95393, B7Z3S8, D3DUU0, Q9ULM3, D6CHF9, P39880, O60281, E7EUE6, B2RUU2, P12882, Q9P2K6, Q5VUA4, Q5JSL3, C9JMT9, D6W5S0, Q5IBP5, B3KXF7, P63136, O00186, C9JI46, Q6ZN90, Q9Y2Q1, B5BUA4, B4E0H6, A8K4A8, Q5VZ89, A8MVY7, Q9NR09, Q96IC2, B7WPK8, Q7Z479, Q9C0D2, Q96L96, O60287, C9J6W2, B7Z6K4, O60312, Q6ZNA5, C9JL14, Q5TBA9, P10745, B8ZZJ3, Q96KV7, C9JVJ3, Q0VDD8, B4E3F1, C9JBN5, Q6NUN7, Q96RL7, P78357, Q4G0U5, Q9BQS8, E7EN95, A7E2Y5, B4DK63, Q9HCM2, A5YM72, P0C091, P98160, Q6ZNI2, B3KWU3, Q504Q3, A8MQV7, Q9UIG0, Q5HYC2, B3KX52, O15230, B7ZLE6, Q8NA70, Q9Y6R7, Q10571, Q5T4S7, C0JYZ1, B4DSK8, Q8WXH0, D6RGV7, Q9BQG0, Q7LC53, B7Z3E3, A6NKC6, Q9UFD9, B1AMG5, P31629, Q9UDR5, B4DRI7, O75051, D3DSM4, Q19R18, B7Z9C5, Q9Y493, E1A689, O95714, E7EQE3, Q01118, Q13470, Q5YLB2, Q9P2P6, Q59H93, Q69YN4, B9EG70, P98088, Q8NDA2, P49641, Q9NTG1, E9PD66, Q8IVF2, Q9UMZ3, O75592, A4UGR9, P21817, Q5TCQ9, Q9ULL0, B2RU27, O60318, Q9UIW2, P42694, Q9Y6N6, E7EWP2, E9PBT7, Q68DN1, Q9NZR2, Q6IEH8, and O75445.

An exemplary placenta-derived matrix sample rinsed with a saline solution may comprise one or more proteins having GenBank accession numbers: B4DUX0, B2RDK3, B4E1U3, Q69YL0, A8MTC3, Q9UL32, Q9UIW0, E5RK96, Q9UNY4, B3KS99, E7EPZ1, Q5T205, B2RCH0, E9PJL5, Q86W28, E7EPC3, E7EVS9, Q9UPX8, Q7Z7G8, O75417, Q7Z5P9, A1L3A3, B7Z387, C93066, O14910, Q96EN8, Q29988, Q6YHU3, A0N4V7, Q9H2A3, Q02952, A6NHM9, B7ZLM6, B4E015, P58107, Q9HCL0, C9JTI1, C9JZ00, P55198, Q9UBC2, C9JI52, B4DVR2, Q9Y6X7, Q96NG3, Q8NET4, C9JVT2, B4DL55, Q5T9S2, O75962, E7EPD1, Q07343, Q9UP91, E0X084, Q8NFU7, Q96KC8, C9JMM2, Q9NVE4, Q6AW83, B4E0D3, A8K6A6, E9PJT0, Q8NF21, P49792, E9PBT7, Q96P03, Q9UEY4, A7E228, Q308M6, P08123, Q8NB14, Q6ZN14, Q9H4M7, Q9UF83, Q8WXH0, Q8N3S3, Q4LE43, Q8WYP5, E7EUV3, Q8IYB3, O15034, Q0VF99, Q59GG3, P22676, O95396, A6NL46, B4DP13, Q9UQ35, D6RA67, Q5TB93, B4DZ58, O60382, Q12955, Q9ULI3, Q9UHR5, O95393, Q32MM9, Q68DE3, Q6ZQY3, D6RCD0, A8K1T0, Q14DE1, Q5VVP1, Q30KQ9, Q9Y5G7, Q7Z4Y3, Q12845, P05997, Q14839, B1AQK6, Q6P387, Q0VAB1, A8MRT1, B4E2G5, D3DS91, P02461, A8K670, Q6UXY1, B3KV73, P12109, Q8IWX8, D3DUJ0, Q9UKX3, Q5VTR2, A6NNK5, Q15699, Q9H6A9, B7Z4S6, D6R9N8, Q8WXI7, Q2TAI4, B2RTT4, A5PL20, Q9NU22, Q92615, O00444, A4D209, A7E234, Q6PHR2, Q5SXX8, A8K586, B2RBM1, Q13315, Q9ULH0, P35527, B4E0M7, Q6ZSJ9, B9ZVP8, D3DNC2, A8KA05, O14715, B4DTU7, D3DSY9, Q9BZC7, Q8NEQ5, Q14517, E9PFR5, Q96LM6, Q9NR09, Q9BRF8, Q6PGP7, B4DHK0, Q59HB8, Q2TB12, O75592, P25391, C9J5R8, Q71F78, Q71RD0, Q13863, Q14573, C9J1J2, Q9ULG1, E9PDN5, Q9UDY2, E9PB92, Q9NUG4, Q8WUG5, B7ZLE6, B3KMS0, A8K5E6, B3KXM5, Q8IWP4, B4DMA7, A0FGR8, Q9H1H9, Q9C0D5, B4E354, C9J8P9, Q9Y6N6, A8K4A8, B3KSY6, D3DTX7, O60237, Q9NSY1, Q8TDW7, E7EWA1, Q96RK0, Q6Y881, B3KW47, Q86Y91, Q9NT68, E7EQE6, Q6ZNC4, P04275, O60281, O00555, P02452, O00368, Q96A33, Q9UG01, O15516, Q96MY7, A8K8N1, B3KP32, O75054, B4DZL6, P13686, Q4KN04, P0C091, E7ENN3, C9JE65, O94986, O94993, B4E1T5, Q5JSG7, Q8TF09, E7EPJ5, D3DRA2, E7ER60, Q68D67, B7WNR1, B4DX91, Q6AI02, A6NGQ3, E5RJA7, B7Z5I8, Q9ULJ7, B7Z5H7, Q4ZG20, B7Z7Y5, B3KUV3, Q5VVD7, Q13009, B1ARM6, A8MUU9, B4DUC2, Q9UGI6, Q6XYS1, Q9UBF8, Q08AL8, C9JLB7, B2RAH2, B7Z758, A8K337, Q8TBY9, C9WEQ4, Q9ULD2, Q13046, P20930, B0I1S0, C9JP98, O15213, E7ENL6, Q9NR99, A2BDK6, P16662, Q6STE5, Q68D39, Q9UKZ4, A8K8P1, B4E3V7, Q9BTC0, C9JAB1, P78363, O60287, E9PH44, Q6P4G0, Q8WVX5, C9JV64, Q08AE8, Q86XE3, B4DTT9, E9PFQ4, Q59FY1, A8MU01, A8K0B9, Q9NSM0, A6NK24, C9JZB0, B5MDL6, Q5CZC0, Q9NPG4, A0AUH1, O14936, A4D198, O60774, Q9NXC5, D2IYK5, B9EGR5, Q59EZ1, Q9HCU4, Q96JN8, A8MU99, D6RCM8, Q8N1E8, Q9C0G6, A5YKK6, Q96ER9, Q5JVT2, D3DSU3, B4DJ27, Q96BT1, F1B7C4, P20929, P15924, Q96GD7, O15245, A4D1E1, A8K604, Q6ZSZ5, O43157, Q9NQU5, Q9BS92, Q6P0Q8, Q9Y6R3, Q9ULH7, Q8TBW1, B3KW36, B3FL70, B0I1T1, B4E2U2, A2RUU9, E9PNE2, Q9NSI6, Q9C0A1, Q96Q15, B7WNU6, B4DMW6, B7ZM86, A4D212, Q659D1, Q96DC9, Q9Y4B6, A3KN83, B4DF15, E7EPQ3, B7ZLW5, P21817, E7EQE3, Q86V40, Q14139, Q96ME4, P02751, Q6MZM7, Q9PDX4, A4D0Q3, Q9HCJ3, B3KRS1, O14709, Q9H7D0, Q08AM8, B4DJG3, C9J3K0, Q8WVD3, Q9H4E3, B4DQJ6, Q6ZU65, B7ZMJ0, A6PVK7, O14686, B4DNI0, B7WP06, Q8IVL1, B3KPH8, Q53GA0, Q2TAZ0, E9PE71, Q6IPT2, E2QRJ1, B3KUB1, O60447, Q8IWU2, C9JXH6, O60293, Q6YHK3, A6NK89, A6NJB7, Q5TF02, O60671, Q5W026, Q4AC94, Q4G1A2, A8K9I5, Q9Y2F5, P16118, Q9P225, C9J2Y8, Q14865, Q59EE7, D6RFZ9, Q96K30, Q4ZHG4, I14993, Q5TZA2, Q9UPJ0, O60673, B4DYK2, P54756, E9PAV3, Q9BZ23, Q6ZQQ6, B4DZV0, D2JYH6, O75445, P12755, D3DX70, Q8N8H1, B4DRW8, Q15113, P29322, B4DHJ4, P22792, P52179, Q5W0C6, A6NKC6, Q6UWE0, Q9UQC9, D1CS68, Q5T440, B3KW72, Q9UPA5, P04264, Q8N9B5, B4DND4, B4DNB0, A8KA16, P63136, Q460N5, A8K6V7, Q96T58, B4E0H3, Q92805, B2RNB1, B5MCH9, E9PEB7, P21675, Q9UIG0, Q68DM7, Q9Y4G6, Q5SYB0, P53675, O94927, Q92621, E7EX20, B5MC17, Q9BYW2, C9J6P4, O15061, Q9P2P6, C4B7M2, Q68D69, P23471, Q59GE5, B4DIW8, A8K979, P06727, O14672, Q9BRX5, E7EQ84, Q9BXL7, P46013, P01701, A8K8C2, O75934, P39880, Q14789, B4E2Q6, E7EPY7, P11678, B5MDT7, E9PMZ5, Q96D60, Q9ULB1, Q6WG73, Q59FI2, B4DM17, P35658, P56703, E5RJH9, A8MPY4, B4DYQ3, A8K6X0, A5YM51, B3KTB6, P23284, B3KU97, Q5T1M5, Q6PJ25, Q8IVT4, A8K3I3, P0C7N8, B5M449, B7ZM78, Q8N2C7, Q8TEU7, Q6V017, A6NG74, Q96BA7, Q96PK6, Q8NBZ0, Q7Z3D4, C9J6W2, Q13085, Q53EY8, Q96AV8, E9PGN6, Q9NXL9, Q0VG55, Q5RKV4, A6NES4, Q12830, Q6ZTF9, B4E3S8, Q9H930, B2RAI2, Q4FD37, A2VCT8, A6NGG8, Q9NRJ4, Q9Y5J5, Q5T1B0, Q8IV32, Q99968, B3KWH7, P57058, B4DIX5, E7EVV2, B2RDN4, A8K024, Q14315, Q15149, Q5TCU6, D6RGG3, Q6NX55, E9PJP2, Q15751, Q86UB9, Q99419, A6NJ11, O15020, Q8N3K9, Q6X4T0, B4DG72, Q49AJ0, B4DQ39, P0CG42, B4E2D6, Q12768, Q8IZA3, Q6ZNV4, Q9H6R3, Q9BVR0, Q9BXA6, B7ZL07, Q9UMN6, Q8N307, Q8NDU6, Q6ZRT1, C9JWP3, Q9P2S6, B7Z4C4, A6H8W6, Q5SNV9, Q96Q06, B1N949, Q9P096, E9PB70, Q8NHQ9, Q9HBW1, O75095, B4DDX2, P60008, Q68DK7, O95714, B4DZ15, Q69YN4, B3KMB1, Q6ZWG8, B7ZW05, B1ALM3, Q5Y190, A8MUT5, B7Z3V7, O75949, O15294, B4DWD2, P13645, E2QRK8, Q70J99, Q7Z3R0, P47972, A2BDF5, Q0P670, Q9BUM6, B3KVV6, Q96S59, E2QRF0, B7Z5R7, E9PH94, Q9HBA0, Q5VXT8, Q8NEY2, B5A952, B5A968, B3KXD7, Q5T670, Q59GY9, D6RDG0, Q9UGJ1, B4DF35, B7Z1M3, Q9BSD0, A6NLU2, D3DVD8, Q14126, E1P546, Q6PGN9, Q59GS5, Q14690, A6NMZ7, O75376, Q8N808, B4DYH2, Q6UX41, P00748, Q0VDD8, B4DVQ2, Q8IU62, D3DS15, Q99855, E9PAJ9, B4DR56, P47901, Q9H479, A8TX70, B1APS8, P22670, D6RDI8, D6RC61, Q8N5C8, Q53G41, B4DGR3, C9J120, Q9UQC2, B4DZE6, Q9Y6D9, Q5HYL4, C0JYY2, Q12860, E7ESK8, Q8NFY9, B7Z8R9, Q76LX8, Q6T774, A9JR72, Q9P2H5, Q14754, Q711Q0, P12882, Q8NH94, Q15058, P78509, Q9Y217, Q569J4, C9K002, Q53SF7, Q8NFZ4, Q5T450, O95602, B4DYV1, Q8TEK3, B4E3E1, B4E386, Q8IYA7, Q99490, Q6N021, P32418, Q9P0K0, C9K0H8, B7ZCA0, Q14118, B4DKP8, P18463, Q8IZ20, P00629, A1L4K1, Q8NA90, Q9C0F0, Q5THJ4, Q01118, Q8NF82, Q5TCQ3, E5RI61, E9PEA3, D3DVL8, D3DUJ6, B4DQ44, Q15053, E7EUM8, Q96A46, Q9NZP6, Q08E86, A8K134, B4E3V4, B7SFD2, A8MVM7, A8K6D4, Q96PB7, Q5JPF3, B3KWW4, Q32M47, Q92625, Q8N1G0, B3KWX7, Q8NCJ3, D3DVG2, Q709C8, O14976, E9JVC4, E9PRC5, B4DYK7, B4DYL9, O75110, Q08AN2, Q68D65, A8K1E1, B7ZMI1, Q92851, A8K9K0, Q9NRC6, B7Z4E9, Q13233, Q96AY4, B4DEQ9, B1WB49, Q9Y2W1, Q59G51, Q8NG84, D6RI12, Q53H64, B4DNH8, Q9NYZ4, Q9NPN3, P35556, Q8N8I6, P98I64, Q06278, B7Z9A6, A0AV58, C9JB33, Q68CJ6, B2RBI4, Q5T4S7, A4KVA4, Q4G0N4, Q4JIW0, O95631, O15083, Q6ZNE9, E7EUA9, Q9H1L0, Q9UFI1, A8K547, O43861, A8K7Y5, P52756, Q8WYK1, B7Z6F7, D6R9G8, A0N4X4, A2JNH2, B4DZ97, Q8IVF4, Q9ULL0, A4UGR9, Q8NEY1, A2N0U3, P08581, B3KTN2, B7Z2Z3, O00409, B3KY30, A8K4L6, B4DZI8, Q6PL18, Q5T0I1, E9PL45, E9PDE0, Q9BUA3, P55072, O14776, O15550, E7EPH1, Q9C0D2, P02533, E0CX14, E7EUQ4, Q8NBS1, B4DJX6, Q96Q96, B1AL37, B2RTR3, Q6IEV9, A6NGY7, D6BP44, Q92879, Q05877, Q9UHN6, Q5T0B9, B1AND4, Q59EY7, Q8IVF2, Q96QT4, D6RC32, Q96A44, B4DX08, A8K2X8, Q8TCT7, Q7Z7M0, P04233, Q8TE56, Q9NXZ2, B4DMQ6, Q96M02, B3KW45, Q09666, Q32MC1, P17987, Q8N907, Q4QQJ4, E7ENI8, Q59F51, E7EUR0, Q2VIM1, P21815, D3DSA9, Q8NDL9, Q9NU19, Q6P2Q9, B4E0I2, E9PIW8, Q59GZ9, B3KXH9, A8K4T6, Q9ULG6, B3KY42, Q2LD37, Q12934, Q05D32, E7EPK5, Q8ND61, B7ZKV0, O60522, O00418, D3YTC3, Q9P2A4, Q12769, B4DWJ2, Q00535, B9EG70, A5D8X7, E9PJQ0, A4PBF7, Q5TCZ1, O00232, Q2UVF0, Q5VZL5, O43272, A6NML8, Q8N799, B2R5Q0, E7EMR4, Q9UK58, Q5VVC0, B4E0K2, B4DDI2, Q8N4W9, O75131, Q9NX95, Q6PRX2, B3KY47, O95678, A8WCD8, P32519, A2A3N6, B7ZM08, B4DDK4, B3KMT7, Q6YL45, Q569K6, B4E1T1, B7Z503, E2QRD0, Q9UIW2, E5KRP6, Q8IW48, Q5LJ98, E7EUY0, E9PFC1, B4DF69, Q58F08, A7E2V4, B9EGA7, Q9Y6R7, Q59FZ7, B4DEX5, P51810, B7Z1R7, Q8N7X0, Q13332, B4DR53, C9J221, O14980, E1P5P8, E9PDP9, Q8TBT6, B3KUG1, Q6PJF2, B7Z3N1, Q8IWZ2, E9PD66, A6NHH5, Q8IYI6, Q96G03, B4DQA6, A5A3E0, B4DRF9, E9PDM8, O43566, Q9Y499, Q5H9F3, Q13574, Q96IW2, P41231, E7ESD8, Q9P2D1, B3KVI2, O15063, Q86YR5, Q8NAT2, E5KVZ4, B7ZME9, B7WNX6, C9JPS0, A8K8U5, Q8TCX5, Q05707, Q9UPR3, Q5U651, B7SXT2, O19731, F1C627, Q16140, Q4W5D7, C9K0J2, Q96P91, D6RIA8, Q562R5, Q5JVA1, Q16812, Q6WBF6, Q68DD0, Q8IZV4, Q5IKE6, Q8WVV1, B2RAF7, Q5T1S8, C9JRV6, Q96PA1, Q8NAM7, Q6ZRD3, E7EQ97, E9PS84, O14889, Q5FBY7, Q9HD52, E5RIE1, B2RDF7, Q71RG2, Q19UJ4, Q8WWH1, C9JJ97, D6RAY4, D6RFW6, Q9C084, C9JAF1, Q5W186, Q5THN1, A2KLM6, Q9BXD8, Q59F88, B4DWC6, A0N8V1, E9PJ78, Q658T3, D6R9K0, B7Z8Z1, B4DKX8, Q5T5A1, D2JYI5, Q5QR42, Q53QZ9, D6RHV8, Q8WVE7, A4Q9H0, Q96S09, Q6GMQ8, E9PLB5, E9PSI6, D3DTG8, Q9UHS6, Q96T62, Q8N943, Q6ZTI0, E5RFM1, Q9NP26, B6ECA9, D6R9F2, Q13982, Q8NF18, D6RBL9, Q9P1H3, Q2NKK6, B7Z8E6, D3DPD0, B5MCS2, Q5SZR7, B7Z9I7, Q562Z4, O00246, B1AQ54, A1YZH4, E9PFR4, Q5VXS2, B4DKI5, B3KP07, E5RGN4, O75360, B8LFN9, Q9BUL9, A2NH54, B1AVV1, Q8TE87, Q5JV94, Q8N589, B0QYJ0, D3DT85, Q6IAN1, D6RDK6, Q6ZPD3, Q969R7, Q9P1M5, A8MV81, P56385, E9PNY2, Q8NDS2, A2N2X0, P30273, E9PPQ0, Q5ZGK7, Q6ZTZ2, Q92799, Q9ULC0, E9PFF3, Q6ZQQ9, D6RBJ0, B1AJW0, D3DNY4, P15291, Q8TBE2, B4DRU7, Q16663, Q8TAS2, B3KNQ5, P62841, E7ENW1, C9J1K6, Q5NV70, Q6UXH0, Q14569, Q96GE9, A2N0S9, B3KP10, C9J5N9, Q5JXJ0, B4DIN4, Q56VW5, Q562R7, Q562R4, Q562L6, Q5U0H7, E5RGJ5, Q8TCY0, Q8N1E2, Q9Y643, D3DS92, B2R4K1, E9PH25, Q6P462, E7EQ21, Q59FK5, Q96EK6, Q9BYN0, P0C6P0, P33240, Q49AT5, Q6UXV6, A4DI16, A6NDX4, Q9P206, B5BUM4, B9A015, B7ZAA5, B5MCR4, Q9H1C9, Q4W5I2, E9PRF8, Q1PHJ7, B7ZKQ8, B9A064, B3KT27, E9PCK1, Q8IZP5, Q29702, E2QRP4, A6NKF2, A4UCR7, E9PR98, B3KUD5, B3KV50, P34910, Q9BTF3, E9PKK9, C9JP65, D3YTD6, Q4JM63, A8MYI2, Q96B26, Q5T1J1, A6NCN8, D6REB2, A8K4G3, E7EUS6, Q5JWQ0, Q0P611, Q59ES1, B4DNV4, Q8NE86, C9J421, Q59EW3, B3KWI5, P10153, Q6UVW9, Q8N2P5, Q07820, A0PJF7, Q13846, A0N5G1, D6REQ2, Q5T5M1, Q5T187, B4DZZ4, E7ENN2, B4DZM5, E5KNQ5, B0ZBE8, Q8N143, Q96GL9, Q8NAQ8, E5RG51, E9PCE4, Q8N7A6, Q9P0C3, Q9Y2S2, C6GLW5, E7EPR5, B3KN16, A6NMT0, C9J1K8, A2IPI1, B3KNJ1, E7EPV6, C9JEE2, B4DQD2, E9PPY5, B4DSF0, Q8NBC3, Q05BI1, Q9H7E9, O15551, P14543, Q12984, B4E390, Q53TL7, Q6MZH0, Q9NWB3, B4DGV5, B4E2M5, Q5JPT9, B2R701, B7Z5R5, Q9Y628, P01722, E9PK17, B4DXX1, D3DS02, B4DZG6, A6NK03, Q5NV84, B3KTU1, A6NDL8, Q6ZRD0, E9PH89, B3GVC1, Q6IAN5, Q9P1Q5, O00485, Q8N3F9, B3KMA9, B4DUN6, E5RID9, Q8IW14, E9PLB3, E7END7, E7EQA4, C9JND4, Q9NTB5, P55283, A6NFT5, O60542, A6NNJ1, D6RB11, B4DQC9, Q63HM5, B4DFL3, P61803, P07498, Q6NUK7, A8K171, E9PM02, D6RIE8, E9PR90, Q9H2K0, P62072, Q59FP8, B4DTW7, B4E1L1, B7Z2G7, P15090, E9PKB7, Q96AL6, Q9UBM4, Q69YU9, C9K0G3, Q8N9X3, B4DU14, Q5VXX5, B3KTR0, Q5JTF2, C9JEL4, Q6W762, D6RFH1, Q8NET5, Q8WW34, A8K6C6, A8MXJ8, Q96RD0, B5MEB3, B4DH60, A7UHG6, Q9BVU5, Q6ZS02, A6NFC9, E5RII8, Q8IXZ2, A6NKH4, C9JDX2, B2RAW0, C9JPH0, Q9H4T6, Q9H8M1, Q9GZU3, B4DQ82, Q9BYB2, E9PP46, Q2A122, Q580X0, B4DNJ9, B4E140, E7EVT6, E5RG91, A4D2F6, B7ZM17, C9JHZ3, Q8N6K4, A8K750, Q5W0G6, B4DNN8, Q6FI30, Q8N7M0, Q5VWW1, A8JZY9, A8MVW5, Q30KR1, B7WNJ9, B8ZZ71, P10696, Q5SZW9, Q96RG4, B4DFI9, Q8NEV9, D2CFI5, A0A575, A6PVM9, A0PJX8, A7E1W7, Q14031, B4DTY4, Q6W4X9, A8MT84, P0CG12, P13985, Q6ZP66, B4DJU0, Q659D3, P28074, B4DXN2, Q9NWT7, A8MYG4, Q9UI66, B5MD06, E5RGT8, P46379, Q8WYW5, A6PVL3, Q00403, Q14773, Q9GZS3, A8K051, C9IZA2, Q96QS0, B4DZF5, A8MQD1, A8K9U0, Q7Z6J0, B7Z8X2, E3W989, B9A062, B4DPI0, B2R6N6, B2RXJ1, Q59FM2, B3KXN9, B3KRJ7, Q99946, B2CNW3, Q96IK1, Q6PCB0, B4E3B1, Q6ZNJ0, Q6NUK7, E9PJP1, B2R8U0, E7EMU0, P0CG20, B5MEE9, A8MPY1, B5ME88, B4E0B3, B3KPI0, B4E0X3, D3DT59, E7EQZ4, Q4G134, A6NGQ5, Q59EZ4, B5MDP5, Q8TAG5, E9PSH8, Q9H1K4, Q7Z2T6, O94887, B1AJV4, Q96EH3, C9J6P7, P0C7V9, C9J6I7, Q9H6B4, A4CZ08, Q59FL0, B7WP14, A8MXU7, P05413, Q7Z4K6, Q8WU02, Q8WYG7, Q7Z679, B4DIU8, B2RAP5, B1ATL7, B2R9R8, Q6ZML0, Q6ZUC2, P06733, B3KS81, Q7Z4H2, B7ZKK1, B4DKI6, B4E2R3, Q4W5T8, Q6ZTI6, B4DXX8, A5PLM7, Q6ZNA3, Q8NHB5, B4DP75, P53582, Q8NDR0, Q9BXJ0, Q9GZP8, B4DJ32, O43924, P21781, P54792, B3KX63, B7Z5L7, B4DPF5, Q5JT82, A8K2G9, Q9NWV7, Q8N9S9, Q9NQ27, B4DZC5, Q71RC2, A8K854, B4DI84, Q96G61, Q9UQQ2, P56696, B4DQQ3, Q5VZD9, B7WP59, Q4L180, B4DPA3, Q96PU9, Q9Y3Q4, C9JJ91, Q8IY50, D6RA51, Q9UKD1, D3DUP4, B3KU60, E7ET07, B4DP74, E7ES41, Q7Z469, Q06643, P59190, B5MD13, Q6LEE7, P02008, Q59EI9, E7ERR0, B4E3K9, C9JHU6, Q6UQL6, A6NEV3, B3KQ72, E9PDA1, D3DT02, B4DYX5, C9JBG8, C9J8T6, A6NJ97, B3KP31, B7U472, D6W5X5, B7Z974, Q9NPG6, Q96B67, A8K3X7, B3KRR7, Q8WZ87, B7Z3V8, Q9H6K5, B4E223, Q8N9V6, E9PNI1, Q4VKH8, P0CK97, Q6ZS11, Q6ZP25, Q59G62, Q6NUL7, Q9H6B9, Q5SZK5, P59095, Q59GG0, B5BU16, B4DJV0, C9WCV0, B4DND6, O16743, Q9Y6N3, B4DKU3, Q8N2E6, B4DKM6, B1B0G8, O43822, A4D1W8, D6RHD2, Q12778, Q86YW5, Q8N8Q2, Q96RY6, E7D7X9, Q9N2K0, B7WNY2, O95685, Q9NSV5, B3KQG4, Q96G91, Q59GA9, A3KGN5, Q4W5I3, Q8TEM1, E9PCD7, B4DER7, Q53G09, E7EQ81, Q75MP2, B4DDW9, Q3SX64, Q8WVP5, Q14DE0, E7EVQ7, Q8N8W4, Q08345, B3KV77, Q9H0L4, Q6NZ36, B4DPD3, Q9UNM1, B3KTX8, Q4G176, B4DQD7, Q75ME3, Q9BY10, A8K359, O75112, B4E2T4, Q8IXR4, Q5U649, O60664, A6NDD5, Q8IYY5, B3KP85, A0PJB2, Q5JWQ5, B8QFA1, P49279, Q8TDB4, Q9NXR1, Q10586, O95682, C9JL12, Q9BZM3, Q6ZUX3, B2R7X3, Q8N8T1, Q01991, Q6PKB8, E7EPM4, O14986, B2R8C2, Q9H726, Q9C0J1, C9JAU4, Q53FP3, Q9BZF3, E5RHF2, Q2UY09, O95503, P25101, Q53G16, Q6UWY2, Q7Z4V0, Q1KSG2, Q9P104, O95447, Q6FI03, Q9GZU5, C9JBQ5, Q8N5Q1, B8ZZY8, E1NZ95, Q9H6F5, Q9UI36, P06241, Q8N0V4, Q96AH8, Q8WYI2, P10070, P41134, Q96HA1, P85037, B1AHE3, Q96C74, C9JG27, A6NJK0, Q6X959, Q9GZN6, Q6B014, E2QRB7, O43439, Q9Y467, Q9NSI3, Q3LRJ5, C9JGT3, B4DFZ3, Q50KP5, A6NEF1, B2R5H0, B4E331, B4DMW0, Q2M1V8, B9ZVT8, B4DRZ0, B4DF86, Q9H0D2, Q8IZF6, B3KWK0, C9JKP4, Q96IF4, B3KWU8, A1A5B4, A0A539, E9PC86, Q8N7Q0, A6NEM2, B4DFV4, A6NLC8, B7ZLN9, Q6N083, E9PBB0, B5BU44, E7ER46, A8K3V4, B4E093, D6RIU4, Q9H760, A8MVZ5, O15302, B4E233, C9JGC2, E9PBW7, C3U395, B2RNZ7, Q5JV98, P14678, B4DET4, Q15452, P07339, B9EGI0, B8QIL9, Q9BZE3, Q8IYX2, P51841, Q9HCM3, B5MCN7, A8MTI9, E7ENC5, Q13426, Q15G98, Q9UGF6, Q76L88, Q96NY8, Q9NX01, O14939, B4DDV4, P19387, Q9NXJ0, Q02505, Q32MK0, Q71RB6, E9PBL8, Q9H4T2, B4DUU7, Q9NQ34, E7EXB9, Q14872, E9PAT2, O95848, B4E1J8, Q02779, B7ZLK0, P30301, B9EKV4, B4DKH5, B4DYQ5, P43146, Q9P1L6, A6NFN9, B7Z2U3, Q96BA4, Q6IQ23, E9PHM5, B0S7Q4, B3W6H0, B7Z4Z4, Q7Z6K3, Q5T593, Q8TB74, Q96NE7, Q6WRI0, P49190, Q5MNZ9, E7EQ48, Q6NT65, E9PN78, E1P506, Q56NI9, C9JSR0, E7ENE9, B2R850, B4E3V3, B4DIM5, P01185, Q9HCC9, B7ZB77, Q58A55, B7Z3E3, B2R6M6, B4DQ58, O15195, Q6PJU4, Q9H967, B4DLQ1, B3KN64, E7EVY2, Q9NW52, Q86XT9, B4E285, O00716, P39060, B4DXM2, Q1T7F6, B2RXG1, A6P4T4, Q96IZ7, Q5T3J3, Q6ZWE6, P22105, Q7Z3A5, B4E3B3, E1P5K4, Q6L8P0, Q96BF6, B9A6M7, Q71RC7, Q1MW40, Q8IWW0, A9JR48, B5BU25, Q96I80, Q3BBW0, Q2TB96, B4DU99, Q9HD36, C9JAE6, E7EPM3, Q8N7P3, Q5BN46, C9JWB7, A6NM42, Q8N9S8, Q9GZV8, E7EN67, A8MUV4, O43422, O75290, B5MDE5, Q6IAL2, Q9BYT4, Q8TAM2, B4DYB9, Q8IZS6, Q8IYD1, Q9H224, E7EME2, B4DFU0, Q659F8, Q96FV0, B3KTH9, B7Z5R0, O96013, Q9NX47, B4DYV6, Q86YQ0, B4DZA2, C9JY06, B4E3J9, D3DPU8, Q64LD2, P18505, B5MDL1, Q14940, Q86U25, Q1XBU6, B4DRT3, B3KT12, B7ZMF6, Q96J71, B4DPB2, B4DKE7, B7Z8Q6, A8K3T2, Q96BT7, Q9NWG5, O95954, Q8N461, Q8N3J6, B4E0F7, B3KTP9, B4DUR3, O60285, Q9H8T8, Q9NWP3, Q9BQF6, Q8WXI3, Q8NGY2, Q86VR7, A7MBN2, Q6ZQT2, Q8WVV4, Q9H5V8, Q7Z6V5, Q8N6U2, Q9UHF1, E5RHD4, Q8N204, B4DNL5, Q765P7, B4DDT1, Q8NH63, B4DH14, Q5SQQ7, Q96JM7, O00257, Q9UKJ1, Q9Y349, Q6EMK4, B3KXQ5, B7Z6A6, Q6P461, B7Z5H9, Q8WVF5, Q6NSD0, E7EMY1, D6RCR1, Q9H2Y7, B7Z7V3, Q8NCT1, Q5T1R4, B7ZLJ1, A8MX39, Q9UP83, P78524, B4DUV4, D3YR72, Q9H0E9, C9JU50, C8YBG9, B3KNM3, Q86U33, B4DLC7, B4E1I8, B3KS12, B4DKT9, Q9NRC1, B3KRW2, Q8N9S2, Q6UXH8, E7EUQ1, B4DZH5, A8K466, Q9H422, Q14694, B2R7J8, Q6P453, C9E1F2, Q69YM1, B7Z3Z7, P42338, P57082, Q6ZVM7, E7EWW8, B2RA91, B4DVD7, Q9BTA0, Q6ZSE7, Q6P995, Q5JT02, Q53HT3, Q14BN4, E9PHH0, D6R9F0, B7Z436, Q8WXX7, Q8N5S0, A8MTU8, Q5SY01, Q8N5I3, E9PDF0, Q52LC2, E9PM46, B4DQX0, A8K5F6, Q6ZUB1, B7WNV3, E7EQ57, Q3ZM64, A0PJ61, B2R9R6, Q96D88, B4DF11, B4DPJ2, B4DK04, O14627, B4DX15, P48067, E9PEN5, B4E1W0, P16066, Q86TT8, B4DSW6, B4DKN1, Q16206, B3KTB9, D2IYL3, B7Z7M9, Q2TAY7, E7EV27, B4DZH7, E9PBB6, B7Z3K3, Q9NR30, B7Z896, Q6IN85, P01031, Q59GP4, A8MQV7, B2R5T7, Q9Y3M8, Q5T321, Q8NEL0, B2RAP4, B4DSI9, A8MWT1, Q12879, P50895, B7ZAW7, Q9UFZ4, P35908, Q5JRA6, Q5TCC5, Q9UKF5, A2RUK8, Q53GI3, A8KAP0, Q17RW2, Q8NGL2, B3KQC5, Q9NP50, Q4JNY0, A6NEK1, Q8IUS5, Q8IZP6, Q149P0, B7Z3I2, Q16720, A6NND1, Q59FS7, Q96JP9, Q9Y566, B7Z6J5, Q5TCH7, C9JPZ2, A8K5S3, B4DTZ3, Q60FE7, C5HU01, A8MU33, Q8WY44, P08F94, A8K9U4, B7Z7G5, Q15661, B4DF77, Q5VTL7, Q4G0M0, B2R6J0, B4DJD0, Q9BZZ2, B3KU14, Q6MZK7, Q86UR5, P48735, B1ARF3, A8K9G7, B4DMK8, Q2M1Z3, Q3SY90, Q5JZG9, B4DHY4, A0AVI4, O95835, Q59H63, B4DDK8, Q9NYT0, Q9NZN1, Q969S9, Q8WVL7, Q15942, E9PP00, A8MUV8, P09497, P25054, O77932, Q8NGN1, B9EIS6, E5RHS6, Q9HAP2, Q5VYS4, E7ERW8, Q8NGX3, A2BHY8, Q8NHB1, Q9BRP9, E7EWN9, Q8NHA2, Q8TB96, B3KPN8, Q2HXV7, P26368, B7TY16, Q93015, B3KPD3, Q86YV3, Q6ZRW4, Q9H2G2, Q5BJF5, Q0PW94, B4DYY5, A8MQD0, E9PBW3, B7Z508, B4DX63, B7Z2Z8, Q59GL9, O76039, Q9NS37, A2BF26, Q96G38, B7Z856, Q6ZN12, Q8NFZ8, B7WPJ3, E9PNZ4, Q9BYV9, D3K197, B3KRD6, A8MQC0, P43403, Q6P5X8, P57057, Q53F81, A8K807, Q3KPI9, B7WNK7, Q7L8C5, B3KX68, B4DDC8, P33316, Q9HBG5, Q659D6, Q70E73, Q9H8P0, E2GIM6, Q8NDP0, E7ER45, B4DI51, C9J9Y7, A5YM43, A4D160, A8K2D6, B4DYF3, O95837, Q9NS56, Q4W5Q4, B4DV54, Q59GC2, B4DQ54, Q9UBT3, Q96LT6, B2RCB4, O15218, C9JJA2, C9J551, Q75LS7, B4DYT7, B4E164, A8K9D8, O75467, Q8WWF5, Q5FBW8, B3KV79, Q9UBF9, A8K0D4, O14929, Q8NBB4, Q12884, Q6ZMQ8, Q9P218, P23468, Q5TCX8, B4DN07, A6NJ88, P23467, Q92610, Q5CCG6, Q5SQ64, P48553, B7Z951, Q9UBL0, C8CAP4, Q9NXX9, A7KAX9, Q9NZ08, Q13535, B9ZVA0, Q59ET3, C9JBF1, Q5EBM0, Q59G66, Q8NGV5, B4E1B7, Q05BY4, Q8IV03, P17600, Q8TDW5, P41217, Q9BZV3, Q96CM8, B3KM81, A8MRT3, Q504R6, Q67FW5, Q8N9G5, D6RBD3, Q5JPI2, B7Z3K0, B2RCH4, A8K169, P00451, Q8N0S2, Q5TBT3, C9J4W8, O15389, E7EP05, Q93086, Q9UNI1, Q12836, B5MC15, Q149N0, Q13946, P16473, O75475, Q92539, Q96NI6, Q9UNX4, A8K8R5, Q8IVF1, Q8TDS7, Q1RMC9, Q9UHG0, Q9BZ68, B7Z611, A8MQ72, Q5T7Q5, B4DI09, B2RDY3, D6RIA3, Q01804, O95817, B7Z1Q8, B5MDD8, Q86TV2, Q6ZRC1, P03999, B4DKH1, C9JCH2, E7ETA2, B3KPW1, Q9UN75, Q6IA17, E9PH21, Q9UGT4, Q86V48, B4DR97, P11021, Q17RP2, Q05CU2, Q6PIA2, E9PPL0, B4DWS6, Q0VF96, Q14008, B3KPF6, E9PHX5, D3YHM4, A8K7Y8, P49736, E9PJ76, B2R8Q2, D6RFK8, Q5IRN2, Q59FP3, Q9UJX1, Q8NEZ4, B4DRF4, O00763, A6NFE0, C9JTA7, Q6NUS1, Q9HCD5, Q5JPT5, Q59GL7, B4DSR9, A8K615, Q8TCJ2, B3KNM6, B4DYB4, Q6ZMN3, B4DWN8, Q9Y576, B4DT65, Q9BQS8, C4WYH4, Q5T5P2, P58304, Q6IFI9, O95789, A0AVI5, Q9NVV9, B4DK02, Q6ZVT6, Q969F2, A5D8W1, B4DNFT6, B7WNL6, Q7Z554, E9PGN2, O60669, Q569I7, Q494V5, Q15142, B0UZ11, Q5JTA5, B4DME9, B7Z6N7, Q9P2K6, Q86V35, Q9HC10, Q8N9N0, B4DEA6, Q86U90, Q3SXY7, Q96G74, B7Z9C5, B3LEU8, P53420, Q9BT57, B4E0V1, Q9NPG3, C9JSC3, E7EVA0, B7ZL69, Q9UFD9, C9JG58, B3KWB5, Q9HCE6, B4E2W6, Q5T8R8, Q8NCU4, Q96JX3, Q9HCU0, Q92911, Q6FGY5, O60478, Q9H6X5, Q6ZMT4, Q96LA9, Q8NHC1, Q6XP50, Q9H7V2, Q5SQI7, B4DUG9, Q96BP3, C9JG87, Q24JR0, Q5VSZ0, P20749, Q6ZP01, Q9H3M0, C9JM76, Q6P0M4, Q08266, Q8TBB7, C9JFW8, E7EPX9, Q96JG9, P05546, B7ZMF2, B0FP48, A8KAL3, Q8TCJ6, A8KAM8, Q6PEW0, B1APH4, B4DHI0, Q8N7H9, Q2HXV3, O95125, Q14330, C9JK83, P54826, Q66GS9, Q96A73, Q49MI3, Q6ZT21, Q96B77, B3KWI6, P83111, B3KQS9, A8K6Q8, Q0P6D9, B4DZR3, Q5JWQ6, Q9Y6K8, Q4VAP1, B3KRK2, Q7RTU8, Q8N4F4, Q3B820, B3KN02, Q9MY63, Q96LX7, Q5SRE5, Q9NPH3, Q9ULR0, Q8IV53, Q9NRU3, Q8N9W8, E9PEF0, Q7Z6A7, P23634, B4DYM6, A5PKW4, A6NIT3, P54257, Q8TD26, O15033, B2R8D7, Q9P291, Q9Y4D8, O95680, E7ETI5, Q8NGR3, B4DU15, Q5T985, Q969F9, Q70Z44, B4DHJ9, P29475, A8MSQ6, Q9NR45, Q6ZMU0, Q14721, B, 7ZLP5, B4DPW6, P78367, P50553, B7Z5S9, Q9BXF6, Q17R88, Q14767, B2RCI6, D3DUA9, E9PS97, C9J022, B4DW89, B3KTK9, Q9Y6Y1, Q5VZY9, Q7RTN0, A7BKA4, Q13586, B4E120, Q8WUD6, Q9NWW7, Q14C87, A4D2G3, E7ERT5, B4E2H7, Q8N450, B3KXW2, Q8TF64, Q8N2G6, Q01954, B3KP71, B7Z3V5, Q9Y239, B4DK45, P55895, B4DRB7, Q9H9E3, A8K0P8, Q8TC92, Q8ND23, B3KPQ7, P22314, P27987, O60487, Q9BV10, C9J3V6, Q2QD20, Q5SZL2, Q86WZ0, A8MZF0, A0PJE2, A5YM74, B4DU92, B4DF54, C9J4J4, P01024, B7Z2Y2, Q9H4L7, B4E184, Q6N090, Q8TBF4, Q86XX4, Q9BYI3, O95155, B3KVX6, Q5SYW2, Q9BX66, Q3SY77, Q8TDM6, Q8NHH1, Q8IY92, B7ZLC8, Q5VT97, Q5VYV7, E9PBS6, P41594, Q53FJ3, O14657, B5ME67, B3KNZ1, B4DTD3, P35573, B4DQW4, Q6UUV9, B9A6L3, B3KXX3, Q96MC4, Q2V2M9, Q6ZNJ1, B4DG21, O94988, Q53F65, B4DRW6, B3KS46, Q53RT3, Q8IZM8, Q17RE6, Q53FX3, B7Z4Q9, Q8IV39, B4DT93, Q9H6M6, B4E0F4, Q2M3T9, E7EWK2, B3KSA0, Q59GD4, Q9UH90, Q8IZJ3, B7Z5J4, Q6ZR03, Q4EYM8, Q8IXS2, O43318, P33908, Q6AI59, B4DSN3, B4DEA4, A1KZ92, P22304, B4DL80, A8K6R5, A8K8C1, Q8WYT0, E7EQZ2, B4DF27, Q15650, E9PQN2, B7Z4E2, Q9BZF1, B3KX45, Q0D2N5, Q6ICH7, Q96FN5, Q5H9Q3, B4DS32, P42263, Q53TQ3, Q8N5S1, B3KTC9, Q92953, Q59FP5, Q5T362, Q5W0G0, Q86UW8, Q59G80, Q9HBE4, Q9NXY1, Q6DSU6, P48357, B4DS95, B2RNI9, Q8NGI8, Q9C0D4, D6RJG0, B4DU18, Q15262, Q14028, Q8N7X4, Q6VU67, Q96CH6, A6GV77, A6NCQ9, Q6ZP85, P51508, Q8N7A7, O94805, B3KNF9, P23352, Q8N5U0, Q86VP3, Q5TYJ8, P26006, B5MDT1, Q9Y6R4, E9PIC5, E5RJZ3, B4DFY7, B9EK55, B4DEY3, A8K8Z0, Q9UP52, B9EIL8, Q4W4Y1, Q9ULD9, Q8TCT3, C9JUK7, Q6M1B8, E7ERL4, A8K9S1, A5D8Y4, P28069, B4DH93, O43304, Q17RG1, Q6UVK1, D3DWL9, Q9UBG0, A6NKQ7, B4DGT7, A6ZGF9, B3KRD4, E9PFY8, Q9BX95, Q6A163, O95450, Q96BH1, C9JVN5, Q6UX07, D3DRN4, O43749, P27815, P41250, Q14677, Q96PL2, B3KUX3, B7Z747, B7Z831, Q13474, Q8TD57, C9JJ54, Q53EU2, A8K5B8, A7LFK7, Q9Y250, Q5JWM1, Q6RJV8, B2RB90, O95359, B4DU20, Q9NSB2, B2RAL3, Q5JSM3, B3KMC6, B3KMT1, B2RCL0, P32971, Q9NZ56, Q9BZJ7, B4DR50, Q9H2U9, Q14929, B7Z445, Q56P03, Q9NR48, O14917, B4DSA8, O60309, B4DLR8, Q9Y3A2, Q09472, P16298, Q08945, Q6ZU52, B1ALY6, Q13151, A8K215, E9LCZ2, Q8WXS8, Q5VU97, O14926, B5BUA4, P26232, C0KWF0, A4D1S0, Q8NGC9, Q7Z4N2, Q8N7R7, C9JLV4, B4DZU9, D3DN97, Q9NSE7, Q5JR59, B5FX47, Q7L576, B4E1N9, P03986, B3KU91, Q8WXP9, Q6UXM1, P17026, Q02846, B2R604, Q05C41, B7Z5L6, E9PIC8, B4DI23, B3KUP6, Q96PQ0, O75828, B3KT58, Q7Z3N6, Q12965, Q92502, O75157, B5MDQ0, Q96F46, Q149N8, B4DGW1, B4DLS9, Q96AD5, A8K5G6, E7EWW7, P51692, P01023, B3KTW2, Q8N344, B4DIM8, E7ET19, Q7Z2Y8, C9JU34, E7EUM9, C5MN97, Q6XZB0, Q9NWR8, Q9Y5Q9, Q5VTT5, P11137, B4DJT3, B4DX95, Q9UBH6, Q76G19, Q8NEF9, Q9NY72, P0C7U0, A6NKB5, Q9BYP7, Q8WWJ7, Q8NCN5, P78357, Q8NDH2, B7Z7T2, Q9HBD1, E9PEJ8, E2RYF6, Q3B7A3, Q6IS01, Q7L5N7, Q6TFL3, O43641, P45974, C9JNC2, A6NLE6, Q9C0E4, O75132, Q6VB86, C9JLF8, B4DSM3, Q9HBB2, B5MC00, Q15849, P47736, Q8IWY7, P35398, A7MD48, C9JGI3, A8K2N3, P22736, Q969G3, Q4VC10, Q96JC4, Q6ZRI0, A5YM72, B4DZ19, E7ERH3, D6R905, Q6ZR08, E9PDI6, A6NP61, Q9UHV7, B4DU96, O95067, B3KXA2, O15398, Q14032, Q304Z4, A2VDI6, E7EV52, B4DUV2, Q305M9, B7Z4U6, B3KX90, E9PB08, P78559, Q8NBE8, Q9Y2V3, A8K143, P09327, Q9P2G4, B7ZLW7, E9PGN7, P50748, Q96JP2, B7ZLT7, Q86UE3, Q9Y6X8, B4DPP5, Q59E99, Q8N5C6, P10745, Q96K37, P51825, E7EM83, Q14CN2, Q6P9F7, B7ZL90, Q14781, Q9UHL4, E9PIR9, B4DVG5, Q504Q3, E7EVK0, O60312, A8K5D9, A6NEL2, Q9UMQ4, O75197, Q562E5, Q53EV6, E7EPG6, Q5FWE3, P49815, P18146, Q8N350, B4DSM6, Q5VZB9, Q13576, B5MEA1, A6NLI5, Q16832, C9JS33, Q8TD55, Q2M3R2, B4DG58, A0S244, Q68CR7, Q59H05, Q9Y662, Q9UEF7, A8MUW4, Q86UH7, Q5NKU1, Q59G50, E7ES80, Q659A1, E7ERF5, Q9UN71, B2RB53, B9EGE4, Q13049, Q3LFD5, E3W980, P04198, B4DSH5, C9JTQ0, A8K0Y1, C4P098, D3DQM9, Q2VY69, Q9NYZ6, E9PAU3, Q53ET2, B4DN13, P59044, A8K559, B4DF48, B4DWG1, P54317, Q9BYH2, B4DLX6, C9J6U6, B4E0E9, A8K2N0, B7ZML3, B4DSX8, Q6DN72, E9PBK0, B4DGA3, P30530, O00378, Q9H9L3, B3KSE7, A8K2D2, C9JHD2, Q6MZW2, Q7Z3K9, Q6ZND3, B3KN68, Q8N6Q8, Q9NRK6, Q13972, Q06481, Q5FYA8, Q6ZPD8, B4DR59, B5B2N8, B4E2H9, Q8N6G6, P35568, Q16187, O95876, E9PCA6, Q9NV58, C9J1E9, Q59EX7, Q8TES7, Q6AZW6, Q96Q11, A5YM41, O43854, Q8TEF4, O14529, B8ZZJ3, B3KXR0, Q96EK5, Q59H30, A6NK97, A8K617, B4DSY1, Q8HWS3, Q13224, D6BZU5, Q5JSL3, Q6UWJ1, Q2VPK5, B5MDV5, O60346, C9JC32, B7Z7E7, A6NLQ9, E7EMW7, Q86X06, Q59EI2, Q69YRO, QOP6H9, Q7Z350, Q5TCQ9, Q8TDV5, Q6P597, O94885, B3KXK2, Q6RI45, D3DP12, E7EP12, Q4EWT1, C9JCN0, P35579, Q96L50, E7ETY2, C9J1I5, QST0U2, Q53TA0, P0C7T5, A8K0E7, Q6ZT16, Q8IUX6, Q16760, Q8NGC5, P51531, Q15147, Q08ER8, C9JCC7, B3KXW8, Q9UKN7, P51828, Q17RV3, Q5T3U5, Q9C093, B8ZZX6, B5MD83, B4DWM4, B4DFU8, O15027, Q8NHP8, Q14678, B3KNV5, Q9Y4D7, B4DGA8, P58397, Q06418, Q96MD2, Q9P2K8, Q6Q759, B3KX86, Q6UB99, B7Z7W1, Q68CP0, Q9P2P5, B7Z7Y3, B2R5U1, O95226, Q53GX1, O75295, Q2VPA4, A8MTP9, B0QY77, Q9H347, Q86UK0, P78362, Q9UF71, Q14DR2, O76081, Q9UKK3, B7Z217, Q96T83, Q9H816, E7EPB6, Q5SXM2, O75366, Q8IW70, A4ZI32, Q53HL0, Q8TDT8, P20061, E5RJQ4, E1P541, B4DKZ7, Q9P2F8, Q96F44, O15047, B4DFU5, E9PFC2, P17032, B2RAN0, Q8NFU0, O15230, Q6ZSR9, Q53SW3, Q9BTG3, D6RTK6, A8K9Z8, B7ZMI0, C9J112, D3DS86, B4DI49, A6NEM4, P09172, B7WPH3, Q8IVE3, O96028, Q5VWN6, O94910, Q68DS0, A6NDR9, B2R708, Q2NLA0, Q8IYU4, Q96RL7, Q13017, E7EW28, O43520, Q8IVU1, Q8TD84, A6NIR3, P98198, Q6NX52, Q9UBC3, A6NCI8, Q8IZF3, D6RBT4, Q8N9H8, Q92576, D6RDY7, Q59GI4, Q6ZMR1, O94806, P82987, Q16825, B3KS49, Q9NQA5, Q8NFM4, B4DFD6, E7EPU5, Q8IVF6, Q86Y38, Q5TGY3, Q02224, E5RIM3, O14830, Q13634, B3KUX7, Q5HY54, E1P5G4, A6NP11, O15015, E7ENU4, O14981, B7ZLZ2, A8K1Z4, D3DUU2, Q6ZU69, Q7LBC6, Q8TDZ4, Q7Z6G8, Q96JK9, Q9BUD9, P35523, Q8NBH6, B7Z3H9, Q6PKG0, Q6ZMT1, Q2M2A3, D3DSF5, Q5TCS8, Q9H7F0, O60374, E7ENM8, Q7Z6E9, Q9UK61, Q9UPV0, B4DZF0, Q96JQ0, P11047, E9PG22, Q9NZJ4, E7EWM0, Q14CL3, B7Z7X4, B3KW69, Q6ZRR9, B2RNT9, Q8IUA7, Q96PE2, B2RTS2, Q9Y232, Q76NI1, Q6ZUA9, A4PB67, Q15283, Q5C9Z4, Q9NZR2, A8K330, P11215, O43151, O60449, Q8N556, Q8TCN5, P46531, B7Z904, E0CX08, B4DF22, C9JY66, Q7Z401, B3KPN9, B7ZLJ8, B3KWW9, Q6IEH8, Q9NRD8, Q5TBA9, B3KMB8, B4E3N7, A0AVI2, Q7RTY7, and E7EUN6.

Orbitrap mass spec was further used to quantify the relative abundance of the major ECM proteins found in HuMATRIX rinsed with water relative to MATRIGEL® (FIG. 1).

Other growth factors were also identified by mass spectrometry, including intracellular fibroblast growth factors iFGF-12 (linked in myocardium of the developing heart atrial chamgers and in developing soft connective tissue of limb skeleton and linking ribs to vertebrae) and iFGF-13 (found in myocardium of developing heart atrial and ventricular chambers and throughout the peripheral nervous system and the developing central nervous system as an intracellular modulator of voltage-gated sodium and calcium channels), insulin like growth factor-2 (IGF-2, a major fetal growth factor that also promotes fetal pancreatic beta cell development and stem cell differentiation), of EGFL-7 (shown to play a role in repairing ischemia-reperfusion injury, regulating vascular tubulogenesis in vivo, promoting endothelial cell adhesion to the ECM and angiogenesis, inhibition of Notch signaling in HUVECs and neural stem cells, and may promote immune system escape), and bFGF (FGF-2, found in the basement membrane and linked to formation of new blood vessels, and shown in vivo to protect the heart from injury associated with a heart attack, and further noted as a critical component for embryonic stem cell culture to maintain the cells in an undifferentiated state).

To quantitatively measure of the amount of residual DNA present in the samples, a picogreen assay was conducted. As a control, a piece of decellularized tissue and a piece of tissue pre-decellularization were also digested. 25 mg of the resulting lyophilized material was dissolved in 1.03 ml of proteinase/1×TE buffer and incubated at 55° C. at 1200 rpm for 3 hours. Following incubation, samples were applied by standard addition method. 200 µl of each digest was added at various volumes of 1×TE and gDNA spike. 100 µl of samples are then applied to a 96 well microtiter plate followed by 100 µl of PicoGreen dye was added to a 96 well plate and read on a fluorescent plate reader (settings of extinction 485 nm and emission 538 nm). As shown in FIG. 2, there is around 95% reduction in DNA in each of the placental ECM samples. Enucleation was confirmed by histology sections of the decellularized placenta tissue as stained by H&E (FIG. 2).

Example 5: Culturing Cells on or in Placenta-Derived Matrix

To test the ability for adherent cell types to adhere directly to HuMATRIX, a standard serum-free cell attachment assay was performed. Human adipose-derived mesenchymal stem cells (ASCs) were grown in 37° C. incubator in DMEM media supplemented with fetal bovine serum (FBS), and antibiotic antimycotic (ABAM) to have about 70-80% confluence. Cells were fed the day before assay. 48 well plates were coated with approximately 200 µl of CELLSTART® (fibronectin with human serum albumin), MATRIGEL® or HuMATRIX in triplicate for each time point (15 min, 30 min, 60 min, and 120 min) and allowed to dry overnight. As a control a group of wells were left uncoated. The next day, 200 µl of 2% BSA was added to the coated wells and allowed to incubate for 30 minutes at room temperature. After 30 minutes, the wells were washed with Hanks Balanced Salt Solution (pre-warmed to room temperature) and not allowed to dry. DPBS and 0.05 Trypsin set out to were pre-warmed to room temp. Media was removed from plate and the cells were washed twice with PBS. ASCs where dissociated with trypsin and with the trypsin inhibited with soybean Trypsin Inhibitor. Cells were re-suspended in DMEM (no serum) and counted to deliver $1.5 \times 10^3$ cells/well. The cells were incubated on the respective matrices for 15 min, 30 min, 60 min, and 120 min, and any unattached cells were removed by washing with PBS. The plates were fixed with 4% paraformaldehyde for 10 min and then stained with crystal violet for 5 min. Each well was washed with four times with $dH_2O$ to remove any remaining crystal violet. The number of cells in each well was counted manually by image capture under microscopy and using ImageJ64 software.

Adipose derived stem cells (ASCs) attachment in Serum Free culture media was tested in a cell attachment assay using ASC. ASCs were placed on CELLSTART® (fibronectin with human serum albumin), MATRIGEL® or placenta derived matrix (HuMATRIX) coated culture plates or culture plastic in serum free media. The attachment kinetics were determined at 15, 30, 60 and 120 minutes. Each of the two lots of the placenta derived matrix (HuMATRIX) group showed higher attachment at all-time points as compared to CELLSTART® (fibronectin), MATRIGEL®, or culture plastic alone. The typical morphology of ASCs was observed as grown in serum free media at 1, 3, and 7 days.

Adipose stem cells were also cultured in serum free/xeno free conditions and tested for metabolic activity after being catheter injected in a 6 French cardiac catheter along with HuMATRIX, using Alomar blue to assess viability. 100,000, 200,000 or 400,000 ASCs were delivered onto a culture plate either with a pipette, in a catheter with media, or in a catheter with 1 ml of HuMATRIX that were premixed and passed through 6 French cardiac catheter. The viability of the cells delivered was assessed over 3 days morphologically and by Alamar blue. Alamar blue (1/10th volume of media in well) was added to the samples and allowed to incubate for 4 hours. After 4 hours, 100 µl of each sample was loaded into a 96 well plate and fluorescence was read at 570 nm (excitation) 585 nm (emission). There was no significant difference in cell viability of adipose stem cells grown on CELLSTART versus the HuMATRIX.

Example 6: Culturing Dorsal Root Ganglia (DRGs)

The ability for ectodermal cell attachment and growth on HuMATRIX was also assessed using dorsal root ganglia (DRGs). Near 100% attachment of DRGs was observed on HuMATRIX, Laminin, and decellularized placenta with urea extraction, but nearly no DRGs attached to culture plastic alone, with the cells stained for beta-III-tubulin and DAPI to assess the cell morphology. Cells grown on HuMATRIX only showed a more developed phenotype with ganglionation observed, as also seen by light microscopy, with Alamar blue metabolic activity of DRGs on the various substrates including 8 batches of HuMATRIX showing minimal differences among ECM coatings, yet near zero activity with DRGs on culture plastic alone.

To further assess DRG culture on tissue engineered HuMATRIX, YFP expressing DRGs were isolated from 7 day old pup and adult mice and plated on HuMATRIX, coatings and electrospun fibers and compared to DRGs on MATRIGEL® and on PDL coated glass coverslips. DRG media consisting of neuroblast media, B27, L-Glut, antibiotic antimycotic (ABAM) was added to each well and the plates were incubated at 37° C. Media was replaced in wells every three days and new media was created every 7 days. Forty-eight well plates were coated evenly with 200 µl of the amino acid polymers Poly-D-lysine (PDL) and incubated (closed plate) at room temperature overnight. In the following day, remaining Poly-D-lysine was aspirated from the wells. The wells were rinsed, and allowed to evaporate. After evaporation of the wells, the wells were coated evenly with gels of HuMATRIX, and MATRIGEL®. Wells containing PDL only were used as a control. Approximately 500 µl of DRG media was added to each well. The plate was placed in 37° C. incubator overnight. Any remaining (non-attaching) cells were washed off the next day. For 14 days, DRG outgrowth was examined in each well under a fluorescence microscope. Length of neurite extension was measured using ImageJ64. There was significant neurite extension observed in well coated with the HuMATRIX. Dorsal root ganglia grown on HuMATRIX and MATRIGEL® experience a significantly higher amount of nerve fiber extension than the control plates (PDL). Average DRG neurite extension length was comparable to that of MATRIGEL®.

Example 7: Culturing Human Primary Cardiomyocytes and Cardiomyocytes Derived from iPSC Cardiomyocytes were also cultured on the HuMATRIX as a second mesodermal cell type with matrix-dependent attachment. Human primary cardiomyocytes were seeded at 20,000 cells per well on Celprogen extracellular matrix coated plates in serum free/xeno free conditions. After culturing the cells for a week, they were transferred to various substrates, including HuMATRIX from three different lots, 0.1% gelatin, tissue culture plastic, and MATRIGEL®. At day 1, 3, 5, and 7 cell viability was measured using alamar blue. There was no significant difference in viability of cardiomyocytes grown on the various xenogeneic extracellular matrix coated plates compared to the HuMATRIX.

Additionally, cardiomyocytes derived (differentiated) from induced pluripotent stem cells (iPSC) were grown on 4 lots of HuMATRIX and compared to gelatin, fibronectin, MATRIGEL®, and culture plastic. iPSC-cardiomyocytes rapidly attached to HuMATRIX, yet few cells initially attached to other matrices, and only cells on HuMATRIX where contractile at 1 day after attachment (2-3 days for other matrices). iPSC-cardiomyocytes also had a distinct morphology on HuMATRIX relative to culture on other substrates, including fibrinogen. These cardiomyocytes were encapsulated in a large 3D hydrogel disc (around 200 microns thick and 8 mm diameter), with the cells viable and contracting inside. Further the iPSC-cardiomyocytes synchronized 1-2 days sooner on HuMATRIX relative to other substrates, and were shown to electrically couple by monitoring calcium transients by electrophysiology.

The electrical coupling of cardiomyocytes is confirmed by a modified patch clamp electrophysiology assessment of iPSC-derived cardiomyocytes culture on HuMATRIX for one day in culture. Calcium transients are represented in color shifts, with individual cells numbers and traced with respect to time, with a movie recorded of the intensity modulation display, recording the Fura-2 ratiometric dye reporter shown to excite at 340 nm and emit at 380 nm. All cells are seen to synchronously produce calcium transients and/or contract, thus indicating that a syncytium has been generated in this culture system.

Example 8: Culturing Hepatocytes on Placenta-Derived Matrix

Hepatocytes were tested as an endodermal cell for growth on HuMATRIX. Human hepatocytes were shown to exhibit classic morphology on HuMATRIX, akin to a MATRIGEL® over collagen sandwich culture, and superior attachment to MATRIGEL alone, with cells grown either atop of or inside of the HuMATRIX hydrogel at day 1, 3 and 6, as emphasized by an actin stain at day 6 to accentuate the low attachment for MATRIGEL® groups relative to HuMATRIX. Furthermore, the urea concentration in the media for hepatocytes grown on the various substrates showed the lowest level in HuMATRIX, suggesting faster hepatocyte culture adaptation via a quicker anabolic-catabolic metabolic shift.

Example 9: Overlaying with Placenta-Derived Matrix

Hepatocytes are harvested and cultured on a dish or well. Solutions of placenta-derived matrix at various concentrations (0.5, 1.5, and 3 mg of protein/mL) are prepared and mixed with culture medium to prepare overlaying medium. The prepared overlaying medium is kept on ice. Each of the overlaying medium is added into the dish or well on which hepatocytes are attached and cultured. The dish or well is returned.

Example 10: Culturing Pancreatic Beta Islet Cell Line on Placenta-Derived Matrix Coated Plate A vial of rat Rin5f islet cells (ATCC; CLR2058) were thawed by gentle agitation in a 37° C. water bath (approximately 2 minutes) and transferred to a centrifuge tube containing 9.0 mL complete RPMI 1640 medium (ATCC 30-2001). Cell suspension was spun at approximately 300 g for 3 minutes, and cell pellet was resuspended with 5 ml of complete RPMI 1640 media. 15 µl of cell suspension was added to labeled eppendorf tube along with 15 µL of 0.4% trypan blue. About 20 µL of 0.4% trypan blue cell suspension was pipetted onto the slides and total cell count per replicate/group determined using a cellometer (Cell count: $1.51 \times 10^6$ cells). 10 ml complete RPMI 1640 media was added to cell suspension, and 5 ml of cell suspension was seeded onto three T25 culture flasks at a density of 20000 cells/cm². Cells were incubated at 37° C. and 5% CO2, and medium was replaced every other day. Rin5f cells were grown to reach 70-80% confluency (~7 days), and culture medium was removed and discarded from T25 flasks. Cell layer was rinsed twice with DPBS (−/−) to remove all traces of serum, and 4 mL of Accutase was added to T25 flasks. Cells were observed under an inverted microscope until cell layer is dispersed. 3 mL of complete beta cell medium was added to cells/Accutase to deactivate and cells aspirated by gently pipetting, and cell suspensions were transferred to 50 ml conical tube and 7 ml of additional complete RPMI 1640 medium added per flask. Cell suspension spun at approximately 300 g for 3 minutes, and cell pellet was resuspended with 5 ml of complete RPMI 1640 media. 15 µl of cell suspension was added to labeled eppendorf tube along with 15 µl of trypan blue, and 20 µL of the trypan blue cell suspension was pipetted onto the slides and total cell count per replicate/group determined using a cellometer (Cell count: $4.5 \times 10^6$ live cells). A 48 well plate was coated with 40 µl of HuMATRIX (2 Lots) or Matrigel in sextuplicate. Plate was incubated at 37° C. and 5% $CO^2$ for 2 hours. $4.8 \times 10^5$ live cells were respun and resuspended in 25 ml of complete RPMI 1640. 48 well plate was removed from incubator, and 500 µl of cell suspension was added to each well at a density of 20,000 cells/cm2. Tissue culture plastic without any further coating of an ECM is used as a control. Cells incubated at 37° C. and 5% $CO^2$. Complete RPMI 1640 media was replaced every 2 days. After 3 and 7 days, the cell morphology was examined under microscope.

The pancreatic beta islet cells grown on different matrices as described above were stimulated with glucose according to the following protocol: surgery.wisc.edu/system/assets/354/Islet_Glucose_Stimulated_Insulin_Secretion_Assay-.pdf?1264176115. Then, c-peptide (insulin) secreted by the cells were measured using c-Peptide EIA Kit (Sigma-Aldrich; RAB0326) and its manufacture's protocol (sigmaaldrich.com/content/dam/sigma-aldrich/docs/Sigma/Bulletin/1/rab0326bul.pdf).

Example 11: Culturing Pancreatic Beta Islet Cells in Placenta-Derived Matrix $3.6 \times 10^5$ Rin5f islet cells were respun and resuspended in 1.5 ml complete RPMI 1640. 0.5 ml of cell suspension resuspended in 0.5 ml of HuMATRIX (3 unique Lots) and MATRIGEL. $7.2 \times 10^5$ live cells were respun and resuspended in 1.5 ml complete RPMI 1640. 0.5 ml of cell suspension was resuspended in 0.5 ml of HuMATRIX (3 Lots) and MATRIGEL. 120 µl of cell suspensions with HuMATRIX or MATRIGEL was added to wells of 48 well plate sextuplicate. Plate was incubated at 37° C. and 5% $CO^2$ for 2 hours, and the 48 well plate was removed from incubator and 500 ul. Complete RPMI 1640 was added to each well, and the cells were incubated at 37° C. and 5% CO2, and complete RPMI 1640 media was replaced every 2 days. After 3 and 7 days, the cell morphology was examined under microscope and observed colony formation. Further, the placenta matrix could be used to cryopreserve these pancreatic islet cells, and thus likely other cells types. $3 \times 10^6$ Rin5f cells were frozen in either placenta ECM alone, placenta ECM+10% DMSO, placenta ECM+10% DMSO+10% HSA RPMI alone, DMSO alone, HSA alone, and combinations thereof per FIG. 14D. Cells were control rate frozen to liquid nitrogen storage temps and stored for one month before thawing and subsequent live/dead cell counting. Cells cryopreserved in human placenta matrix along with DMSO showed a 2× increase in viable cell numbers compared to cryopreservation in the standard freezing media of RPMI with 10% DMSO, and a 4× increase in viable cells when the placenta ECM with DMSO is further supplemented with 10% HSA, as compared to the gold standard cryopreservation method, Low Rin5f cell viability was seen in other single component cryopreservation systems.

Example 12: Culturing and Differentiating iPSC

Pluripotent induced pluripotent stem cells (iPSC) were preliminarily tested for growth and differentiation on HuMATRIX. IPSC cells were grown in mTeSR 1 or mTeSR 2 or Stemgent xeno-free and serum free media were passaged on MATRIGEL® to adapt the cells to feeder free culture and to remove contaminating feeder cells. The cells were passaged with dispase or TripLE onto wells coated with HuMATRIX, and nanofibers of HuMATRIX, where cells were observed to attach and remain pluripotent at 7 days of culture as determined by Tra-1-60 staining. A population of clustered cells were observed to be attaching and embedding in HuMATRIX nanofibers, with positive TRA-1-60, and growing as colonies growing attached on gels of HuMATRIX.

The ability to drive the differentiation into the three germ lineages of endoderm, mesoderm, and ectoderm was also tested. iPSC were clustered into embryoid bodies and attached to either HuMATRIX (PlacBMsup), MATRIGEL® (MG), or gelatin (Gel), and compared to basal expression levels of the founder fibroblast lines used to make the iPSC (F13 fibroblasts) and the iPSC (F13 plurip iPSC) cells in the pluripotent state. The plastic plate without any further treatment was also used as a control. RNA was extracted using Trizol and primers for sox1 and nestin were used for measuring relative gene expression in ectodermal differentiation, Actina2 and brachyury for measuring the same in mesodermal differentiation, and Sox17 and FoxA2 for measuring the same in endodermal differentiation. The expression levels of the samples were compared to basal expression levels of the founder fibroblast lines (F13 fibroblasts) used to make the iPSCs and to iPSC (F13 plurip iPSC). HuMATRIX was observed to upregulate genes in each developmental lineage beyond the levels induced by culture on plastic or on MATRIGEL®.

Example 13: Culturing Umbilical Vein Endothelial Cells (HUVEC)

To examine if the HuMATRIX contains the components required for endothelial tube formation in vitro, human umbilical vein endothelial cells (HUVEC) were seeded with 500,000 cells on a T75 flask and cultured on tissue culture plastic in Medium 200 media supplemented with LSGS for 6 days. After 6 days, the cells incubated with calcein AM diluted in DPBS to have a concentration of 2 µg/ml for 30 min. After 30 minutes, the cells were trypsinized and then transferred to 24 well plates pre-coated with various substrates (HuMATRIX, alginate, gelatin, MATRIGEL®, and Geltrex®) at a density of 100,000 cells per well. 500 µl of media was added to each well. About 16 hours after plating, the cells were examined under a Zeiss microscope to look for endothelial tube formation under GFP. Endothelial tube formation was present in HUVEC cells pre-coated with the four unique lots of HuMATRIX, as on the MATRIGEL® positive control, yet lacking vasculogenesis on two-dimensional culture on tissue culture plastic alone.

Example 14: Biocompatibility

To assess in vivo biocompatibility of HuMATRIX, a mouse subcutaneous injection assay was performed to compared HuMATRIX hydrogel and sponge vs. MATRIGEL® injected through a 18 ga needle subcutaneously. Implants were left in place for 2 weeks and the body weight and general health of the animal was monitored, with no adverse events noted. Upon explanation the injected materials were located and then excised along with the overlying skin and underlying muscle for histological analysis by H&E. H&E showed MATRIGEL as relatively inert and poorly cellularized at 2 weeks whereas the HuMATRIX gel and sponge contained cells throughout the implanted graft. The implants were further stained for M1 and M2 macrophage markers to identify the cells as either pro-inflammatory (M1) or remodeling (M2), using CD68, CD206, and CD86 antibodies (data pending validation in February). H&E staining of the implants showed that higher cellular infiltration with no apparent encapsulation were found for placenta derived matrix groups relative to MATRIGEL®, although xenogenic human placenta derived matrix was implanted into mouse.

Example 15: Delivering Placenta-Derived Matrix

Further testing the ability to deliver HuMATRIX in vivo, the hydrogel was injected into rat myocardium following induced ischemia (myocardial infarction) as compared to saline injection. Rats were given myocardial infarctions by ligation of the left anterior descending artery (LAD) of the heart using 5-0 suture, with blanching of the heart and subsequent echocardiography used to confirm the infarction. The injected hearts were excised at 8 weeks and analyzed by optical mapping for any difference in cell electrophysiology activity in the at risk ischemic region using a langendorff chamber. The heart was also stained with TTC and fixed in formalin for embedding for H&E and Mason's Trichrome to analyze myocardial wall thickness and scarring between the groups. By optical mapping, on average the saline treated groups lost the ability to conduct electricity (arrhythmia) out of the at risk region when the stimulatory electrode was placed in the infarct region below the ligated LAD, where only 1 or 2 of the 5 given electrical stimulations could be recorded in a distant patch clamp whereas typically all 5 pulses were recorded in HuMATRIX injected groups. Overall, 5 of 7 animals given saline injection died within 2 weeks post surgery, whereas 5 of 5 HuMATRIX injected animals survived through 8 weeks. Comparing the change in pre-surgery ejection fraction to 8 week post-op, a 56% improved ejection fraction was noted in HuMATRIX groups in this pilot study. These results show safety of injecting human HuMATRIX into rat myocardium, which support feasibility for using this human ECM hydrogel for possibly delivery cells within this matrix as a putative therapeutic in heart disease and other diseases.

HuMatrix was biotin conjugated according to Biotin labeling kit instructions. Myocardial ischemia was induced as described above in two rats. Biotin labeled HuMatrix was injected into treatment sites in ischemic regions of the left ventricular myocardium. Thirty minutes and one hour after biotylated HuMatrix injections, rats were euthanized and hearts were harvested for sectioning and histological analysis. Hearts were fixed in 4% paraformaldehyde, flash frozen in optimal cutting temperature compound, cryosectioned and mounted on slides. Adjacent serial sections were either stained for collagen with Sirius Red or were for biotin with FITC conjugated Streptavidin. HuMATRIX gelation was evaluated based on presence of both collagen staining and biotin staining in serial sections.

Sirius Red (Direct Red 80, Sigma-Aldrich, St. Louis, Mo.) and Fast Green (Sigma-Aldrich, St. Louis, Mo.) were dissolved at 1% wt/v in 1.3% picric acid. Sections were incubated with Sirius Red for 20 minutes, washed in phosphate buffered saline (PBS) and incubated with Fast Green for 10 minutes and washed again prior to permanent mounting. Sections for biotin staining were also stained for cardiac troponin I and counterstained with DAPI. Samples were permeabilized with 0.25% Triton-X100 for 20 minutes, blocked with 4% bovine serum albumin for one hour at room temperature, incubated with a mouse anti-rat cardiac troponin I antibody (Abcam, Cambridge, Mass.) overnight at 4° C., washed in PBS with 0.25% Tween20, and incubated with a goat anti-Mouse Alexa Fluor@ 546 antibody (Life Technologies, Grand Island, N.Y.) and Steptavidin-FITC (eBiosciences, San Diego, Calif.) for one hour at room temperature. Coverslips were mounted with Vectashield HardSet mounting medium (Vector Laboratories, Burlingame, Calif.) and slides were maintained frozen at −20° C. until imaging.

Eight weeks after surgery, the animal was anesthetized with 2% isoflurane and injected with 5 ml of heparin, and surgery was performed to excise the heart. The heart was then explanted to a container filled with ice-cold tyrode (128.2 mM NaCl, 1.3 mM $CaCl_2$ ($2H_2O$), 4.7 mM KCl, 1.05 mM $MgCl_2$ ($6H_2O$), 1.19 mM $NaH_2PO_4$, 20 mM $NaHCO_3$, 11.1 mM D-Glucose in deionized water, pH=7.35±0.05) solution and was connected to a custom made cannula. Cold tyrode solution helped in arresting the cardiac activity until it was connected to the life support system and prevents deterioration. The cannulated heart was Langendorff perfused with fresh Tyrode solution and then transferred to the experimental setup, where it was perfused and super-perfused with Tyrode solution at 37+/−1° C. The Tyrode solution was aerated with 95% $O_2$ and then pumped at a rate to maintain a pressure of 50 to 60 mmHg in the heart. Once the contractions stabilize, about 10 microliters of voltage sensitive dye, Di-4-ANBDQBS dissolved in 10 ml tyrode solution was injected close to the cannula and recirculated for the rest of the experiments. Few minutes after the dye perfusion, 30 µM solution, either 2, 3-butanedione monoxime (BDM), excitation-contraction decoupler, was added to the tyrode solution to remove any motion artifact.

The optical mapping system used has been described in detail previously in ncbi.nlm.nih.gov/pmc/articles/PMC3469699. Briefly, a red laser (650 nm) directed by a dichroic mirror illuminated the heart, which excites the voltage sensitive dye and fluorescence was emitted. The fluorescence beam was filtered by a long pass emission filter (715 nm) of wavelength 715 nm, which was finally recorded by a high speed CCD camera. The camera has acquisition rate of 1000 Hz at 80×80 pixel resolution.

Tissue processed through decellularization was collected to confirm cell removal by H&E, with 10% neutral buffered formalin fixed sections sent to DePaul Medical Center (Norfolk, Va.) for embedding, sectioning, and staining. At the conclusion of optical mapping, hearts were stained with triphenyltetrazolium chlo-ride (TTC). TTC dissolved in PBS 1% W/V replaces the tyrode solution. The heart was perfused with TTC for 15 minutes and preserved in formalin for sectioning. The hearts were then sliced every 2 mm from the apex to 2 mm above the suture. Serial heart sections were embedded in paraffin, sectioned, mounted and stained with Mason's Trichrome and H&E by VCU Pathology Services (Richmond, Va.). Example 16: Metabolic stability screening 96-well plates are coated with the placenta-derived matrix prepared as described above. Hepatocytes are plated in the 96-well plates in hepatocyte metabolism medium (HMM) at a concentration of 35,000 cells in 50 µl per well. 50 µl of HMM samples with and without two times the concentration of the test article to be evaluated is added to each of the wells. The plate is incubated at 37° C. for multiple time points (for determination of $T_{1/2}$, the time period leading to the disappearance of 50% of the parent test article) or, for screening purpose, one single time point (e.g. 30 min). Acetonitrile is added to terminate metabolism. Centrifugation is used to remove hepatocytes and cellular macromolecules from the supernatant containing the remaining test article. LC/MS/MS quantification of the parent test article concentration after incubation is measured by the following formula:

% Remaining=[(Concentration after incubation)/(Concentration before incubation)×100%

In vivo hepatic intrinsic clearance is further calculated from the $T_{1/2}$ values as an initial estimation of the rate of human in vivo hepatic clearance of the new chemical entity in question. The correlation between in vitro human hepatocytes and human in vivo results is improved by considering not only the rate of metabolism, but also protein binding and intracellular uptake.

Example 17: Hepatocyte P450 Inhibition Assay to Evaluate Inhibitory Drug-Drug Interaction 24-well plates are coated with the placenta-derived matrix prepared as described herein. Hepatocytes are plated in 24-well plates in hepatocyte metabolism medium (HMM) at a concentration of 250,000 cells in 490 µl per well. 5 µl of HMM samples with and without one hundred times the concentration of the test article to be evaluated is added to each of the well. The plate is pre-incubated at 37° C. for 15 minutes to allow interaction of the test article with the hepatocytes. Same 5 µl of HMM samples with and without one hundred times the concentration of the test article to be evaluated is added to the same well, and the plate is incubated for 30 minutes. Acetonitrile is added to terminate metabolism, and centrifuge is used to remove cellular macromolecules. LC/MS or HPLC quantification is performed for drug-metabolizing enzyme metabolism of the substrate. The P450 isoform-specific substrate used routinely for the inhibitory drug-drug interaction assay and isoform-specific inhibitors can be used as positive controls for the assay. Results of inhibition assay are presented as relative activity:

Relative activity (%)=[activity(treatment)/activity (negative control)×100%

Based on the relativity, EC50 values and Ki values are calculated.

Example 18: Hepatocyte P450 Induction Assay to Evaluate Inductive Drug-Drug Interaction 24-well plates are coated with the placenta-derived matrix prepared as described herein. Plateable, cryopreserved human hepatocytes or freshly isolated human hepatocytes are plated in 24-well plates in hepatocyte plating medium (HPM) at a concentration of 0.35-0.40 million in 500 µl per well. The resulting monolayer culture is nearly 100% confluent, and the day of hepatocyte plating is day 0. After 4 hour of culturing, medium is replaced with that containing 0.25 mg/mL placenta-derived matrix. After overnight incubation (day 1), medium is replaced with hepatocyte induction medium (HIM). On day 2, medium is changed to HIM containing the desired concentration of the drug to be evaluated for enzyme induction potential. On days 3, 4 and 5, medium is replaced daily to HIM containing the drugs to be evaluated to allow a total of 72 hours of treatment. On day 6, treatment medium is removed and replaced with 0.5 mL of HMM containing specific drug-metabolizing enzyme substrates, and the plate is incubated for an additional 30 minutes. Acetonitrile is added to terminate metabolism, and centrifuge is used to remove cellular macromolecules. LC/MS or HPLC quantification is performed for drug-metabolizing enzyme metabolism of the substrate. Induction results are expressed as percentage of negative (solvent) control:

Induction (%)=[activity(treatment)/activity(solvent control)×100%

Results are compared to those from positive controls, omeprazole (10 µM; for CYP1A2 induction) and rifampin (10 µM; for CYP3A4 induction).

Example 19: Hepatotoxicity 96-well plates are coated with the placenta-derived matrix prepared as described herein. Hepatocytes are plated in the 96-well plates in hepatocyte metabolism medium (HMM) at a concentration of 35,000 cells in 100 µl per well. The plate is incubated for 24 hours to allow attachment and the formation of a monolayer culture. Medium is changed to hepatocyte incubation medium containing the desired concentration of the drugs to be evaluated for hepatotoxic potential. The plate is incubated for 24 hours, and cytotoxicity is assayed using a desired cytotoxicity endpoint (i.e. for the quantification of cellular ATP content, 50 µl of lysis buffer is added and is followed by 50 µl of luciferin-luciferase reagent followed by quantification of luminescence using multiwell plate reader). Tamoxifen is used as a positive control.

Example 20. A Basic Treatment of ECM-Pepsin Extracts is Necessary to Effectively Inactivate Residual Pepsin Materials. Hydrochloric Acid (BDH, Franklin Lakes N.J.), Hemoglobin from bovine blood (H2625) (Sigma Aldrich, St. Louis Mo.), Trichloroacteic acid (T0699) (Sigma Aldrich, St. Louis Mo.), Pepsin (P7000) (Sigma Aldrich, St. Louis Mo.), Sodium Hydroxide (VWR, Radnor Pa.), and placenta-derived ECM (LifeNet Health IRM, Virginia Beach Va.).

Hemoglobin-based pepsin activity assay. Titration experiments with varying concentrations of pepsin in the test samples were performed to determine the sensitivity of this assay and evaluate its potential use in this study. Briefly, serial dilutions of pepsin in 10 mM hydrochloric acid ranging from 0.1-1.0 mg/ml were prepared from a 2.0 mg/ml stock solution. 0.5 ml of each test solution were mixed with 2.5 ml of a 2.0% hemoglobin substrate solution in glass vials and incubated at 37° C. for exactly 10 min, before stopping the reaction by adding 5.0 ml of a 5.0% Trichloroacetic Acid (TCA) solution. Samples were centrifuged at 1000 rpm for 15 seconds and the supernatant was tested for its spectral absorption at 280 nm. Sample absorptions were normalized to a test solution that was added after the addition of the TCA solution (internal blank).

Effect of pH sweeps on the residual proteolytic activity of pepsin solutions. A pepsin solution of known concentration was subject to controlled pH sweeps to determine their effects on the inactivation of pepsin's proteolytic activity. Briefly, a 0.75 mg/ml pepsin solution was subjected to a pH sweep to pH7.4 ("neutral") or pH8.2 using 1.0 M NaOH, held at this pH for 15 minutes at RT, before returning it back to pH2.0 using 1.0 M HCl. The volume of NaOH and HCl solutions necessary to achieve the pH sweeps in the latter group was monitored and the level of salinity was adjusted in the two other groups using 1.0 M NaCl prior to the completion of the pepsin activity assay.

Effect of pH sweeps on the residual proteolytic activity of pepsin solutions in the presence of ECM and ECM fragments following pepsin solubilization. Decellularized human placenta ECM was solubilized at a concentration of 50 mg/ml in a 1.0 mg/ml pepsin in 0.1 M HCl extraction solution for 5 min, 4 or 24 hours at RT under agitation. Any residual ECM was removed by centrifugation and the resulting test samples were subjected to aforementioned pH sweeps and the residual pepsin activity was determined as described above. A corresponding pepsin solution without the addition of ECM was used to monitor changes in pepsin activity over time.

Figure 3:
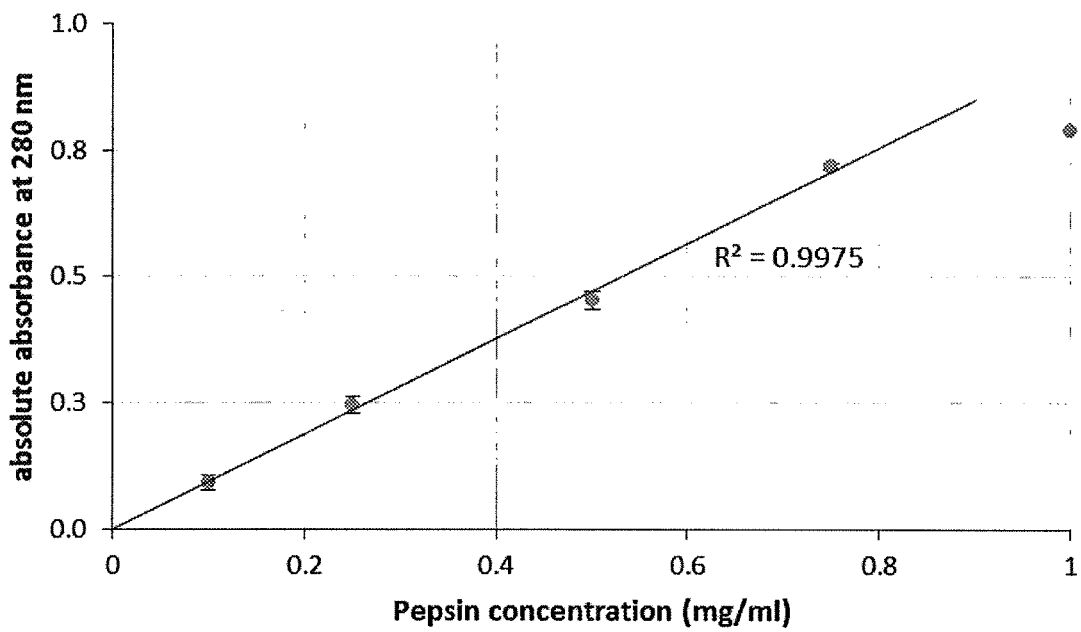
FIG. 3 shows evaluation of assay sensitivity. Pepsin concentration smaller than 0.75 mg/ml resulted in a linear relationship to the test samples' determined absolute absorption. At concentrations greater than 0.75 mg/ml saturation was achieved. Note the high level of reproducibility and the low margin of error between the individual test samples (n=4).

A titration against varying known concentrations of pepsin in the test samples was performed to evaluate the sensitivity of the hemoglobin-based pepsin activity assay at the operational parameters defined by the conventional assay format described by Anson et al. (J. Gen Physiol, 1938. 22(1): p. 79-89). The change in absorption was found to follow a linear behavior with increasing rates of absorption relative to increasing pepsin concentrations (FIG. 3). This linear behavior was observed in a test sample concentration of up to 0.75 mg/ml pepsin. Higher concentrations did not follow this pattern possibly due to a limitation in the hemoglobin substrate available for this reaction in the current format with a reaction duration of 10 min. Nonetheless, the level of variability between different replicates within the same test group was surprisingly low at under 1% and was found to be highly reproducible between independent runs (not shown). A working concentration of 0.75 mg/ml pepsin in 0.1 M HCl in the test solutions was selected for all subsequent experiments to ensure that all assays were carried out at pepsin concentrations falling within this linear region.

Figure 4A:
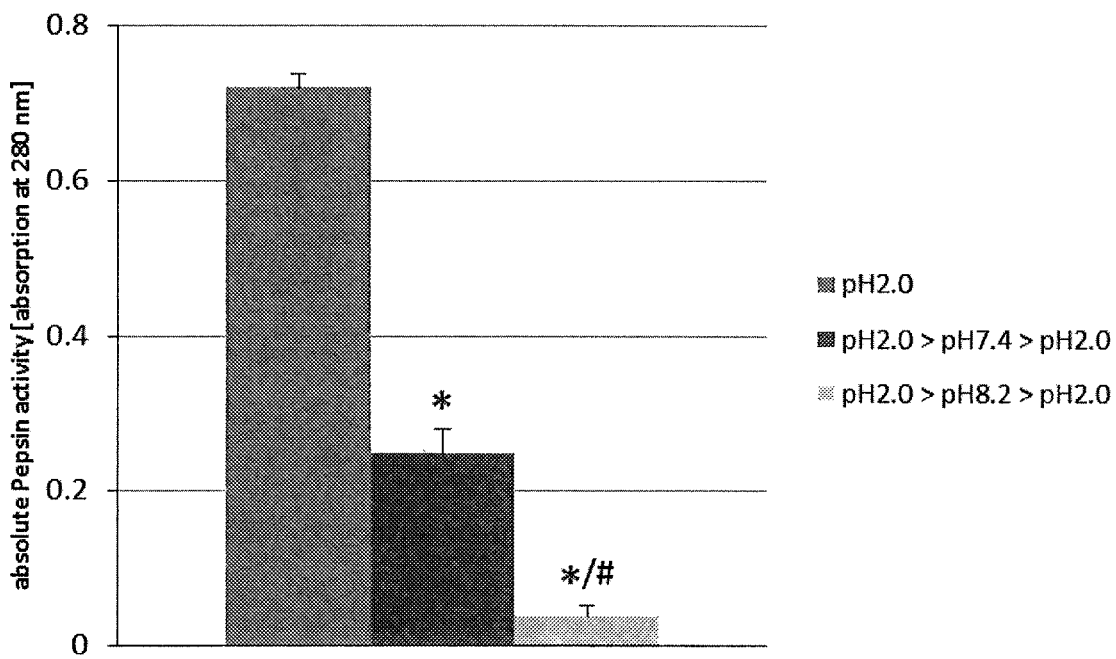
FIGS. 4A and 4B show effects on residual pepsin activity following pH sweeps to pH7.4 or pH8.2. A: Absolute pepsin activity in test samples determined by pepsin activity assay as prepared (0.75 mg/ml, pH2.0) and following pH sweeps to pH7.4 (neutral) or pH8.2, respectively. A pH sweep to neutral or pH8.2 resulted in a significant inactivation of pepsin compared to a non-adjusted sample (*, n=4, P<0.01) with a test sample subject to the pH8.2 sweep showing a significantly greater level of pepsin inactivation than a test sample exposed to a neutral pH sweep (#, n=4, P<0.01) when compared to the test samples exposed to a pH7.4 sweep. B: Relative level of residual pepsin activity in test samples subjected to pH sweeps compared to non-adjusted test samples (pH2.0).
Figure 4B:
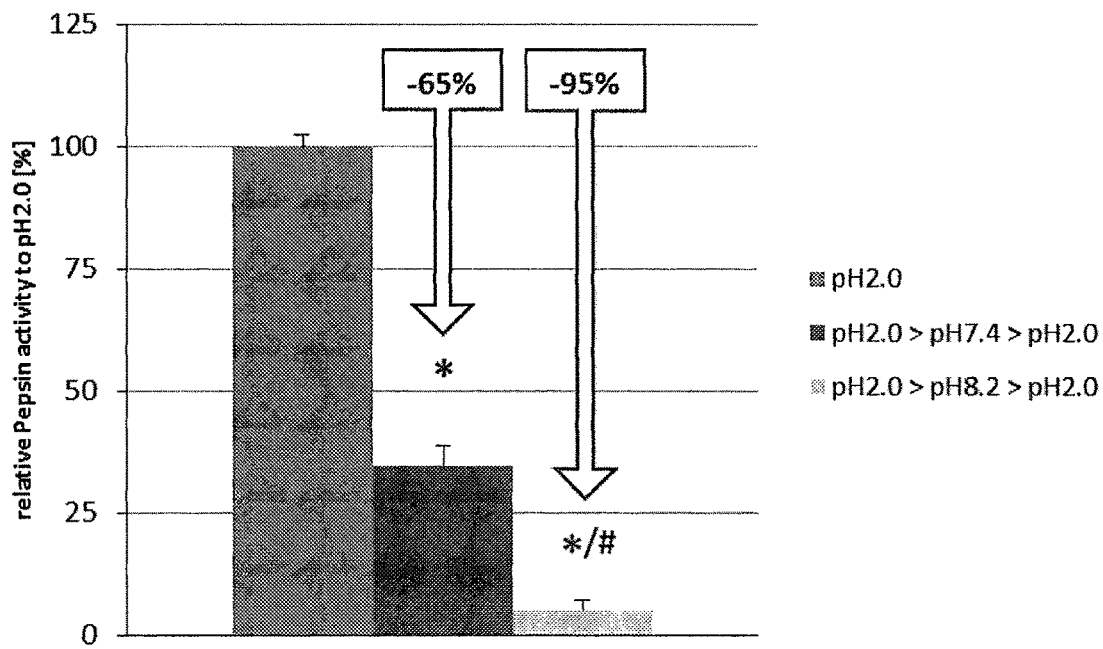

The first set of experiments evaluated the effect of pH sweeps on the reversible and irreversible activity of pepsin solution in the absence of ECM. A defined pepsin solution was subjected to a controlled pH sweep to either a neutral pH of pH7.4 or an elevated, basic pH of pH8.2 before returning it back to pH2.0 (FIGS. 4A and 4B). Either pH sweep resulted in a significant reduction in the residual pepsin activity of the test samples. However, test samples subjected to the neutral pH sweep retained 34.5±1.2% of its pepsin activity indicating that the pH sweep did not result in an irreversible pepsin inactivation. On the contrary, the residual pepsin activity in test samples subjected to the basic pH sweep of pH8.2 was significantly lower showing a residual activity of 5.2±1.0% of the samples original pepsin activity.

Figure 5:
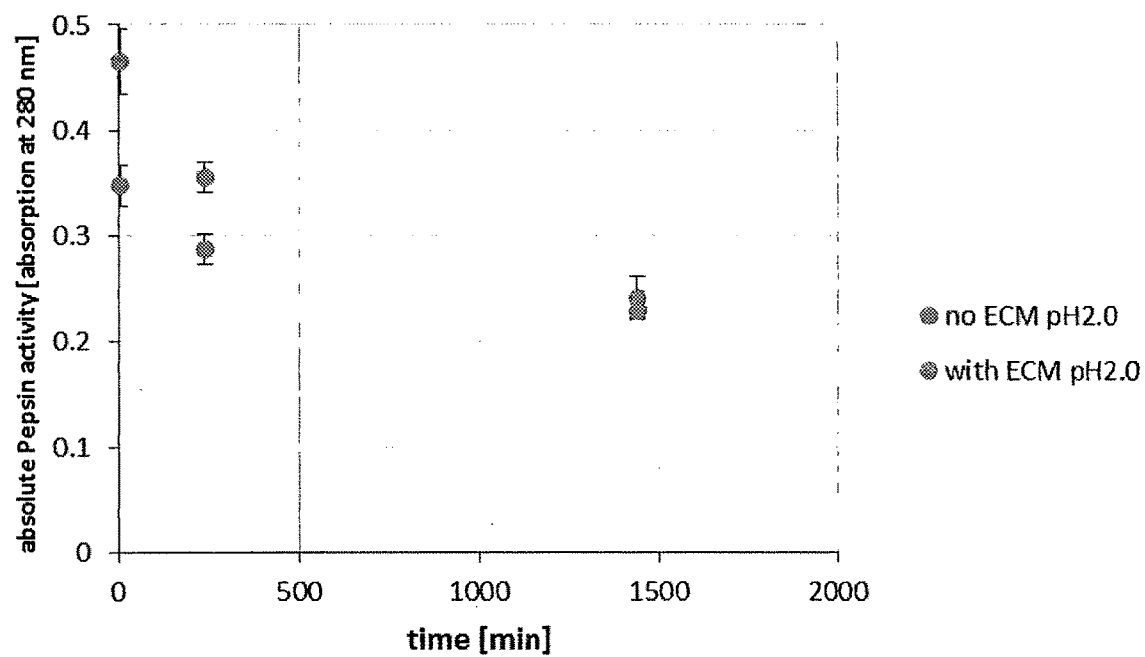
FIG. 5 shows loss of pepsin activity over time. Pepsin solutions and ECM-containing test samples showed a gradual decrease in proteolytic activity over time. At early timepoints, ECM-containing test samples showed a significantly higher proteolytic activity than the pepsin solution alone.
Figure 6A:
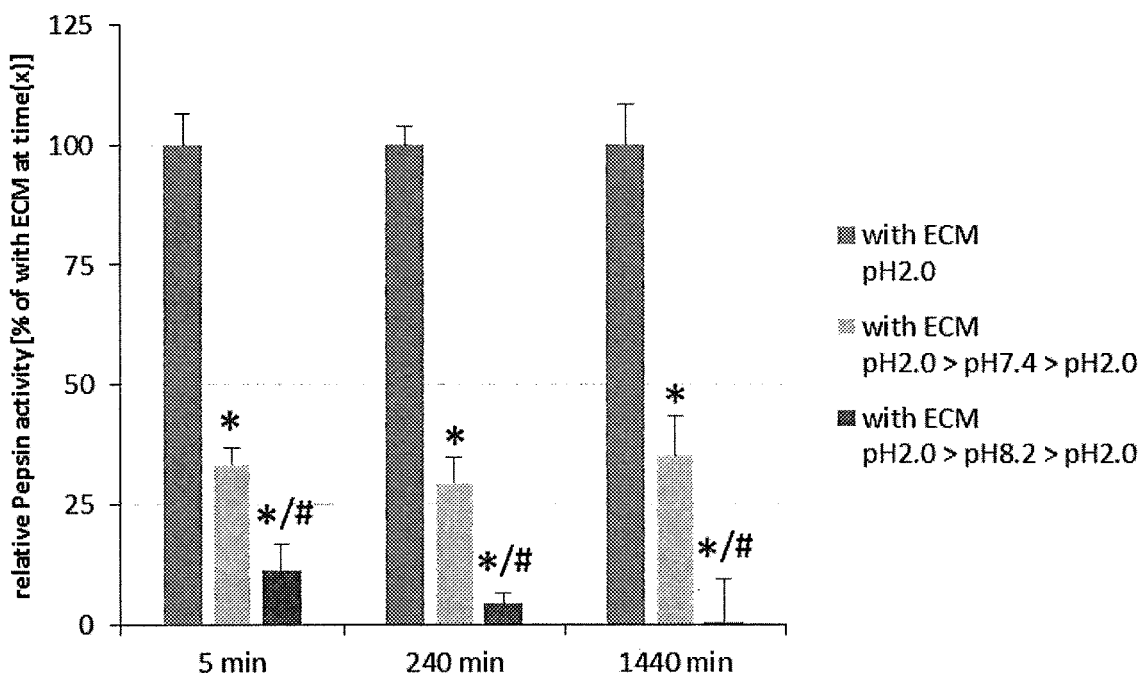
FIGS. 6A and 6B show effects on residual pepsin activity following pH sweeps to pH7.4 or pH8.2 in the Presence of Placenta ECM and Placenta ECM Degradation Products following Pepsin Extraction. A: Absolute pepsin activity in test samples incubated for 5, 240, or 1440 min determined by pepsin activity assay as prepared (0.75 mg/ml, pH2.0) and following pH sweeps to pH7.4 (neutral) or pH8.2, respectively. A pH sweep to neutral or pH8.2 resulted in a significant inactivation of pepsin compared to a non-adjusted sample (n=4, P<0.01) with a test sample subject to the pH8.2 sweep showing a significantly greater level of pepsin inactivation than a test sample exposed to a neutral pH sweep (n=4, P<0.01) when compared to the test samples exposed to a pH7.4 sweep. Note the observed decrease in pepsin activity in all test groups over time and the increased level of proteolytic activity associated with the placenta ECM. B: Relative level of residual Pepsin activity in test samples subjected to pH sweeps compared to non-adjusted test samples (pH2.0)' n=4 per group P<0.01 to pH2.0 (*) and pH7.2 sweep (#).
Figure 6B:
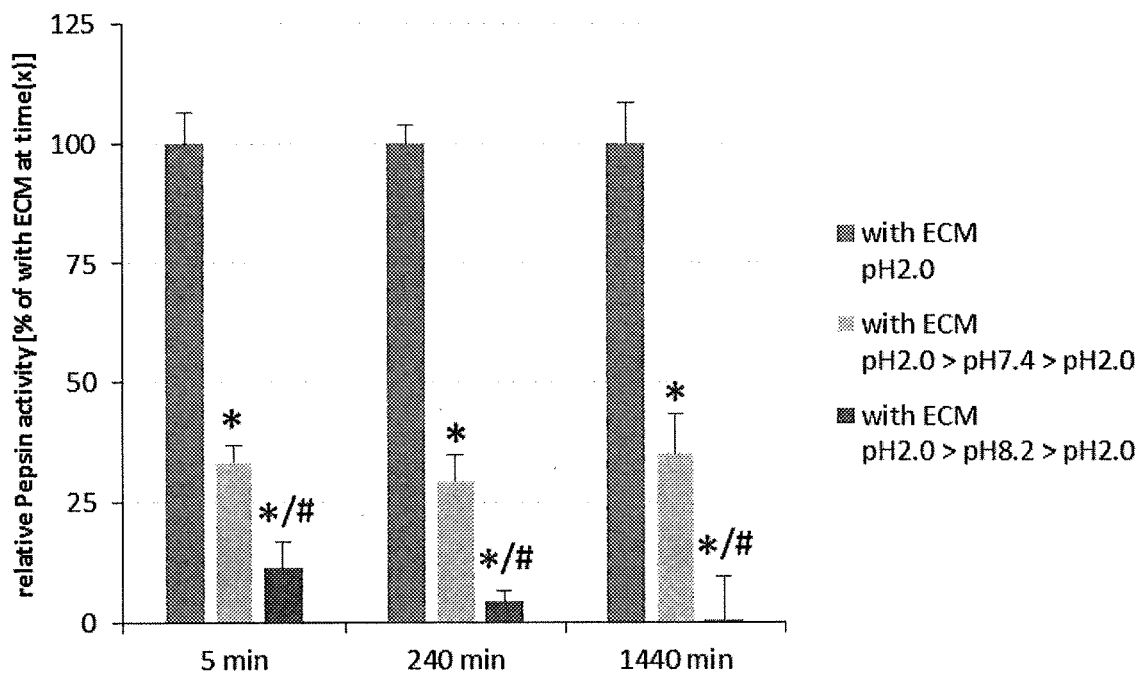

A second set of experiments was completed to assess the effects of ECM and ECM degradation products following pepsin solubilization on the residual pepsin activity of samples and their effect on pepsin inactivation following the two pH sweeps. Human placenta ECM was suspended in pepsin solution and incubated for up to 24 hrs. It was assumed that the early timepoint (5 min of incubation) represents a condition with limited ECM hydrolysis where any observed effects can be generally associated with the presence of solid ECM. The small amount of ECM degradation products is expected to play only a minor role. On the contrary, the late timepoint (24 hrs of incubation) is expected to evaluate the effects caused by both ECM and ECM degradation products. Incubation of pepsin solutions without the presence of ECM resulted in a gradual loss of activity over time (FIG. 5). This drop in activity is common in biologically and biochemically active compounds and can be attributed to the gradual denaturation of active proteins over time when in solution. A similar pattern was observed for ECM-containing samples (FIG. 6). Interestingly, ECM-containing test samples showed a higher level of proteolytic activity than test samples without ECM. This difference may be caused by other proteolytically active enzymes present. However, this difference between these two groups could not be observed after 24 hours of incubation, when the proteolytic activity equals the level observed in ECM-free test samples, suggesting that these proteases may also be susceptible to events of enzyme denaturation.

ECM-containing test samples were subject to the two pH sweeps to either neutral pH (pH7.2) or basic pH (pH8.2) to evaluate their effects on pepsin inactivation in the presence of ECM and ECM degradation products. At all timepoints, either pH sweep resulted in a significant reduction in the residual pepsin activity of the test samples. However, test samples subjected to the neutral pH sweep (pH7.2) retained 29.5±5.6% to 35.3±8.2% of its proteolytic activity, while test samples subjected to the basic pH sweep of pH8.2 showed a significantly lower level of residual proteolytic activity with 11.3±5.4% to 0.6±8.9% of the samples original pepsin activity. The level of pepsin inhibition during the respective pH sweeps was not affected by the presence of ECM (5 min) nor an increasing level of potentially inhibitory ECM degradation products (4 or 24 hrs of incubation) as outlined in Table 1.

TABLE 1

Relative Changes in Pepsin Activity in the Presence of Placenta ECM and ECM Degradation Products.

| Group | Change in relative level of Pepsin activity to pH 2.0 [%] | | |
|---|---|---|---|
| Time of Incubation [min] | 5 | 240 | 1440 |
| with ECM pH 2.0 | 0 | 0 | 0 |
| with ECM pH 2.0 > pH 7.4 > pH 2.0 | −66.5 ± 3.4 | −70.5 ± 5.6 | −64.7 ± 8.2 |
| with ECM pH 2.0 > pH 8.2 > pH 2.0 | −88.7 ± 5.4 | −95.6 ± 2.1 | −99.4 ± 8.9 |

The present study highlighted the following findings: 1) a pH sweep across neutral pH (pH7.4) only results in a partial inactivation of pepsin and the retention of approximately 35% of the sample's original pepsin activity, 2) a pH sweep across basic pH (pH8.2) results in almost complete inactivation of pepsin and 3) The presence of ECM and/or ECM-degradation products do not result in pepsin inactivation.

Example 21: Biological Tests of Human Placenta-Derived Matrix

A temperature sensitive human placenta-derived matrix was prepared according to the method described in Example 1 and tested as a substrate to support the culture of various types of cells. This test matrix turned into a gel in a temperature-dependent manner.

Handling.

Dilution. A stock solution of the test matrix (approximately 5 mg/ml) stored at −80° C. was slowly thawed on ice to keep the test matrix in liquid. The test matrix solution was then diluted with either DPBS or DMEM at 4° C. on the ice into 1:2 (2.5 mg/ml), 1:5 (1 mg/ml), 1:10 (0.5 mg/ml), 1:15 (0.33 mg/ml), 1:30 (0.16 mg/ml), or 1:50 (0.1 mg/ml).

Coating. Various concentrations of the test matrix was directly applied to tissue culture plastic plates and placed at 4° C. or room temperature for 24 hours (1 ml/well for 6 well plate; 500 ul/well for 12 well plate) to obtain plates coated by the test matrix. The test matrix solution of pH 8.0 made more homogeneous protein particles coating on tissue culture plastic plates than the text matrix solution of pH 6.0.

Cell culture on test matrix.

Cell seeding. Cell culture medium was dispensed to the plates coated with the test matrix prior to cell seeding.

Human iPSCs culture. Human iPSCs were passaged as clumps and were not dissociated into single cells. Similar number of iPSC clumps were seeded onto the plates coated with various concentrations of the test matrix compared to plates coated by a control matrix, MATRIGEL (Corning Incorporated, Tweksbury, Mass.). The number of colonies successfully attached was counted one (1) day after iPSC seeding on both matrices.

Differentiation Induction of Human iPSC on Test Matrix.

Lineage-specific differentiation of iPSCs. iPSC differentiation induction was initiated by forming embryoid body by collagenase IV treatment. EBs differentiating in suspension culture under specific differentiation induction medium conditions were plated onto tissue culture plates coated with the test matrix for further maturation. Neural differentiation and cardiomyocyte differentiation were studied.

Neural differentiation. EBs guided differentiation towards neural lineage were cultured in suspension for 7 days in the presence of N2/B27 and then plated onto plates coated with the test matrix for additional maturation for 7-10 days with N2/B27 and bFGF treatment.

Cardiomyocyte differentiation. Initial EB suspension culture was conducted by treating BMP-4 and Activin A for 7 days and then plated onto plate coated with the test matrix in the presence of BMP-4, Activin-A, bFGF and ascorbic acid for additional 10-14 days.

Characterization of differentiated cells by marker expression. iPSC-derived neural cells or cardiomyocytes were identified by staining with neural (Nestin, A2B5, Tuj-1)- or cardiomyocyte-specific markers and then detected by imaging or flow cytometry.

Cell Attachment on the Test Matrix (pH Dependency).

Human iPSCs plated onto plates coated with the test matrix. Human iPSC colonies were successfully attached on the test matrix of pH 8.0 over 90% whereas the test matrix of pH 6.0 could only support around 40% of iPSC colony attachment.

What is claimed:

1. A method of preparing a hydrogel obtained from a placental tissue, said method comprising
    (a) devitalizing a placenta tissue to produce a devitalized placenta tissue,
    (b) digesting the devitalized placenta tissue in a digestion solution having a pepsin and hydrochloric acid (HCl) to produce a placenta-derived matrix,
    (c) adjusting pH of the placenta-derived matrix from step (b) to a basic pH of 8.0 to 11.0 to irreversibly inactivate the pepsin,
    (d) adjusting the pH of the placenta-derived matrix from step (c) to a neutral pH of 7.0 to 7.2 to prepare a first neutralized placenta-derived matrix,
    (e) freeze-drying the first neutralized placenta-derived matrix to produce a sponge structure,
    (f) dissolving the sponge structure in an acetic acid solvent to form a second placenta-derived matrix, (g) adjusting the pH of the second placenta-derived matrix from step (f) to a neutral pH of 7.0 to 7.2 to prepare a second neutralized placenta-derived matrix, and (h) adjusting the temperature of the second neutralized placenta-derived matrix to 36 to 38° C. to produce the hydrogel.

2. The method of claim 1, wherein step (a) comprises treating the placenta tissue with a non-denaturing detergent.

3. The method of claim 1, further comprising homogenizing the devitalized placenta tissue concurrently with or before digesting the devitalized placenta tissue of step (b).

4. The method of claim 3, wherein the devitalized placenta tissue is homogenized at 4° C.

5. The method of claim 1, wherein the concentration of pepsin in the digestive solution is from 400 to 700 units/ml, and the concentration of HCl in the digestive solution is 0.01M-1.0M.

6. The method of claim 1, further comprising storing cells on or in the hydrogel.

7. The method of claim 6, wherein the cells on or in the hydrogel is stored by cryopreservation.

8. The method of claim 1, further comprising exposing a protein to the hydrogel.

9. The method of claim 1, further comprising
(a) mixing cells in the hydrogel to produce a mixture, and
(b) injecting the mixture into a site of interest.

10. The method of claim 1, further comprising culturing pluripotent stem cells or tissue-specific progenitor cells on or within the hydrogel.

11. The method of claim 1, further comprising coating at least a part of a surface of a substrate with the hydrogel.

* * * * *